(12) United States Patent
Turner et al.

(10) Patent No.: US 10,766,890 B2
(45) Date of Patent: Sep. 8, 2020

(54) HEPATITIS B CORE PROTEIN MODULATORS

(71) Applicants: Assembly Biosciences, Inc., Carmel, IN (US); INDIANA UNIVERSITY RESEARCH AND TECHNOLOGY CORPORATION, Indianapolis, IN (US)

(72) Inventors: William Turner, Bloomington, IN (US); Hans Maag, Kleires Wiesental (DE); Samson Francis, Indianapolis, IN (US)

(73) Assignees: Assembly Biosciences, Inc., South San Francisco, CA (US); INDIANA UNIVERSITY RESEARCH AND TECHNOLOGY CORPORATION, Indianapolis, IN (US)

(*) Notice: Subject to any disclaimer, the term of this patent is extended or adjusted under 35 U.S.C. 154(b) by 0 days.

(21) Appl. No.: 15/760,387

(22) PCT Filed: Sep. 15, 2016

(86) PCT No.: PCT/US2016/051949
§ 371 (c)(1),
(2) Date: Mar. 15, 2018

(87) PCT Pub. No.: WO2017/048962
PCT Pub. Date: Mar. 23, 2017

(65) Prior Publication Data
US 2018/0265484 A1  Sep. 20, 2018

Related U.S. Application Data

(60) Provisional application No. 62/218,815, filed on Sep. 15, 2015.

(51) Int. Cl.

| | | |
|---|---|---|
| C07D 417/12 | (2006.01) | |
| A61P 31/20 | (2006.01) | |
| C07D 281/16 | (2006.01) | |
| C07D 403/12 | (2006.01) | |
| A61K 45/06 | (2006.01) | |
| C07D 401/12 | (2006.01) | |
| C07D 413/12 | (2006.01) | |
| C07D 417/14 | (2006.01) | |
| C07D 453/02 | (2006.01) | |
| C07D 471/04 | (2006.01) | |
| C07D 243/38 | (2006.01) | |
| C07D 267/20 | (2006.01) | |

(52) U.S. Cl.
CPC .......... *C07D 417/12* (2013.01); *A61K 45/06* (2013.01); *A61P 31/20* (2018.01); *C07D 243/38* (2013.01); *C07D 267/20* (2013.01); *C07D 281/16* (2013.01); *C07D 401/12* (2013.01); *C07D 403/12* (2013.01); *C07D 413/12* (2013.01); *C07D 417/14* (2013.01); *C07D 453/02* (2013.01); *C07D 471/04* (2013.01)

(58) Field of Classification Search
None
See application file for complete search history.

(56) References Cited

U.S. PATENT DOCUMENTS

| | | |
|---|---|---|
| 5,512,563 A | 4/1996 | Albright et al. |
| 8,618,090 B2 | 12/2013 | Desai et al. |
| 9,399,619 B2 | 7/2016 | Guo et al. |
| 9,873,684 B2 | 1/2018 | Kahraman et al. |
| 2007/0105819 A1 | 5/2007 | Olsson et al. |
| 2007/0105835 A1 | 5/2007 | Kazantsev |
| 2015/0368261 A1 | 12/2015 | Demin et al. |
| 2017/0107185 A1 | 4/2017 | Grammneos et al. |
| 2017/0267685 A1 | 9/2017 | D'Agostino et al. |

FOREIGN PATENT DOCUMENTS

| | | | |
|---|---|---|---|
| CL | 2015002706 A1 | 4/2016 | |
| CL | 2015003456 A1 | 7/2016 | |
| CL | 20105002628 | 8/2016 | |
| CL | 2016003175 A1 | 8/2017 | |
| GB | 1480553 A | 7/1977 | |
| JP | 58225074 | 12/1983 | |
| WO | WO-92/19277 A1 | 11/1992 | |
| WO | WO-2005/072741 A1 | 8/2005 | |
| WO | WO-2008/036139 A3 | 12/2008 | |
| WO | WO-2008/118141 A3 | 12/2008 | |
| WO | WO-2010/011537 A1 | 1/2010 | |
| WO | WO-2012/045194 A1 | 4/2012 | |
| WO | WO 2013/006394 * | 1/2013 | ........... C07D 211/06 |
| WO | WO-2013/006394 A1 | 1/2013 | |
| WO | WO-2015/017412 A1 | 2/2015 | |
| WO | WO 2015/138895 * | 9/2015 | ............ A01N 43/00 |
| WO | WO-2015/138895 A1 | 9/2015 | |

OTHER PUBLICATIONS

Ito et al. in Cancer Science 94(1), 3-8 (2003).*
STN Registry database entry for CAS RN 688762-67-6, Entered STN Jun. 3, 2004, Accessed Aug. 8, 2019.*
Extended European Search Report issued in EP16847298.3, dated Jan. 2, 2019.
Supplemental European Search Report issued by the European Patent Office (Munich), dated Apr. 11, 2018, for related Application No. EP 15761201; 21 pages.
Takeda, M., et al., "Synthesis of Dibenzo [b,e] [1,4] Diazepine Derivatives as Anti-depressants," Yakugaku Zahhi, vol. 89, No. 2, (1969), 6 pages.
National Center for Biotechnology Information, PubChem Compound Database; CID-4152425, XP-002779931, modified Apr. 7, 2017, created Sep. 13, 2005; 3 pages.

(Continued)

*Primary Examiner* — Alicia L Otton
(74) *Attorney, Agent, or Firm* — Goodwin Procter LLP

(57) ABSTRACT

The present disclosure provides, in part, compounds having allosteric effector properties against Hepatitis B virus Cp. Also provided herein are methods of treating viral infections, such as hepatitis B, comprising administering to a patient in need thereof a disclosed compound.

15 Claims, No Drawings

Specification includes a Sequence Listing.

(56) References Cited

OTHER PUBLICATIONS

National Center for Biotechnology Information, PubChem Compound Database; CID-46260649, XP-002779932, modified Apr. 7, 2017, created Jul. 21, 2010; 3 pages.
National Center for Biotechnology Information, PubChem Compound Database; CID-4163919, XP-002779933, modified Apr. 7, 2018, created Sep. 13, 2005; 3 pages.
National Center for Biotechnology Information, PubChem Compound Database; CID-4167865, XP-002779934, modified Apr. 7, 2018, created Sep. 13, 2005; 3 pages.
National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.
National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified 20187-11-18, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.
English translation of the First Official Action issued by the Mexican Patent Office for Mexican Patent Application No. MX/a/2016/011800, dated Jul. 4, 2018; 3 pages.
Letter dated Jun. 27, 2018 regarding Examination Report issued by the National Office of Industrial Property for Dominican Republic Patent Application No. P2016-0233; 2 pages.
Supplemental Partial European Search Report issued by the European Patent Office (Munich), dated Nov. 23, 2017, for related Application No. EP 15761201; 14 pages.
Letter Exam Report issued by the Patent Office of the People's Republic of China (translated in English language), dated Jun. 29, 2018, for Chinese Application No. 201580024580.0; (3 pages).
Letter Exam Report issued by the Chilean Patent Office, dated Jun. 12, 2018, for Chilean Application No. 2269-2016; 15 pages.
National Center for Biotechnology Information, PubChem Compound Database; CID-23734106, XP-002779939, modified Apr. 7, 2018, created Feb. 20, 2008; 3 pages.
Hall, Pamela R., et al., "Small molecule inhibitors of hantavirus infection,"Bioorganic & Medicinal Chemistry Letters, vol. 20, (2010), pp. 7085-7091.
Xiao, et al., "Discovery, Optimization, and Characterization of Novel D2 Dopamine Receptor Selective Antagonists," Journal of Medicinal Chemistry, Mar. 25, 2014, vol. 57, pp. 3450-3463.
International Preliminary Report on Patentability issued by the International Bureau of WIPO, dated Sep. 13, 2016, for International Application No. PCT/US2015/020444; 6 pages.
International Search Report and Written Opinion issued by the ISA/US, Commissioner for Patents, dated Jul. 6, 2015, for International Application No. PCT/US2015/020444; 10 pages.
National Center for Biotechnology Information. PubChem Compound Database; CID=20885151; available at https://pubchem.ncbi.nlm.nih.gov/compound/20885151 (accessed Sep. 13, 2016; deposit date Dec. 5, 2007); 10 pages.
National Center for Biotechnology Information. PubChem Compound Database; CID=4 II 9171, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID=4167865, https://pubchem.ncbi.nlm.nih.gov/compound/4167865 (accessed Sep. 13, 2016; deposit date Sep. 13, 2005); 12 pages.
International Preliminary Report on Patentability dated Mar. 20, 2018, for International Application No. PCT/US2016/051934 (6 pages).
International Search Report and Written Opinion dated Dec. 29, 2016 for International Application No. PCT/US16/51934.
International Preliminary Report on Patentability dated Dec. 29, 2016, for International Application No. PCT/US2016/051949.
International Search Report and Written Opinion dated Dec. 29, 2016 for International Application No. PCT/US16/51949.
International Preliminary Report on Patentability dated Oct. 28, 2016, for International Application No. PCT/US2016/051940.
International Search Report and Written Opinion dated Oct. 28, 2016 for International Application No. PCT/US16/51949.
National Center for Biotechnology Information, PubChem Compound Database; CID-201327, create date: Aug. 9, 2005; 3 pages.
Supplementary European Search Report issued for EP16847298, dated Jan. 28, 2019 (6 pages).
Notice of Reasons for Rejection issued for Japanese Patent Application No. 2016-557019, dated Oct. 30, 2018 (6 pages).
Official Office Action issued in Eurasian application No. 201890731, dated Oct. 31, 2018.
Office Action issued by the Belize Intellectual Property Office, dated Nov. 21, 2018, for Belize Patent Application No. 925.18 (3 pages).
Extended European Search Report issued for European Patent Application No. 16847295.9, dated Apr. 15, 2019.
Xiao, et al.. "Discovery, Optimization, and Characterization of Novel D2 Dopamine Receptor Selective Antagonists", Journal of Medicinal Chemistry, vo. 57, p. 3450-63 (2014).
Office Action issued by the Chinese Intellectual Property Office, dated Mar. 17, 2020, for Chinese Patent Application No. 201680065139.1.

\* cited by examiner

HEPATITIS B CORE PROTEIN MODULATORS

CROSS REFERENCE TO RELATED APPLICATIONS

The present application is a U.S. National Phase Application under 35 U.S.C. § 371 of International Application PCT/US2016/051949, filed Sep. 15, 2016, which claims priority to U.S. Provisional Application 62/218,815, filed Sep. 15, 2015, hereby incorporated by reference in its entirety.

BACKGROUND

Hepatitis B (HBV) causes viral Hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million to deaths (2009; WHO, 2009). HBV can be spread by body fluids: from mother to child, by sex, and via blood products. Children born to HBV-positive mothers may also be infected, unless vaccinated at birth.

The virus particle is composed of a lipid enveloped studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core. For convenience, we divide the assembly process at the point of capsid assembly and pgRNA-packaging. Steps preceding this event are "upstream"; steps following RNA-packaging are "downstream".

At present, chronic HBV is primarily treated with nucleos(t)ide analogs (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, nucleos(t)ide therapy may lead to the emergence of antiviral drug resistance (Deres and Rubsamen-Waigmann, 1999; Tennant et al., 1998; Zhang et al., 2003) and—in rare patients—adverse events have been reported (Ayoub and Keeffe, 2011).

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon based therapies are used in only a small percentage of all diagnosed patients who elect for treatment.

Thus, current HBV treatments can range from palliative to watchful waiting. Nucleos(t)ide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

Provided herein are compounds that can have properties such as those described below, where the compounds in some embodiments may be represented by:

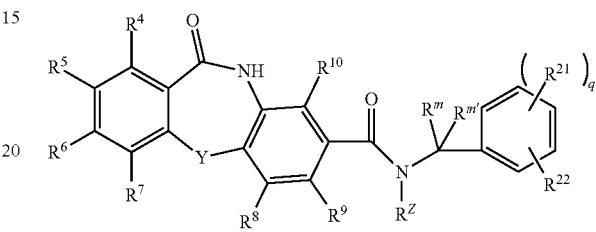

wherein
$R^4$, $R^5$, $R^6$, $R^7$, $R^8$, $R^9$, $R^{10}$, $R^m$, $R^{m'}$, $R^{21}$, $R^{22}$, $R^Z$, Y, and q are defined herein. Also provided herein are methods of treating viral infections, such as hepatitis B, comprising administering to patient a disclosed compound.

For example, the present disclosure is directed in part to compounds having allosteric effector properties against Hepatitis B virus Cp, a protein found as a dimer, a multimer, and as the protein shell of the HBV core. Without being bound by theory, disclosed compounds may ultimately target multimerization of viral core proteins, which is central to HBV infection, where the core protein multimerizes into shell, or capsid, and/or disclosed compounds may for example, ultimately target interaction of viral core proteins with other macromolecules, such as host or viral nucleic acid, host proteins, or other viral proteins. For example, disclosed compounds may be considered in some embodiments CpAM—core protein allosteric modifiers. CpAM interaction with core protein can allosterically favor an assembly-active form of Cp dimer and lead to viral capsid assembly at an inappropriate time or place or lead to non-standard intersubunit interactions, all resulting in defective capsids. CpAMs may additionally or alternatively affect steps of "upstream" of capsid assembly by altering the concentrations or nature of Cp available as dimer as compared to capsid or other multimeric forms. Disclosed compounds or CpAMs may, in some embodiments, noticeably affect functions upstream of viral assembly such as modulation of cccDNA transcription, RNA stability and/or protein-protein interactions.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As intended herein, the terms "a" and "an" include singular as well as plural references unless the context clearly dictates otherwise. For example, the term "an assembly effector" can include one or more such effectors.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The terms "hydroxy" and "hydroxyl" as used herein refers to the radical —OH.

"Treatment" as used herein includes the alleviation, prevention, reversal, amelioration or control of a pathology, disease, disorder, process, condition or event, including viral infection. In this context, the term "treatment" is further to be understood as embracing the use of a drug to inhibit, block, reverse, restrict or control progression of viral infection.

As used herein, the term "pharmaceutical composition" refers to compositions of matter comprising at least one pharmaceutical compound and optionally a pharmaceutically acceptable carrier.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ===== denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z"

or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}F$, $^{32}F$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, form ate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen. US2011/0144086 describes the use of some diabenzothiazepine molecules (DBTs) as anti-malarial "inhibitors of the plasmodial surface anion channel." However, no study of DBT molecules as anti-virals has yet been reported.

In an embodiment, provided herein are compounds represented by:

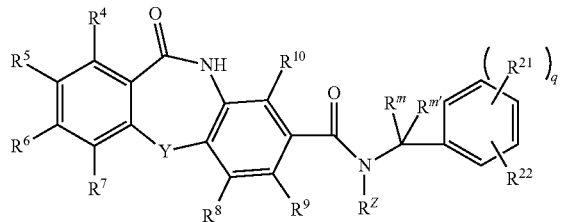

wherein

Y is selected from the group consisting of $S(O)_y$, C=O, $C(R^{11})_2$, $NR_y$, and O wherein y is 0, 1, or 2; $R^{11}$ is H or $C_{1-6}$alkyl, $R_y$ is selected from the group consisting of H, methyl, ethyl, propyl, proprenyl, butyl, phenyl and benzyl, wherein $R_Y$ when not H may be optionally substituted by hydroxyl;

$R^Z$ is selected from the group consisting of H, methyl, ethyl, propyl, phenyl and benzyl;

$R^{m'}$ and $R^m$ are each independently selected from the group consisting of H and $C_{1-6}$alkyl (optionally substituted by one, two or three substituents each independently selected from halogen and hydroxyl);

$R^{21}$ is selected for each occurrence from the group consisting of H, halogen, and $C_{1-6}$alkyl;

q is 0, 1, or 2;

$R^{22}$ is selected for each occurrence from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, —C(O)—NR'R", —C(=NH)—NR'R", $X^2$-phenyl (optionally substituted by one, two or three substituents represented by $R^{63}$), phenyl (optionally substituted by one, two or three substituents represented by $R^{63}$), 5-6 membered monocyclic heteroaryl (optionally substituted by one, two or three substituents represented by $R^{63}$), 9-10 membered bicyclic heteroaryl (optionally substituted by one, two or three substituents represented by $R^{73}$), $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$, (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-7 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

$R^{63}$ is selected independently at each occurrence from the group consisting of H, halogen, hydroxyl, nitro, cyano, carboxy, $C_{1-6}$alkyl, —C(O)—O—$C_{1-6}$alkyl, heterocycle (optionally substituted by halogen or NR'R'), —C(O)—NR'R", —C(=NH)—NR'R", heteroaryl, phenyl, benzyl, $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), $X^2$—$R^{69}$;

$R^{69}$ is selected from the group consisting of H, halogen, hydroxyl, nitro, cyano, $C_{1-6}$alkyl, —C(O)—O—$C_{1-6}$alkyl, heterocycle (optionally substituted by halogen or NR'R'),), —C(O)—NR'R", —C (=NH)—NR'R", heteroaryl, phenyl, $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2);

$X^2$ is selected from S(O), (wherein w is 0, 1, or 2), O, $CH_2$, or NR';

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, $C_{1-6}$alkoxy, NR'R", —NR'—S(O)$_w$—$C_{1-6}$alkyl (where w is 0, 1 or 2), and S(O)$_w$—NR'R"(where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$—$C_{1-6}$alkyl (where w is 0, 1 or 2), and S(O)$_w$—NR'R" (where w is 0, 1 or 2);

For example, in some embodiments Y is $S(O)_y$. In some embodiments, Y is NH. In some embodiments, y is 1 or 2. In some embodiments, y is 0. In some embodiments, q is 0.

For example, in some embodiments $R^{22}$ is selected for each occurrence from the group consisting of NR'R", —C(O)—$C_{1-6}$alkoxy, —C(O)—NR'R", —C(=NH)—NR'R", $X^2$-phenyl (optionally substituted by one, two or three substituents represented by $R^{63}$), phenyl (optionally substituted by one, two or three substituents represented by $R^{63}$), $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$, (where w is 0, 1 or 2).

For example, in some embodiments $R^{22}$ is selected from the group consisting of $X^2$-phenyl (optionally substituted by one, two or three substituents represented by $R^{63}$), phenyl (optionally substituted by one, two or three substituents represented by $R^{63}$), 5-6 membered monocyclic heteroaryl (optionally substituted by one, two or three substituents represented by $R^{63}$), and 9-10 membered bicyclic heteroaryl (optionally substituted by one, two or three substituents represented by $R^{73}$).

For example, In some embodiments one $R^{22}$ is $X^2$-phenyl (optionally substituted by one, two or three substituents represented by $R^{63}$). In some embodiments one $R^{22}$ is phenyl (optionally substituted by one, two or three substituents represented by $R^{63}$). In some embodiments one $R^{22}$ is a 5-6 membered monocyclic heteroaryl (optionally substituted by one, two or three substituents represented by $R^{63}$) or a 9-10 membered bicyclic heteroaryl (optionally substituted by one, two or three substituents represented by $R^{73}$). In some embodiments $R^{22}$ is represented by a substituent selected from the group consisting of:

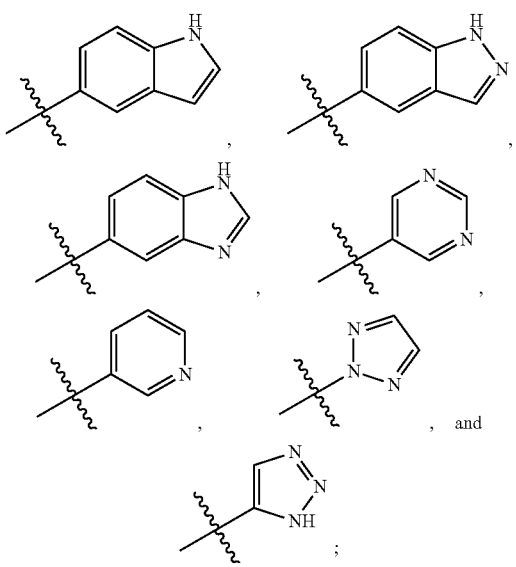

wherein each $R^{22}$ is optionally substituted by one, two or three substituents represented by $R^{63}$.

An exemplary compound may be represented by:

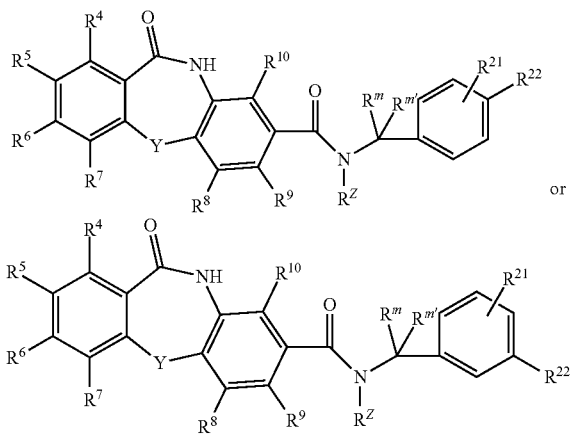

wherein $R^{21}$ is selected, for each occurrence, from the group consisting of H, halogen, and $C_{1-6}$alkyl.

For example, in some embodiments the compound is represented by:

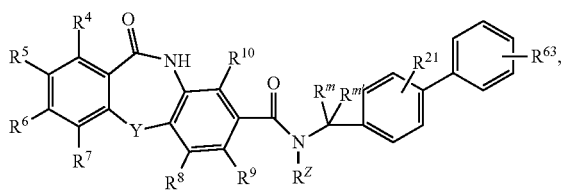

wherein $R^{21}$ is selected, for each occurrence, from the group consisting of H, halogen, and $CH_3$.

For example, in some embodiments the compound is represented by:

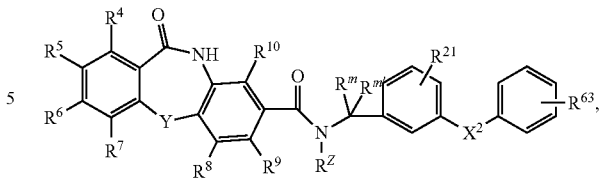

wherein $X^2$ is selected from the group consisting of O, $CH_2$, and S, and $R^{21}$ is selected, for each occurrence, from the group consisting of H, halogen, and $CH_3$.

For example, in some embodiments $R^{63}$ is selected independently at each occurrence from the group consisting of H, halogen, hydroxyl, nitro, cyano, $C_{1-6}$alkyl, $C_{1-6}$haloalkyl, —$C_{1-6}$alkyl-OH, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkoxy, $C_{3-6}$cycloalkyl, (where w is 0, 1 or 2), —S(O)$_w$—NR'R" (where w is 0, 1 or 2), —NR'—S(O)$_w$—$C_{1-6}$alkyl (where w is 0, 1 or 2) and —NR'—S(O)$_w$, (where w is 0, 1 or 2) and $X^2$—$C_{1-6}$alkyl-$R^{69}$.

For example, in some embodiments $R^{63}$ is selected independently at each occurrence from the group consisting of H, halogen, hydroxyl, cyano, OH, $C_{1-6}$alkyl-NR'R", —O—$C_{1-6}$alkyl-NR'R", —$C_{1-6}$alkyl-OH, —C(O)—NR'R", $C_{1-6}$alkoxy, carboxy, NR'R", and benzyl.

For example, the present disclosure also provides, in part, a compound selected from the group consisting a compound of Table 3 and pharmaceutically acceptable salts thereof. In an embodiment, the present disclosure provides a pharmaceutically acceptable composition comprising a disclosed compound, and a pharmaceutically acceptable excipient.

In a further aspect, a method for treating a hepatitis B infection in a patient in need thereof is provided, comprising administering to a subject or patient an effective amount of a disclosed compound, and/or administering a first disclosed compound and optionally, and additional, different disclosed compound(s). In another embodiment, a method for treating a hepatitis B infection in a patient in need thereof is provided, comprising administering to a subject or patient a therapeutically effective amount of a pharmaceutical composition comprising a disclosed compound, or two or more disclosed compounds.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 µg/kg body weight. In some cases, the administration dose of the compound may be less than 400 µg/kg body weight. In other cases, the administration dose may be less than 200 µg/kg body weight. In yet other cases, the administration dose may be in the range between about 0.1 to about 100 µg/kg body weight. The dose may be conveniently administered once daily, or in divided doses up to, for example, four times a day or in sustained release form.

A compound may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating patient suffering from hepatitis B comprising administering to a subject a first amount of a disclosed compound and a second amount of an antiviral, or other anti HBV agent, for example a second amount of a second compound selected from the group consisting of: another HBV caspid assembly promoter (such as certain compounds disclosed herein or for example, GLS4, BAY 41-4109, AT-130, DVR-23 (e.g., as depicted below),

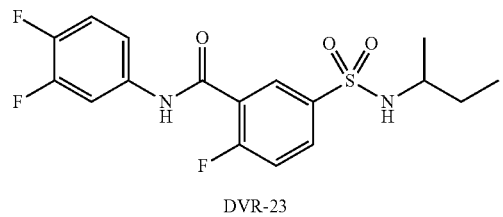

DVR-23

NVR 3-778, NVR1221 (by code); and N890 (as depicted below):

other CpAMs such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleoside analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofavir (e.g. AGX-1009), L-FMAU (Clevudine), LB80380 (Besifovir) and:

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

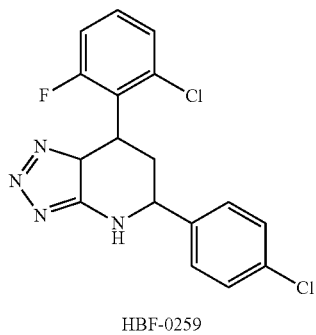

HBF-0259

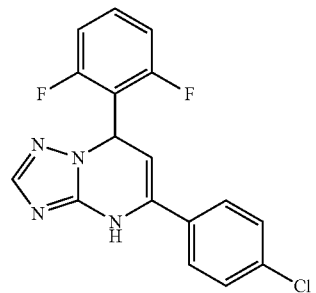

PBHBV-2-15 and BM601 as depicted below:

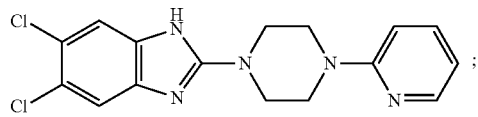 [SMILES: Clc1cc2nc(N3CCN(c4ccccn4)CC3)[nH]c2cc1Cl]

disruptors of nucleocapsid formation or integrity such as NZ-4/W28F:

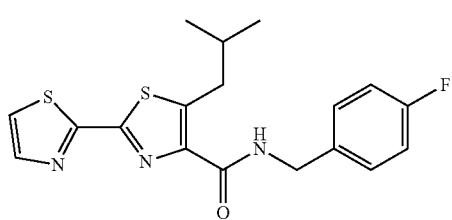

NZ-4 to cccDNA formation inhibitors: such as BSBI-25, CCC-0346, CCC-0975 (as depicted below):

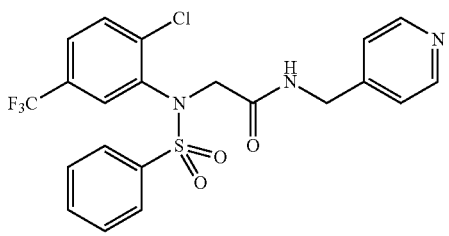

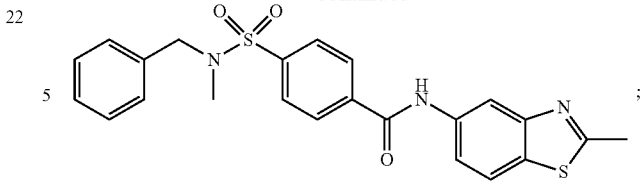

HBc directed transbodies such as those described in Wang Y, et al, Trans body against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906 each incorporated by reference); inhibitors of HBx-interactions such as RNAi, antisense and nucleic acid based polymers targeting HBV RNA, e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BSI); Non-Interferon Immune enhancers such as Thymosin alpha-1 (Zadaxin) and Interleukin-7 (CYT107); TLR-7/9 agonists such as GS-9620, CYT003, Resiquimod; Cyclophilin Inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed compound, and administering another HBV capsid assembly promoter.

In some embodiments, the first and second amounts together comprise a pharmaceutically effective amount. The first amount, the second amount, or both may be the same, more, or less than effective amounts of each compound administered as monotherapies.

Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, e.g. a fluorophore moiety (such a moiety may for example re-emit a certain light frequency upon binding to a virus and/or upon photon excitation. Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

Example 1: Synthesis of 11-oxo-10, 11-dihydrodibenzo[b,f][1,4]thiazepine-8-carboxylic acid (9): A Common Intermediate

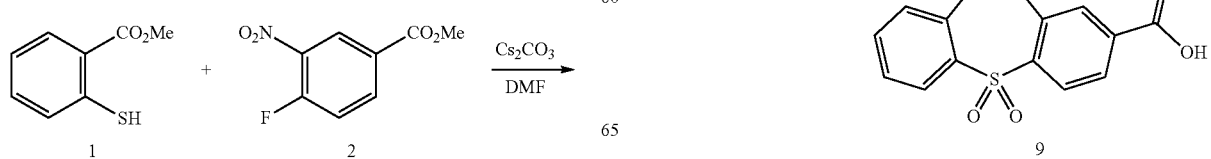

Synthesis of methyl 4-((2-(methoxycarbonyl)phenyl)thio)-3-nitrobenzoate (3)

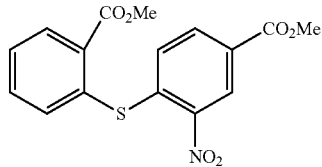

3

To a stirred solution of methyl 4-fluoro-3-nitrobenzoate 2 (30 g, 150.67 mmol) in DMF (300 mL) under inert atmosphere were added cesium carbonate (58.76 g, 180.8 mmol) and methyl 2-mercaptobenzoate 1 (22.6 mL, 165.47 mmol) at RT; heated to 55-60° C. and stirred for 2 h. The reaction was monitored by TLC; after completion of the reaction, the reaction mixture was diluted with water (1500 mL) and the precipitated solid was filtered to obtain the crude. The crude was washed with water (500 mL), hexane (200 mL) and dried in vacuo to afford compound 3 (48.8 g, 93%) as yellow solid. TLC: 20% EtOAc/hexanes ($R_f$: 0.4); $^1$H NMR (CDCl$_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H).

Synthesis of methyl 3-amino-4-((2-(methoxycarbonyl)phenyl)thio)benzoate (4)

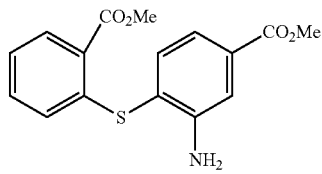

4

To a stirred solution of compound 3 (48 g, 138.32 mmol) in MeOH (1000 mL) under inert atmosphere was added 10% Pd/C (20 g, wet) at RT under hydrogen atmosphere in an autoclave (100 psi pressure) and stirred for 24 h. The reaction was monitored by TLC; after completion of the reaction, the reaction mixture was filtered through celite, washed with 50% MeOH/CH$_2$Cl$_2$ (500 mL). The filtrate was removed in vacuo to obtain the crude which as triturated with diethyl ether (200 mL), washed with hexane (200 mL) and dried in vacuo to afford compound 4 (40 g, 91%) as yellow solid. TLC: 10% EtOAc/hexanes ($R_f$: 0.3); $^1$H NMR (DMSO-d$_6$, 400 MHz): δ 7.95 (dd, J=7.8, 1.4 Hz, 1H), 7.48-7.35 (m, 3H), 7.23 (td, J=7.5, 1.1 Hz, 1H), 7.15 (dd, J=8.0, 1.8 Hz, 1H), 6.66 (dd, J=8.2, 0.8 Hz, 1H), 5.67 (br s, 2H), 3.88 (s, 3H), 3.84 (s, 3H).

Synthesis of 3-amino-4-((2-carboxyphenyl)thio)benzoic acid (5)

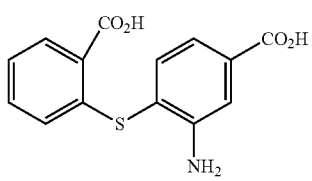

5

To a stirred solution of compound 4 (40 g, 126.18 mmol) in THF: H$_2$O (5: 1, 400 mL) was added lithium hydroxide monohydrate (26 g, 619.0 mmol) at 0° C.; warmed to RT and stirred for 48 h. The reaction was monitored by TLC; after completion of the reaction, the volatiles were removed in vacuo. The pH of the residue was acidified with 2 N HCl to ~2. The precipitated solid was filtered and dried in vacuo to afford compound 5 (34.6 g, 95%) as an off-white solid. TLC: 30% EtOAc/hexanes ($R_f$: 0.1); $^1$H NMR (DMSO-d$_6$, 500 MHz): δ 13.00 (br s, 2H), 7.93 (dd, J=7.7, 1.0 Hz, 1H), 7.42 (s, 1H), 7.40-7.31 (m, 2H), 7.18 (t, J=7.4 Hz, 1H), 7.13 (dd, J=8.0, 1.6 Hz, 1H), 6.61 (d, J=7.8 Hz, 1H), 5.55 (br s, 2H).

Synthesis of 11-oxo-10, 11-dihydrodibenzo[b,f][1,4]thiazepine-8-carboxylic acid (6)

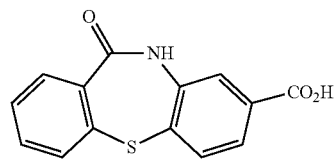

6

To a stirred solution of compound 5 (31 g, 107.26 mmol) in THF (600 mL) under inert atmosphere was added CDI (86.88 g, 536.29 mmol) at 0° C.; warmed to RT and stirred for 16 h. The reaction was monitored by TLC; after completion of the reaction, the reaction to mixture was acidified with 2 N HCl to pH-4. The obtained solid was filtered and further dried by using toluene (2×200 mL) to afford compound 6 (26 g, 90%) as white solid. TLC: 10% MeOH/CH$_2$Cl$_2$ ($R_f$: 0.3); $^1$H NMR (DMSO-d$_6$, 400 MHz): δ 13.22 (br s, 1H), 10.81 (s, 1H), 7.78 (s, 1H), 7.72-7.64 (m, 3H), 7.57-7.44 (m, 3H).

Synthesis of methyl 11-oxo-10,11-dihydrodibenzo[b,f][1,4]thiazepine-8-carboxylate (7)

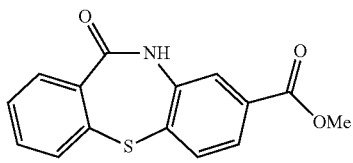

7

To a stirred solution of 6 (500 mg, 1.84 mmol) in MeOH: CH$_2$Cl$_2$ (1: 1, 20 mL) under argon atmosphere was added CH$_2$N$_2$ (in situ prepared using N-nitrosomethyl urea (0.95 g, 9.2 mmol)+KOH (0.51 g, 9.22 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 7 (450 mg, 86%) as white solid. TLC: 30% EtOAc/hexanes ($R_f$: 0.5); $^1$H-NMR (DMSO-d$_6$, 500 MHz): δ 10.82 (s, 1H), 7.82 (s, 1H), 7.75-7.69 (m, 3H), 7.58-7.63 (m, 3H), 3.82 (s, 3H).

19

Synthesis of methyl 11-oxo-10,11-dihydrodibenzo[b,f][1,4]thiazepine-8-carboxylate 5,5-dioxide (8)

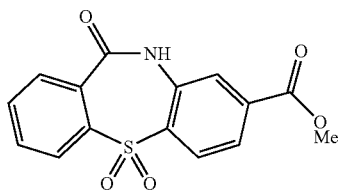

8

To a stirred solution of 7 (5 g, 17.54 mmol) in acetic acid (25 mL) was added 30% aqueous hydrogen peroxide (100 mL) at 0° C.; warmed to 50° C. and stirred for 72 h. The reaction was monitored by TLC; after completion of the reaction, the obtained solid was filtered, washed with water (100 mL), 10% EtOAc/hexanes (100 mL) and dried in vacuo to afford compound 8 (3.5 g, 64%) as white solid. TLC: 5% MeOH/$CH_2Cl_2$ ($R_f$: 0.3); $^1$H NMR (DMSO-$d_6$, 500 MHz): δ 11.58 (s, 1H), 8.09 (d, J=8.4 Hz, 1H), 8.01-7.95 (m, 3H), 7.93-7.83 (m, 3H), 3.88 (s, 3H);

Synthesis of 11-oxo-10,11-dihydrodibenzo[b,f][1,4]thiazepine-8-carboxylic acid 5,5-dioxide (9)

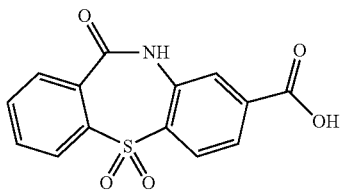

9

To a stirred solution of compound 8 (3.5 g, 11.04 mmol) in a mixture of THF:MeOH:$H_2O$ (2:2:1, 25 mL) was added lithium hydroxide monohydrate (1.3 g, 33.12 mmol) portion wise for 10 min at 0° C.; warmed to RT and stirred for 3 h. The reaction was monitored by TLC; after completion of the reaction, the volatiles were removed in vacuo. The residue was diluted with water (20 mL) and acidified with 1 N HCl to pH-2. The obtained solid was filtered, washed with isopropyl alcohol (15 mL) and dried in vacuo to obtain compound 9 (2.8 g, 84%) as white solid. TLC: 5% MeOH/$CH_2Cl_2$ ($R_f$: 0.1); $^1$H NMR (DMSO-$d_6$, 400 MHz): δ 13.65 (br s, 1H), 11.55 (s, 1H), 8.07 (d, J=8.3 Hz, 1H), 8.03-7.82 (m, 6H).

Example 2: Synthesis of 11-oxo-10,11-dihydrodibenzo[b,f][1,4]oxazepine-8-carboxylic acid (14): A Common Intermediate

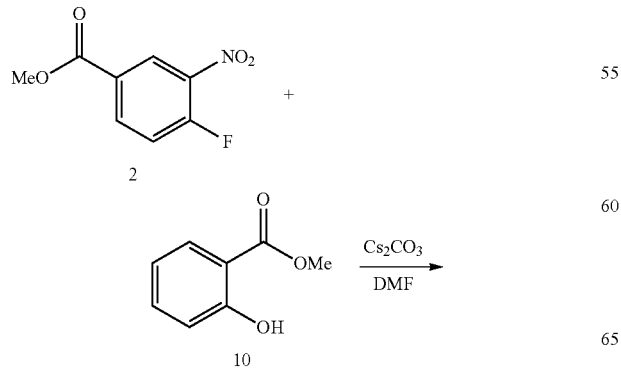

20

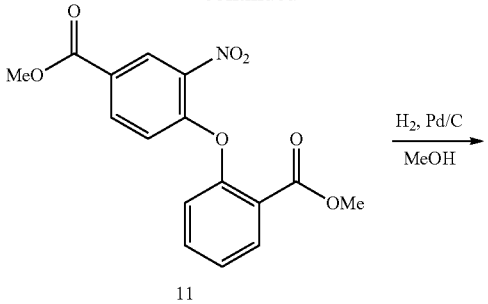

11

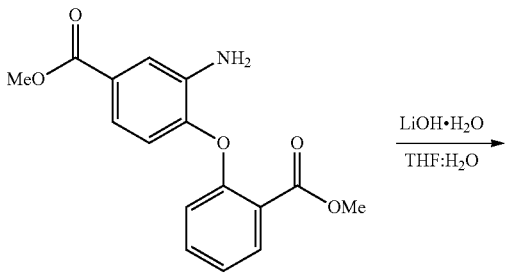

12

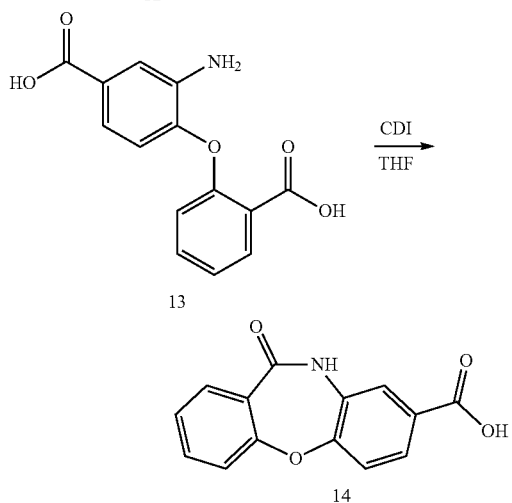

13

14

Synthesis of methyl 4-(2-(methoxycarbonyl)phenoxy)-3-nitrobenzoate (11)

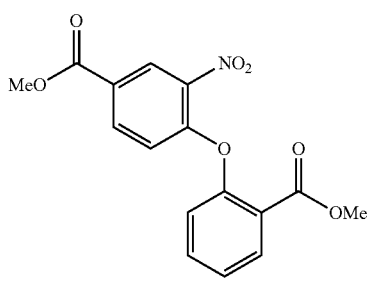

11

To a stirred solution of methyl 4-fluoro-3-nitrobenzoate 2 (5 g, 25.12 mmol) in DMF (75 mL) under argon atmosphere were added methyl 2-hydroxybenzoate 10 (4.2 g, 27.63 mmol), cesium carbonate (8.98 g, 27.64 mmol), at RT; heated to 100° C. and stirred for 2 h. The reaction was monitored by TLC; after completion of the reaction, the reaction mixture was diluted with ice-cold water (200 mL). The precipitated solid was filtered, washed with n-hexane (100 mL) and dried in vacuo to afford compound 11 (6.2 g, 75%) as an off-white solid. TLC: 30% EtOAc/hexanes ($R_f$: 0.4); $^1$H NMR (DMSO-$d_6$, 500 MHz): δ 8.54 (s, 1H), 8.11 (dd, J=8.8, 2.2 Hz, 1H), 8.02 (dd, J=7.7, 1.6 Hz, 1H), 7.80 (td, J=7.8, 1.7 Hz, 1H), 7.52 (t, J=7.4 Hz, 1H), 7.45 (d, J=7.8 Hz, 1H), 6.89 (d, J=8.7 Hz, 1H), 3.88 (s, 3H), 3.64 (s, 3H).

Synthesis of methyl 3-amino-4-(2-(methoxycarbonyl)phenoxy)benzoate (12)

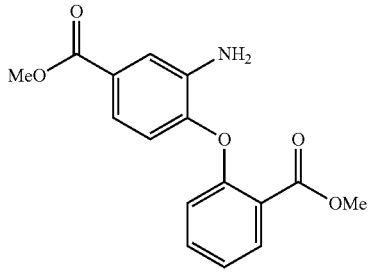

To a stirred solution of compound 11 (2 g, 6.04 mmol) in MeOH (50 mL) was evacuated for 5 min and added 10% Pd/C (1 g, 50% wet) under argon atmosphere at RT and stirred under hydrogen atmosphere (balloon pressure) at RT for 16 h. The reaction was monitored by TLC; after completion of the reaction, the reaction mixture was filtered through celite and washed with 20% MeOH/CH$_2$Cl$_2$ (200 mL). The filtrate was concentrated in vacuo to obtain the crude. The crude was purified by combiflash chromatography using 20% EtOAc/hexanes to afford compound 12 (1.4 g, 77%) as an off-white solid. TLC: 30% EtOAc/hexanes ($R_f$: 0.3); $^1$H NMR (DMSO-$d_6$, 400 MHz): δ 7.84 (dd, J=7.7, 1.6 Hz, 1H), 7.61-7.55 (m, 1H), 7.44 (s, 1H), 7.27 (t, J=7.2 Hz, 1H), 7.13 (dd, J=8.3, 2.0 Hz, 1H), 7.00 (d, J=8.0 Hz, 1H), 6.65 (d, J=8.3 Hz, 1H), 5.30 (br s, 2H), 3.80 (s, 3H), 3.74 (s, 3H).

Synthesis of 3-amino-4-(2-carboxyphenoxy)benzoic acid (13)

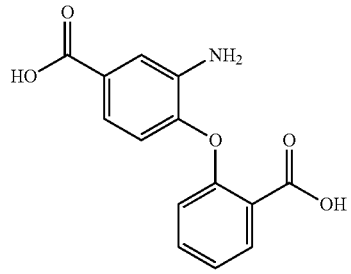

To a stirred solution of compound 12 (1.4 g, 4.65 mmol) in THF: H$_2$O (3:1, 40 mL) was added lithium hydroxide monohydrate (976 mg, 23.23 mmol) at RT; heated to reflux and stirred for 2 h. The reaction was monitored by TLC; after completion of the reaction, the volatiles were removed in vacuo. The pH of the residue was acidified to ~2 with 2 N HCl. The precipitated solid was filtered, washed with water (20 mL), n-pentane (20 mL) and dried in vacuo to afford compound 13 (700 mg, 56%) as an off-white solid. TLC: 30% EtOAc/hexanes ($R_f$: 0.1); $^1$H NMR (DMSO-$d_6$, 400 MHz): δ 7.86 (dd, J=7.7, 1.6 Hz, 1H), 7.63 (s, 1H), 7.62-7.57 (m, 1H), 7.37 (d, J=7.3 Hz, 1H), 7.31 (t, J=7.3 Hz, 1H), 7.06 (d, J=8.0 Hz, 1H), 6.69 (d, J=8.5 Hz, 1H).

Synthesis of 11-oxo-10,11-dihydrodibenzo[b, f][1,4]oxazepine-8-carboxylic acid (14)

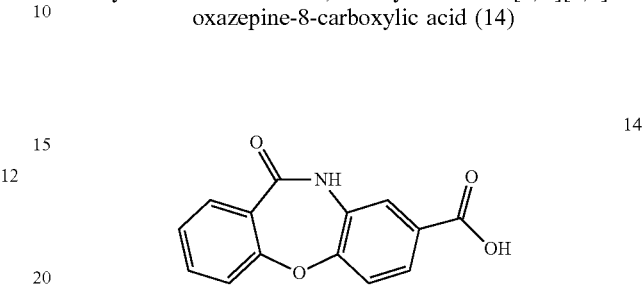

To a stirred solution of compound 13 (700 mg, 2.56 mmol) in THF (20 mL) under argon atmosphere was added CDI (2.07 g, 12.77 mmol) at RT and stirred for 24 h. The reaction was monitored by TLC; after completion of the reaction, the volatiles were removed in vacuo. The pH of the residue was acidified to ~2 using 2 N HCl. The precipitated solid was filtered, washed with n-pentane (50 mL) and dried in vacuo to afford compound 14 (450 mg, 69%) as an off-white solid. TLC: 10% MeOH/CH$_2$Cl$_2$ ($R_f$: 0.2); $^1$H NMR (DMSO-$d_6$, 400 MHz): δ 13.03 (br s, 1H), 10.65 (s, 1H), 7.81-7.76 (m, 2H), 7.70 (dd, J=8.4, 2.2 Hz, 1H), 7.67-7.61 (m, 1H), 7.43 (d, J=8.4 Hz, 1H), 7.40-7.31 (m, 2H).

Example 3: Synthesis of 11-oxo-10,11-dihydro-5H-dibenzo[b,e][1,4]diazepine-8-carboxylic acid (19): A Common Intermediate

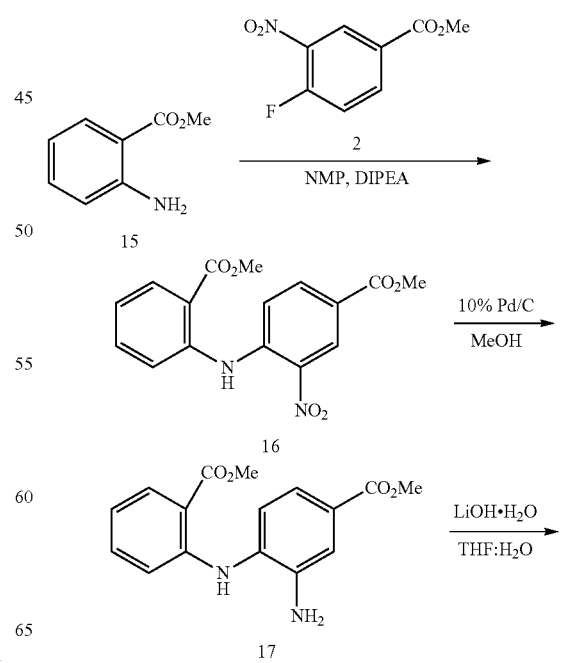

-continued

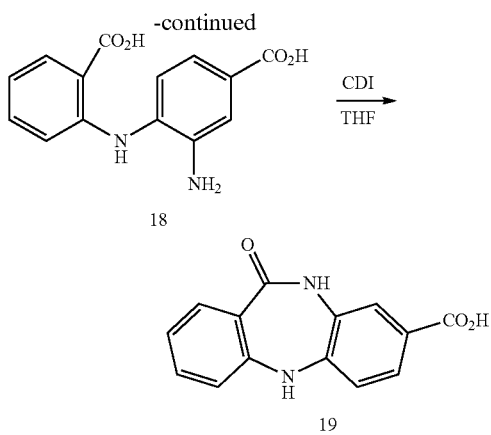

Synthesis of methyl 4-((2-(methoxycarbonyl)phenyl)amino)-3-nitrobenzoate (16)

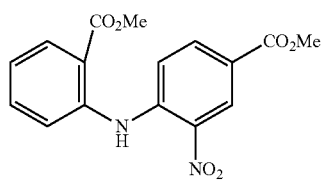

To a stirred solution of methyl 2-aminobenzoate 15 (5 g, 33.07 mmol) in N-Methyl-2-pyrrolidone (13 mL) under inert atmosphere were added diisopropylethylamine (18 mL, 103.46 mmol), methyl 4-fluoro-3-nitrobenzoate 2 (9.87 g, 49.21 mmol) at RT; heated to 120° C. in a sealed tube and stirred for 14 h. The reaction was monitored by TLC; after completion of the reaction, the reaction mixture was diluted with diethyl ether (100 mL) and stirred for 1 h. The obtained solid was filtered, washed with EtOAc (100 mL) and dried in vacuo to afford compound 16 (2.9 g, 26%) as yellow solid. TLC: 30% EtOAc/hexanes ($R_f$: 0.4); $^1$H NMR (DMSO-$d_6$, 400 MHz): δ 11.13 (s, 1H), 8.67 (s, 1H), 8.11-7.94 (m, 2H), 7.70-7.62 (m, 2H), to 7.58 (d, J=9.0 Hz, 1H), 7.32-7.27 (m, 1H), 3.87 (s, 6H).

Synthesis of methyl 3-amino-4-((2-(methoxycarbonyl)phenyl)amino)benzoate (17)

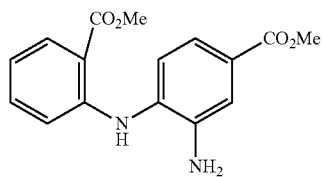

To a stirred solution of compound 16 (5 g, 15.15 mmol) in MeOH (150 mL) under inert atmosphere was added 10% Pd/C (2.5 g, 50% wet) at RT and stirred under hydrogen atmosphere (balloon pressure) at RT for 16 h. The reaction was monitored by TLC; after completion of the reaction, the reaction mixture was filtered through celite and washed with 20% MeOH/CH$_2$Cl$_2$ (600 mL). The filtrate was concentrated in vacuo to obtain the crude. The crude washed with diethyl ether: n-pentane (1: 2, 30 mL) dried in vacuo to afford compound 17 (2.7 g, 60%) as yellow solid. TLC: 30% EtOAc/hexanes ($R_f$: 0.3); $^1$H NMR (DMSO-$d_6$, 400 MHz): δ 8.92 (s, 1H), 7.91 (dd, J=8.0, 1.6 Hz, 1H), 7.46-7.45 (m, 1H), 7.43-7.36 (m, 1H), 7.21 (s, 2H), 6.95 (dd, J=8.5, 0.6 Hz, 1H), 6.83-6.77 (m, 1H), 5.18 (s, 2H), 3.85 (s, 3H), 3.80 (s, 3H).

Synthesis of 3-amino-4-((2-carboxyphenyl)amino)benzoic acid (18)

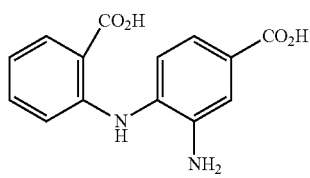

To a stirred solution of compound 17 (2.7 g, 9.00 mmol) in THF: H$_2$O (2.5: 1, 210 mL) was added lithium hydroxide monohydrate (3.4 g, 81.00 mmol) at RT; heated to 65° C. and stirred for 5 h. The reaction was monitored by TLC; after completion of the reaction, the volatiles were removed in vacuo. The pH of the residue was acidified to ~4 with 2 N HCl. The precipitated solid was filtered, washed with water (20 mL) and dried in vacuo to afford compound 18 (2.4 g, crude) as an off-white solid. TLC: 30% EtOAc/hexanes ($R_f$: 0.1); $^1$H NMR (DMSO-$d_6$, 400 MHz): δ 12.65 (br s, 2H), 9.20 (br s, 1H), 7.90 (dd, J=8.0, 1.6 Hz, 1H), 7.44-7.42 (m, 1H), 7.39-7.35 (m, 1H), 7.20-7.18 (m, 2H), 6.92 (dd, J=8.5, 0.7 Hz, 1H), 6.79-6.75 (m, 1H), 5.08 (br s, 2H).

Synthesis of 11-oxo-10,11-dihydro-5H-dibenzo[b,e][1,4]diazepine-8-carboxylic Acid (19)

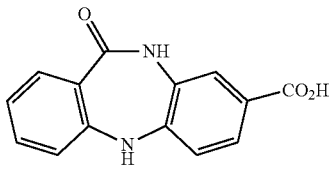

To a stirred solution of compound 18 (2.4 g, 8.82 mmol) in THF (80 mL) under inert atmosphere was added CDI (5.8 g, 35.29 mmol) at RT and stirred for 24 h. The reaction was monitored by TLC; after completion of the reaction, the volatiles were removed in vacuo. The pH of the residue was adjusted to ~2 using 2 N HCl. The precipitated solid was filtered, washed with n-pentane (50 mL) and dried in vacuo to afford compound 19 (1.9 g, 85%) as pale green solid. TLC: 10% MeOH/CH$_2$Cl$_2$ ($R_f$: 0.2); $^1$H NMR (DMSO-$d_6$, 400 MHz): δ 12.66 (br s, 1H), 9.93 (s, 1H), 8.26 (s, 1H), 7.70 (d, J=7.9 Hz, 1H), 7.58-7.50 (m, 2H), 7.36 (t, J=7.0 Hz, 1H), 7.02 (dd, J=17.4, 8.2 Hz, 2H), 6.91 (t, J=7.4 Hz, 1H).

Example 4: Synthesis of 5-methyl-11-oxo-10,11-dihydro-5H-dibenzo[b,e][1,4]diazepine-8-carboxylic acid (22): A Common Intermediate

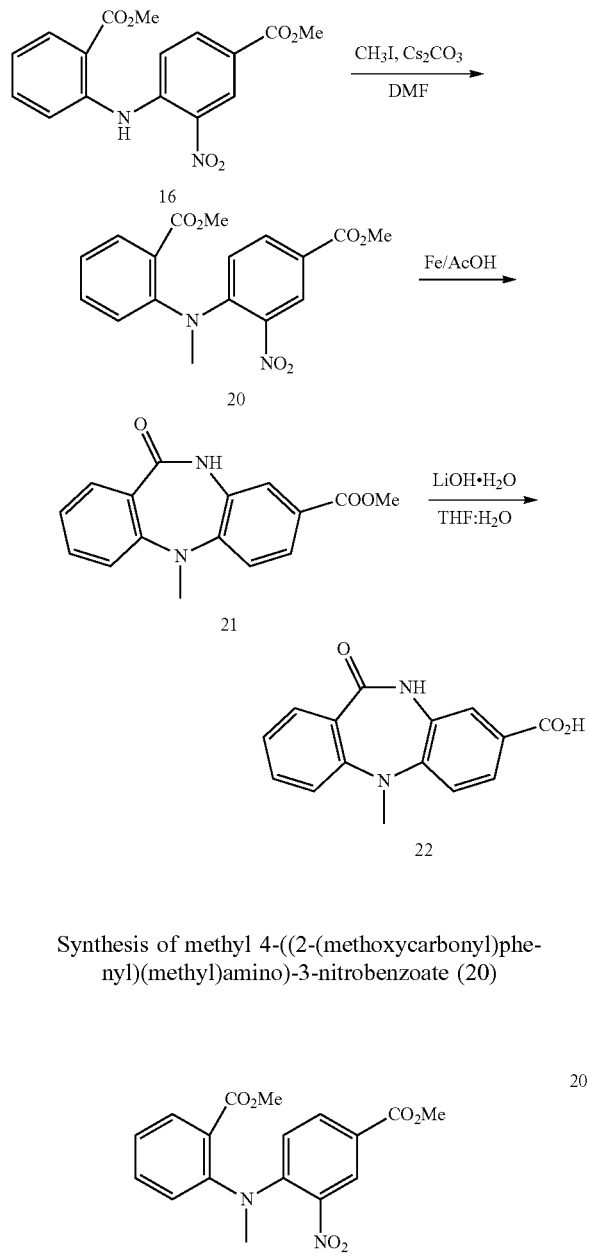

Synthesis of methyl 4-((2-(methoxycarbonyl)phenyl)(methyl)amino)-3-nitrobenzoate (20)

To a stirred solution of compound 16 (3 g, 9.09 mmol) in DMF (30 mL) under inert atmosphere were added cesium carbonate (5.9 g, 18.15 mmol), methyl iodide (0.84 mL, 13.59 mmol) at RT and stirred for 6 h. The reaction was monitored by TLC; after completion of the reaction, the reaction mixture was diluted with ice-cold water (60 mL) and extracted with EtOAc (2×100 mL). The combined organic extracts were dried over sodium sulfate, filtered and concentrated in vacuo to obtain the crude. The crude was purified through silica gel column chromatography using 20% EtOAc/hexanes to afford compound 20 (2.73 g, 88%) as yellow solid. TLC: 30% EtOAc/hexanes ($R_f$: 0.4); $^1$H NMR (DMSO-$d_6$, 400 MHz): δ 8.07 (s, 1H), 8.06 (d, J=7.8 Hz, 1H), 7.71 (dd, J=7.8, 1.5 Hz, 1H), 7.62 (t, J=7.3 Hz, 1H), 7.40-7.26 (m, 3H), 3.84 (s, 3H), 3.53 (s, 3H), 3.38 (s, 3H).

Synthesis of methyl 5-methyl-11-oxo-10,11-dihydro-5H-dibenzo[b,e][1,4]diazepine-8-carboxylate (21)

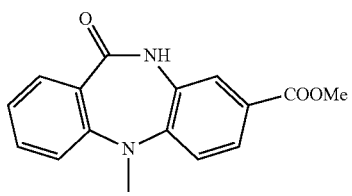

To a stirred solution of compound 20 (2.73 g, 7.93 mmol) in acetic acid (36 mL) under inert atmosphere was added iron powder (7 g, 127.2 mmol) at RT; heated to 80° C. and stirred for 4 h. The reaction was monitored by TLC; after completion of the reaction, the reaction mixture was diluted with CH$_2$Cl$_2$ (50 mL), stirred for 2 h and filtered through celite and the filtrate was concentrated in vacuo to obtain the crude. The crude was dissolved in to CH$_2$Cl$_2$ (200 mL), washed with saturated aqueous NaHCO$_3$ solution (100 mL), brine (100 mL).

The organic extract was dried over sodium sulfate, filtered and concentrated in vacuo to afford compound 21 (2 g, 91%) as an off-white solid. TLC: 30% EtOAc/hexanes ($R_f$: 0.4); $^1$H NMR (DMSO-$d_6$, 500 MHz): δ 10.33 (s, 1H), 7.68 (dd, J=8.5, 1.9 Hz, 1H), 7.65-7.61 (m, 2H), 7.50 (t, J=7.8 Hz, 1H), 7.28 (d, J=8.4 Hz, 1H), 7.21 (d, J=8.1 Hz, 1H), 7.10 (t, J=7.4 Hz, 1H), 3.80 (s, 3H), 3.33 (s, 3H).

Synthesis of 5-methyl-11-oxo-10,11-dihydro-5H-dibenzo[b,e][1,4]diazepine-8-carboxylic acid (22)

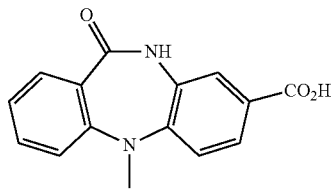

To a stirred solution of compound 21 (2 g, 7.09 mmol) in THF: H$_2$O (1: 1, 80 mL) was added lithium hydroxide monohydrate (900 mg, 21.42 mmol) at RT and stirred for 12 h. The reaction was monitored by TLC; after completion of the reaction, the volatiles were removed in vacuo. The pH of the residue was adjusted to ~2 with 2 N HCl. The precipitated solid was filtered and dried in vacuo to afford compound 22 (1.7 g, 89%) as an off-white solid. TLC: 40% EtOAc/hexanes ($R_f$: 0.2); $^1$H NMR (DMSO-$d_6$, 400 MHz): δ 12.82 (br s, 1H), 10.33 (s, 1H), 7.70-7.60 (m, 3H), 7.51 (t, J=7.8 Hz, 1H), 7.27 (d, J=8.5 Hz, 1H), 7.21 (d, J=7.8 Hz, 1H), 7.11 (t, J=7.2 Hz, 1H), 3.32 (s, 3H).

Example 5: Synthesis of 5-ethyl-11-oxo-10,11-dihydro-5H-dibenzo[b,e][1,4]diazepine-8-carboxylic acid (25): A Common Intermediate

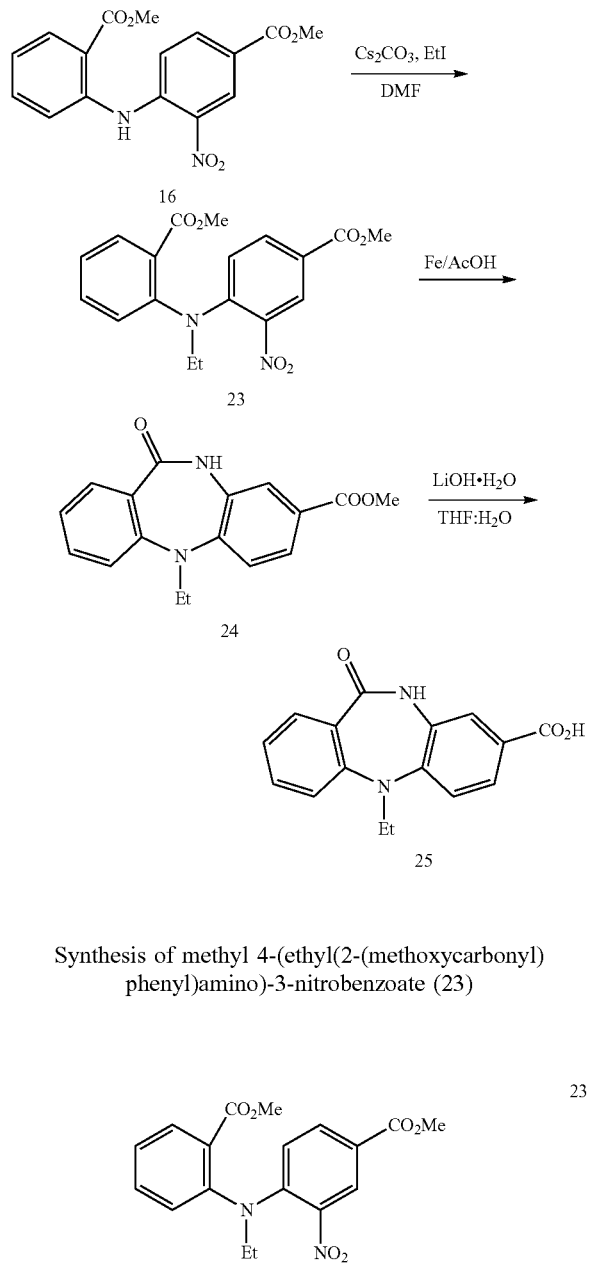

Synthesis of methyl 4-(ethyl(2-(methoxycarbonyl)phenyl)amino)-3-nitrobenzoate (23)

To a stirred solution of compound 16 (2.9 g, 8.78 mmol) in DMF (40 mL) under inert atmosphere were added cesium carbonate (6 g, 18.46 mmol), ethyl iodide (1.06 mL, 12.82 mmol) at RT and stirred for 5 h. The reaction was monitored by TLC; after completion of the reaction, the reaction mixture was diluted with ice-cold water (60 mL), extracted with EtOAc (2×100 mL). The combined organic extracts were dried over sodium sulfate, filtered and concentrated in vacuo to obtain the crude which was triturated with n-pentane (20 mL) to afford compound 23 (2.8 g, 89%) as pale yellow solid. TLC: 30% EtOAc/hexanes ($R_f$: 0.5); $^1$H NMR (DMSO-$d_6$, 500 MHz): δ 8.05 (dd, J=9.0, 2.0 Hz, 1H), 8.02 (s, 1H), 7.62-7.57 (m, 2H), 7.45 (d, J=9.0 Hz, 1H), 7.33 (d, J=8.1 Hz, 1H), 7.28 (t, J=7.5 Hz, 1H), 3.94 (q, J=7.1 Hz, 2H), 3.82 (s, 3H), 3.44 (s, 3H), 1.20 (t, J=7.1 Hz, 3H).

Synthesis of methyl 5-ethyl-11-oxo-10,11-dihydro-5H-dibenzo[b,e][1,4]diazepine-8-carboxylate (24)

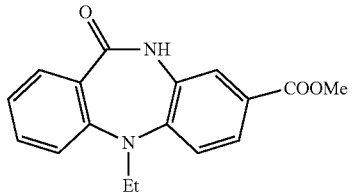

To a stirred solution of compound 23 (2.8 g, 7.82 mmol) in acetic acid (40 mL) under inert atmosphere was added iron powder (6.8 g, 125.1 mmol) at RT; heated to 80° C. and stirred for 4 h. The reaction was monitored by TLC; after completion of the reaction, the reaction mixture was diluted with CH$_2$Cl$_2$ (50 mL), stirred for 2 h and filtered through celite. The filtrate was concentrated in vacuo to obtain the crude. The crude was diluted with CH$_2$Cl$_2$ (200 mL), washed with saturated aqueous sodium bicarbonate solution (100 mL) and brine (100 mL). The organic extract was dried over sodium sulfate, filtered and concentrated in vacuo to afford compound 24 (2.2 g, 96%) as an off-white solid. TLC: 30% EtOAc/hexanes ($R_f$: 0.3); $^1$H NMR (DMSO-$d_6$, 500 MHz): δ 10.35 (br s, 1H), 7.70 (dd, J=8.5, 1.9 Hz, 1H), 7.67 (s, 1H), 7.62 (d, J=7.5 Hz, 1H), 7.51 (t, J=8.1 Hz, 1H), 7.29 (d, J=8.4 Hz, 1H), 7.22 (d, J=8.1 Hz, 1H), 7.12 (t, J=7.4 Hz, 1H), 3.31 (s, 5H), 1.11 (t, J=6.9 Hz, 3H).

Synthesis of 5-ethyl-11-oxo-10,11-dihydro-5H-dibenzo[b,e][1,4]diazepine-8-carboxylic acid (25)

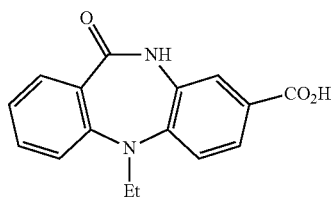

To a stirred solution of compound 24 (2.1 g, 7.09 mmol) in THF: H$_2$O (1: 1, 60 mL) was added lithium hydroxide monohydrate (890 mg, 21.26 mmol) at RT and stirred for 12 h. The reaction was monitored by TLC; after completion of the reaction, the volatiles were removed in vacuo. The pH of the residue was acidified to ~2 with 2 N HCl. The precipitated solid was filtered, washed with water (50 mL) and dried in vacuo to afford compound 25 (1.6 g, 80%) as an off-white solid. TLC: 30% EtOAc/hexanes ($R_f$: 0.2); $^1$H NMR (DMSO-$d_6$, 400 MHz): δ 12.82 (br s, 1H), 10.33 (s, 1H), 7.69-7.59 (m, 3H), 7.53-7.48 (m, 1H), 7.24 (dd, J=19.7, 8.2 Hz, 2H), 7.12 (t, J=7.5 Hz, 1H), 3.79 (br s, 2H), 1.12 (t, J=7.0 Hz, 3H).

Example 6: Commercial Available Amines

The following amines were obtained from commercial sources

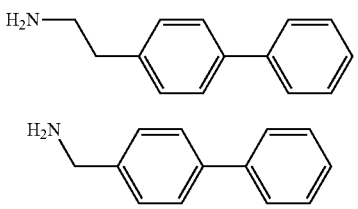

Preparation of amines for coupling reaction:

Example 7: Synthesis of 4-(2-aminoethyl)-N,N-dimethylbenzenesulfonamide hydrochloride (33)

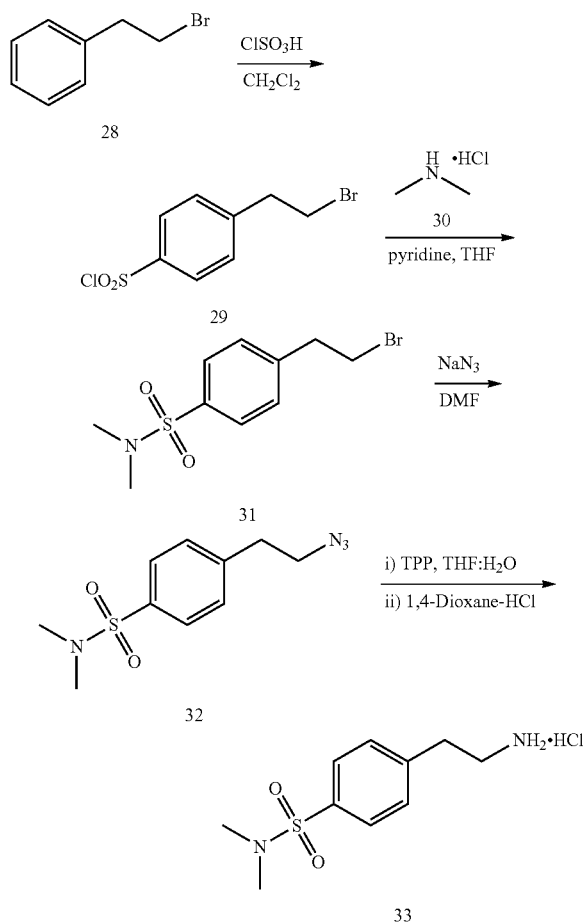

Synthesis of 4-(2-bromoethyl)benzenesulfonyl chloride (29)

To a stirred solution of (2-bromoethyl) benzene 28 (5 g, 27.02 mmol) in $CH_2Cl_2$ (15 mL) under argon atmosphere was added chlorosulfonic acid (5.4 mL, 81.08 mmol) at 0° C.; warmed to RT and stirred for 3 h. The reaction was monitored by TLC; after completion of the reaction, the reaction mixture was poured into ice-cold water (100 mL) extracted with $CH_2Cl_2$ (2×150 mL). The combined organic extracts were washed with brine (100 mL), separated dried over sodium sulfate, filtered and concentrated in vacuo to afford crude compound 29 (5 g) as colorless thick syrup. TLC: 10% EtOAc/hexanes ($R_f$: 0.6); $^1$H-NMR (DMSO-$d_6$, 400 MHz): δ 8.00 (d, J=8.4 Hz, 2H), 7.47 (d, J=8.8 Hz, 2H), 3.62 (t, J=7.2 Hz, 2H), 3.30 (t, J=7.2 Hz, 2H).

Synthesis of 4-(2-bromoethyl)-N,N-dimethylbenzenesulfonamide (31)

To a stirred solution of compound 29 (5 g, crude) in THF (100 mL) under argon atmosphere were added pyridine (14.37 mL, 176.05 mmol), dimethylamine hydrochloride 30 (7.1 g, 88.02 mmol) at 0° C.; warmed to RT and stirred for 1 h. The reaction was monitored by TLC; after completion the reaction, the volatiles were removed in vacuo. The residue was diluted with $CH_2Cl_2$ (500 mL) and washed with 1 N HCl (15 mL). The organic layer was dried over sodium sulfate, filtered and concentrated in vacuo to obtain crude. The crude was triturated with pentane (30 mL) and dried in vacuo to afford compound 31 (3.5 g, 68%) as an off-white solid. TLC: 20% EtOAc/hexane ($R_f$: 0.5); $^1$H NMR (CDCl$_3$, 400 MHz): δ 7.74 (d, J=8.4 Hz, 2H), 7.39 (d, J=8.5 Hz, 2H), 3.60 (t, J=7.2 Hz, 2H), 3.25 (t, J=7.3 Hz, 2H), 2.72 (s, 6H).

Synthesis of 4-(2-azidoethyl)-N,N-dimethylbenzenesulfonamide (32)

To a stirred solution of compound 31 (500 mg, 1.71 mmol) in DMF (10 mL) under inert atmosphere was added sodium azide (335 mg, 5.15 mmol) at RT and heated to 80° C. for 2 h. The reaction was monitored by TLC; after completion of the reaction, the reaction mixture was diluted with ice-cold water (20 mL) and extracted with $CH_2Cl_2$ (2×200 mL). The combined organic extracts were dried under sodium sulfate, filtered and concentrated in vacuo to afford compound 32 (350 mg, 80%) as thick syrup. TLC: 20% EtOAc/hexane ($R_f$: 0.6); $^1$H-NMR (DMSO-$d_6$, 400 MHz): δ 7.73 (d, J=8.4 Hz, 2H), 7.40 (d, J=6.8 Hz, 2H), 3.56 (t, J=6.8 Hz, 2H), 2.97 (t, J=6.8 Hz, 2H), 2.71 (s, 6H).

Synthesis of 4-(2-aminoethyl)-N,N-dimethylbenzenesulfonamide hydrochloride (33)

To a stirred solution of compound 32 (350 mg, 1.37 mmol) in a mixture of THF: $H_2O$ (4: 1, 10 mL) was added triphenyl phosphine (1.08 g, 4.13 mmol) at RT and stirred for 16 h. The reaction was monitored by TLC; after completion of the reaction, the volatiles were removed in vacuo to obtain the crude. The crude was purified through silica gel column chromatography using 3-5% MeOH/$CH_2Cl_2$ to afford free amine (200 mg) as thick syrup.

To a stirred solution of the free amine (200 mg) in $CH_2Cl_2$ (2 mL) under argon atmosphere was added 4 N HCl in 1,4-dioxane (0.5 mL) at 0° C. and stirred for 10 min. The volatiles were removed in vacuo to obtain the crude which was washed with diethyl ether (2×5 mL) and dried in vacuo to afford compound 33 (125 mg, 35%) as white solid. TLC: 10% to MeOH/$CH_2Cl_2$ ($R_f$: 0.2); $^1$H-NMR (DMSO-$d_6$, 400 MHz): δ 8.04 (br s, 2H), 7.70 (d, J=8.4 Hz, 2H), 7.54 (d, J=8.4 Hz, 2H), 3.15-3.05 (m, 2H), 3.01-2.98 (m, 2H), 2.60 (s, 6H).

Example 8: Synthesis of 2-(4-fluorophenoxy)ethan-1-amine hydrochloride (37)

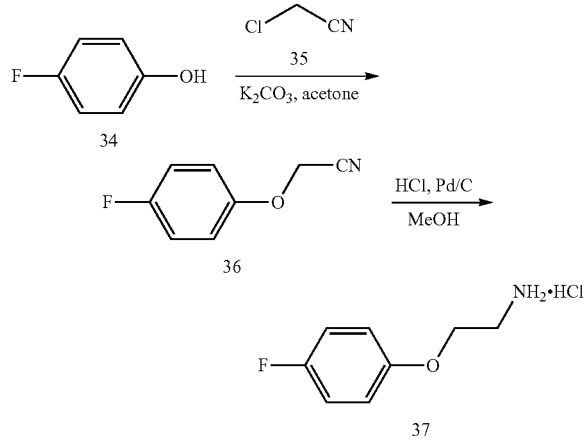

Synthesis of 2-(4-fluorophenoxy)acetonitrile (36)

To a stirred solution of 4-fluorophenol 34 (1.74 mL, 18.96 mmol) in acetone (50 mL) under argon atmosphere were added potassium carbonate (6.5 g, 47.40 mmol), chloroacetonitrile 35 (1 mL, 15.80 mmol) at RT; heated to reflux and stirred for 16 h. The reaction was monitored by TLC; after completion of the reaction, the reaction mixture was filtered and the filtrate was concentrated in vacuo. The residue was extracted with diethyl ether (3×40 mL). The combined organic extracts were washed with NaOH solution (30 mL), water (30 mL), dried over sodium sulfate, filtered and concentrated in vacuo to afford compound 36 (2.4 g, 90%) as brown syrup. TLC: 10% EtOAc/hexanes ($R_f$: 0.3); $^1$H-NMR (CDCl$_3$, 400 MHz): δ 7.06-7.01 (m, 2H), 6.98-6.89 (m, 2H), 4.73 (s, 2H).

Synthesis of 2-(4-fluorophenoxy)ethan-1-amine hydrochloride (37)

To a stirred solution of compound 36 (200 mg, 1.32 mmol) in MeOH (10 mL) under argon atmosphere were added HCl (0.3 mL), Pd/C (90 mg) and stirred under hydrogen atmosphere (balloon pressure) at RT and stirred for 16 h. The reaction was monitored by TLC; after completion of the reaction, the reaction mixture was diluted with saturated sodium potassium tartrate solution (20 mL) and extracted with diethyl ether (2×20 mL). The combined organic extracts were dried over sodium sulfate, filtered and concentrated in vacuo to afford compound 37 (130 mg, 65%) as an off-white solid. TLC: 10% EtOAc/hexanes ($R_f$: 0.2); $^1$H-NMR (DMSO-d$_6$, 400 MHz): δ 8.31-8.28 (m, 2H), 7.17-7.12 (m, 2H), 7.02-6.98 (m, 2H), 4.16 (t, J=5.2 Hz, 2H), 3.17 (t, J=5.2 Hz, 2H).

Example 9: Synthesis of benzyl (4-(4-(2-aminoethyl)phenoxy)butyl)carbamate hydrochloride (44)

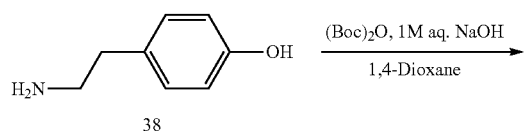

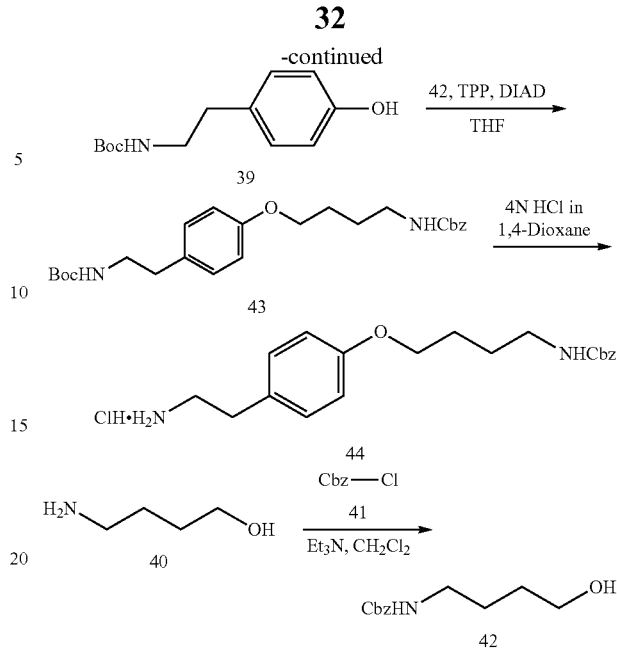

Synthesis of tert-butyl (4-hydroxyphenethyl)carbamate (39)

To a stirred solution of 4-(2-aminoethyl)phenol 38 (1 g, 7.29 mmol) in 1,4-dioxane: H$_2$O (1:1, 30 mL) were added 2 M aqueous sodium hydroxide solution (2 mL) and Boc-anhydride (1.9 mL, 8.25 mmol) at 0° C.; warmed to RT and stirred for 3 h. The reaction was monitored by TLC; after completion of the reaction, the pH of the reaction mixture cooled to 0° C., acidified with 1 M HCl to ~3 and extracted with EtOAc (2×50 mL). The combined organic extracts were dried over sodium sulphate, filtered and concentrated in vacuo to afford compound 39 (1.5 g, 87%) as an off-white solid. TLC: 50% EtOAc/hexanes ($R_f$: 0.8); $^1$H NMR (DMSO-d$_6$, 500 MHz): δ 9.15 (s, 1H), 6.95 (d, J=8.4 Hz, 2H), 6.83 (t, J=5.4 Hz, 1H), 6.64 (d, J=8.1 Hz, 2H), 3.09-3.00 (m, 2H), 2.56-2.51 (m, 2H), 1.35 (s, 9H).

Synthesis of benzyl (4-hydroxybutyl) carbamate (42)

To a stirred solution of 4-aminobutan-1-ol 40 (1.0 g, 11.23 mmol) in CH$_2$Cl$_2$ (15 mL) under argon atmosphere were added triethyl amine (1.78 mL, 12.35 mmol) and benzyl chloroformate 41 (1.76 mL, 12.35 mmol, 50% solution in toluene) at 0° C.; warmed to RT and stirred for 6 h. The reaction was monitored by TLC; after completion of the reaction, the reaction mixture was diluted with saturated ammonium chloride (50 mL) at 0° C. The organic layer was washed with brine (50 mL), dried over sodium sulfate, filtered and concentrated in vacuo to afford compound 42 (2.1 g, 84%) as colorless liquid. TLC: 50% EtOAc/hexanes ($R_f$: 0.5); $^1$H NMR (DMSO-d$_6$, 500 MHz): δ 7.40-7.22 (m, 6H), 4.98 (s, 2H), 4.37 (t, J=5.1 Hz, 1H), 3.36 (q, J=5.8 Hz, 2H), 2.97 (q, J=6.3 Hz, 2H), 1.51-1.28 (m, 4H).

Synthesis of tert-butyl (4-(4-(((benzyloxy)carbonyl)amino)butoxy)phenethyl)carbamate (43)

To a stirred solution of compound 39 (1.5 g, 6.32 mmol) and compound 42 (1.4 g, 6.32 mmol) in THF (50 mL) under argon atmosphere at 0° C. were added triphenyl phosphine (1.65 g, 6.32 mmol), diisopropyl azodicarboxylate (1.4 mL, 6.96 mmol) at 0° C.; warmed to RT and stirred for 2 h. The reaction was monitored by TLC; after completion of the reaction, the volatiles were removed in vacuo to obtain the crude. The crude was dissolved in 10% EtOAc/hexanes (5 mL) and the precipitated solid was filtered, washed with hexane (20 mL), dried in vacuo to afford compound 43 (1.9 g, 68%) as an off-white solid. TLC: 5% MeOH/CH$_2$Cl$_2$ (R$_f$: 0.7); $^1$H NMR (DMSO-d$_6$, 500 MHz): δ 8.89 (s, 1H), 7.68-7.51 (m, 5H), 7.40-7.24 (m, 2H), 7.07 (d, J=8.4 Hz, 1H), 6.88-6.78 (m, 2H), 5.00 (s, 2H), 4.80-4.73 (m, 2H), 3.91 (t, J=6.4 Hz, 2H), 3.11-3.02 (m, 2H), 2.60 (t, J=7.5 Hz, 2H), 1.72-1.64 (m, 2H), 1.56-1.52 (m, 2H), 1.18 (d, J=6.1 Hz, 9H).

Synthesis of benzyl (4-(4-(2-aminoethyl)phenoxy)butyl)carbamate hydrochloride (44)

To a stirred solution of compound 43 (500 mg, 1.13 mmol) in CH$_2$Cl$_2$ (5 mL) was added 4 N HCl in 1,4-dioxane (3 mL) under argon atmosphere at 0-5° C.; warmed to RT and stirred for 3 h. The reaction was monitored by TLC; after completion of the reaction, the volatiles were removed under reduced pressure. The obtained solid was washed with diethyl ether (10 mL), n-pentane (10 mL) and dried in vacuo to afford compound 44 (200 mg, 47%) as white solid. TLC: 5% MeOH/CH$_2$Cl$_2$ (R$_f$: 0.4); $^1$H NMR (DMSO-d$_6$, 500 MHz): δ 7.88 (br s, 3H), 7.39-7.28 (m, 5H), 7.15 (d, J=8.7 Hz, 2H), 6.88 (d, J=8.7 Hz, 2H), 5.00 (s, 2H), 3.93 (t, J=6.4 Hz, 2H), 3.04 (q, J=6.7 Hz, 2H), 2.97 (d, J=6.4 Hz, 2H), 2.81-2.76 (m, 2H), 1.73-1.65 (m, 2H), 1.57-1.51 (m, 2H).

Example 10: Synthesis of 2-phenylbutan-1-amine hydrochloride (47)

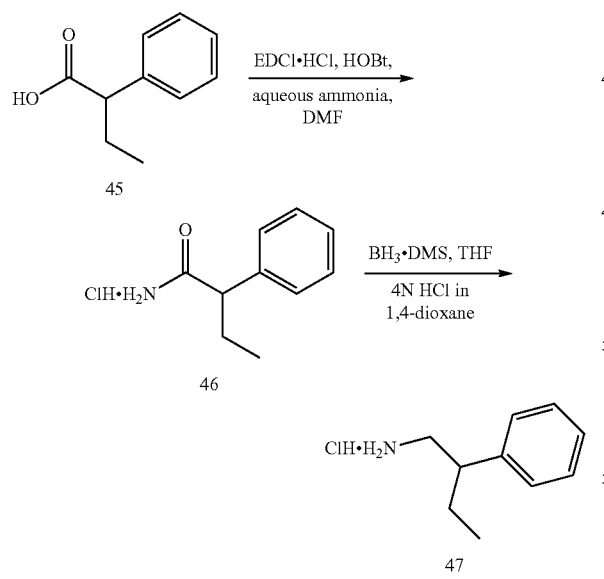

Synthesis of 2-phenylbutanamide hydrochloride (46)

To a stirred solution of 2-phenylbutanoic acid 45 (5 g, 30.48 mmol) in DMF (50 mL) under inert atmosphere were added HOBt (4.44 g, 32.92 mmol), EDCI.HCl (6.90 g, 35.97 mmol) at 0° C. added aqueous ammonia (100 mL), warmed to RT and stirred for 16 h. The reaction was monitored by TLC; after completion of the reaction, the reaction mixture was diluted with water (20 mL) and extracted with EtOAc (2×100 mL). The combined organic extracts were dried over sodium sulfate, filtered and concentrated in vacuo to obtain the compound 46 (2.5 g, 50%) as an off-white solid. TLC: 40% EtOAc/hexanes (R$_f$: 0.7). $^1$H-NMR (CDCl$_3$, 400 MHz): δ 7.39-7.16 (m, 5H), 5.38 (br s, 2H), 3.29 (t, J=7.6 Hz, 1H), 2.24-2.12 (m, 1H), 1.86-1.73 (m, 1H), 0.89 (t, J=7.4 Hz, 3H).

Synthesis of 2-phenylbutan-1-amine hydrochloride (47)

To a stirred solution of compound 46 (2 g, 1.2 mmol) in THF (50 mL) under inert atmosphere was added borane dimethyl sulfide complex (4.9 mL, 2.40 mmol, 5.0 M solution in THF) dropwise for 15 min at 0° C. and warmed to RT and stirred for 15 min. The reaction mixture was heated to reflux and stirred for 12 h. The reaction was monitored by TLC; after completion of the reaction, the reaction mixture was quenched with MeOH (5 mL) and the pH was adjusted to ~2 using 1 N HCl. The solvent was removed in vacuo. The pH of the residue was basified using saturated NaHCO$_3$ solution and extracted with EtOAc (2×50 mL). The combined organic extracts were dried over sodium sulfate, filtered and concentrated in vacuo to obtain the crude.

To the above crude compound in CH$_2$Cl$_2$ (50 mL) under inert atmosphere was added 4 N HCl in 1,4-dioxane (20 mL) at 0° C.; warmed to RT and stirred for 4 h. The reaction was monitored by TLC; after completion of the reaction, the volatiles were removed in vacuo to obtain the crude which was washed with MeOH (2×5 mL) and dried in vacuo to afford compound 47 (600 mg, 26%). TLC: 30% EtOAc/hexanes (R$_f$: 0.2). $^1$H-NMR (DMSO-d$_6$, 500 MHz): δ 7.96 (br s, 3H), 7.36-7.32 (m, 2H), 7.28-7.23 (m, 3H), 3.07-3.00 (m, 1H), 2.99-2.91 (m, 1H), 2.81-2.74 (m, 1H), 1.82-1.71 (m, 1H), 1.55-1.43 (m, 1H), 0.67 (t, J=7.2 Hz, 3H).

Example 11: Synthesis of 2-phenyl-2-(pyrrolidin-1-yl)ethan-1-amine hydrochloride (51)

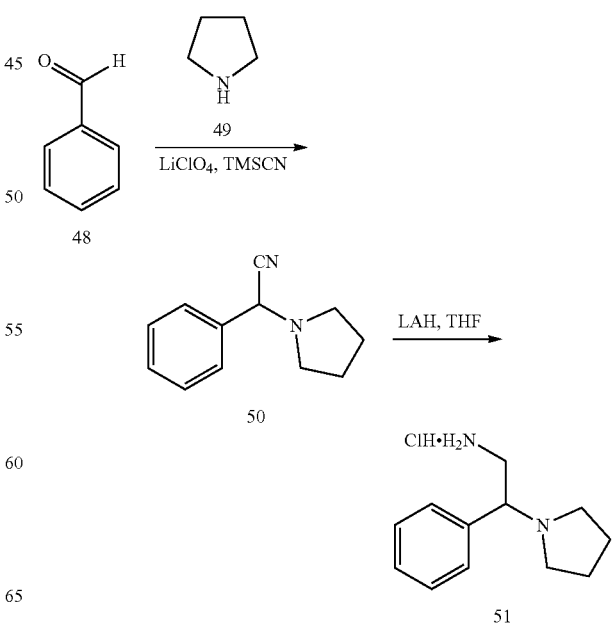

Synthesis of 2-phenyl-2-(pyrrolidin-1-yl)acetonitrile (50)

To a stirred solution of pyrrolidine 49 (0.78 mL, 9.42 mmol) in $CH_2Cl_2$ (10 mL) under inert atmosphere were added benzaldehyde 48 (1 g, 9.42 mmol), lithium perchlorate (1 g, 9.42 mmol) at RT and stirred for 10 min; added trimethylsilylcyanide (1.4 mL, 11.3 mmol) in $CH_2Cl_2$ (5 mL) and stirred for 2 h. The reaction was monitored by TLC; after completion of the reaction, the reaction mixture diluted with water (20 mL) and extracted with $CH_2Cl_2$ (2×30 mL). The combined organic extracts were dried over sodium sulphate, filtered and concentrated in vacuo to obtain the crude. The crude was purified through silica gel column chromatography using 20% EtOAc/hexanes to afford compound 50 (900 mg, 51%) as colorless syrup. TLC: 20% EtOAc/hexanes ($R_f$: 0.5); $^1$H-NMR (CDCl$_3$, 400 MHz): δ 7.60-7.51 (m, 2H), 7.49-7.35 (m, 3H), 5.05 (s, 1H), 2.75-2.56 (m, 4H), 1.90-1.72 (m, 4H).

Synthesis of 2-phenyl-2-(pyrrolidin-1-yl) ethan-1-amine hydrochloride (51)

To a stirred solution of compound 50 (1 g, 5.37 mmol) in THF (10 mL) under inert atmosphere was added lithium aluminium hydride (306 mg, 8.05 mmol) at 0° C.; warmed to RT and stirred for 3 h. The reaction was monitored by TLC; after completion of the reaction, the reaction mixture was quenched with water (5 mL), filtered, washed with EtOAc (5 mL) and the filtrate was concentrated in vacuo to obtain the crude. The crude further dried by using toluene (2×5 mL) to afford compound 51 (700 mg, 70%) as colorless syrup. TLC:10% MeOH/EtOAc ($R_f$: 0.2); $^1$H-NMR (DMSO-d$_6$, 500 MHz): δ 7.34-7.23 (m, 5H), 3.10-3.08 (m, 1H), 2.96 (dd, J=12.5, 4.5 Hz, 1H), 2.79-2.75 (m, 1H), 2.45-2.44 (m, 2H), 2.31-2.30 (m, 2H), 1.75-1.64 (m, 4H).

Example 12: Synthesis of 3-phenyl-3-(pyrrolidin-1-yl)propan-1-amine (54)

Synthesis of 3-phenyl-3-(pyrrolidin-1-yl)propanenitrile (53)

To a stirred solution of cinnamonitrile 52 (500 mg, 3.87 mmol) in $H_2O$ (15 mL) were added pyrrolidine 49 (412 mg, 5.80 mmol), ceric ammonium nitrate (2.1 g, 3.87 mmol) at RT, heated to 60° C. and stirred for 4 h. The reaction was monitored by TLC; after completion of the reaction, the reaction mixture was diluted with water (20 mL) and extracted with EtOAc (2×30 mL). The combined organic extracts were dried over sodium sulphate, filtered and concentrated in vacuo to obtain the crude. The crude was purified through silica gel column chromatography using 25% EtOAc/hexanes to afford compound 53 (300 mg, 39%) as colorless syrup. TLC: 30% EtOAc/hexanes ($R_f$: 0.5); $^1$H-NMR (CDCl$_3$, 400 MHz): δ 7.39-7.31 (m, 5H), 3.50-3.35 (m, 1H), 2.80-2.70 (m, 2H), 2.60-2.45 (m, 4H), 1.89-1.72 (m, 4H).

Synthesis of 3-phenyl-3-(pyrrolidin-1-yl)propan-1-amine (54)

To a stirred solution of compound 53 (150 mg, 0.75 mmol) in THF (10 mL) under argon atmosphere were added lithium aluminium hydride (57 mg, 1.50 mmol), $H_2SO_4$ (0.04 mL, 0.75 mmol) at 0° C.; warmed to RT and stirred for 5 h. The reaction was monitored by TLC; after completion of the reaction, the reaction mixture was quenched with saturated sodium sulphate and the reaction mixture was filtered through celite, washed with EtOAc (2×5 mL).The volatiles were removed in vacuo to afford compound 54 (100 mg, 65%) as an off-white solid. TLC: 10% MeOH/EtOAc ($R_f$: 0.3); $^1$H-NMR (CDCl$_3$, 400 MHz): δ 7.31-7.30 (m, 5H), 3.26-3.22 (m, 1H), 2.59-2.40 (m, 4H), 2.39-2.37 (m, 2H), 2.14-2.10 (m, 1H), 2.10-2.04 (m, 1H), 1.98-1.72 (m, 6H).

Example 13: Synthesis of (3-(2H-1,2,3-triazol-2-yl)phenyl)methanamine hydrochloride (58)

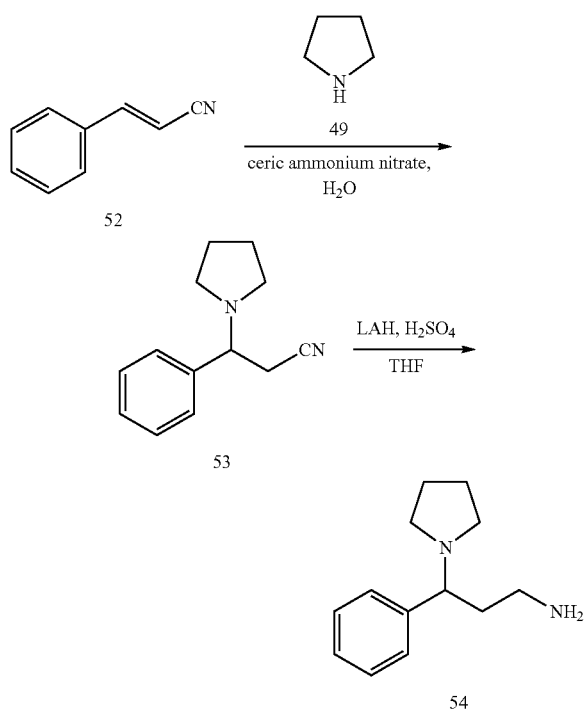

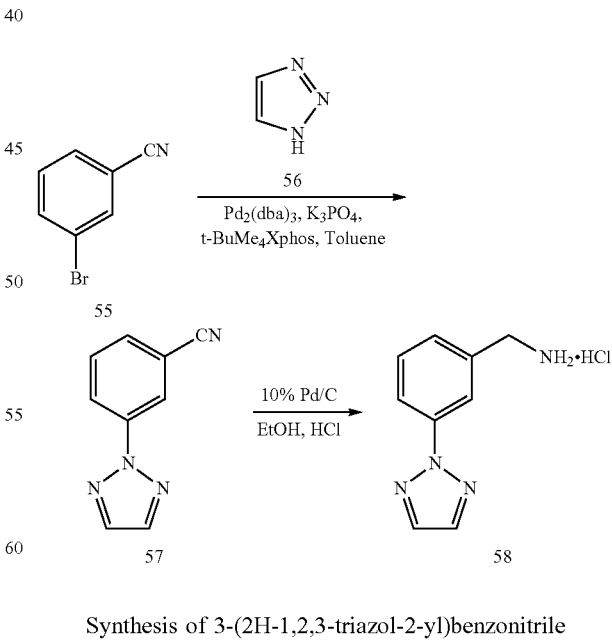

Synthesis of 3-(2H-1,2,3-triazol-2-yl)benzonitrile (57)

To a stirred solution of Pd$_2$(dba)$_3$ (126 mg, 0.13 mmol) in toluene (50 mL) under inert atmosphere was added t-BuMe₄Xphos (132 mg, 0.27 mmol) at RT and stirred for 10 min; heated to 120° C. for 3 min. This was added to a solution of 3-bromobenzonitrile 55 (1 g, 5.49 mmol), 1H-1,2,3-triazole 56 (454 mg, 6.59 mmol) and potassium phosphate (2.3 g, 10.98 mmol) in a sealed tube at RT and purged under argon for 30 min and heated to 110-120° C. and stirred for 6 h. The reaction was monitored by TLC; after completion of the reaction, the reaction mass was filtered through celite, washed with EtOAc (3×35 mL) and the filtrate was concentrated in vacuo to obtain the crude. The crude was purified through silica gel column chromatography using 10% EtOAc/hexanes to afford compound 57 (400 mg, 43%) as white solid. TLC: 10% EtOAc/hexanes ($R_f$: 0.3); ¹H-NMR (CDCl₃, 400 MHz): δ 8.43-8.41 (m, 1H), 8.35 (dt, J=7.5, 2.0 Hz, 1H), 7.86 (s, 2H), 7.66-7.58 (m, 2H).

Synthesis of (3-(2H-1,2,3-triazol-2-yl)phenyl)methanamine hydrochloride (58)

To a stirred solution of compound 57 (100 mg, 0.58 mmol) in EtOH (10 mL) under inert atmosphere was added 10% Pd/C (15 mg, wet) and concentrated HCl (0.298 mL, 5.02 mmol) at RT under hydrogen atmosphere (balloon pressure) and stirred for 4 h. The reaction was monitored by TLC; after completion of the reaction, the reaction mixture was filtered through celite. The filtrate was removed in vacuo to obtain the crude which washed with diethyl ether (20 mL) and dried in vacuo to afford compound 58 (75 mg, 61%) as white solid. TLC: 10% MeOH/CH₂Cl₂ ($R_f$: 0.2); ¹H NMR (DMSO-d₆, 400 MHz): δ 8.48 (br s, 3H), 8.22-8.19 (m, 1H), 8.16 (s, 2H), 8.05-8.01 (m, 1H), 7.64-7.60 (m, 1H), 7.57-7.53 (m, 1H), 4.15 (br s, 2H).

Example 14: Synthesis of (4-(2H-1,2,3-triazol-2-yl)phenyl)methanamine (62)

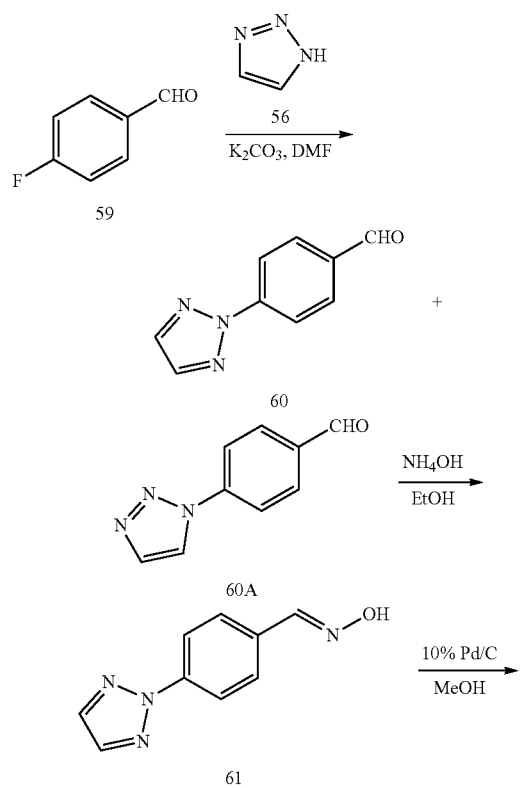

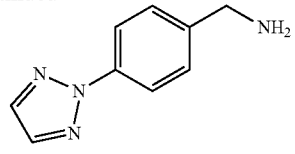

62

Synthesis of 4-(2H-1,2,3-triazol-2-yl)benzaldehyde & 4-(1H-1,2,3-triazol-1-yl) to benzaldehyde (60 & 60A)

To a stirred solution of 4-fluorobenzaldehyde 58 (5 g, 40.32 mmol) in DMF (150 mL) under inert atmosphere were added 1H-1,2,3-triazole 56 (3.3 g, 48.38 mmol), potassium carbonate (8.3 g, 60.48 mmol) at RT; heated to 100° C. and stirred for 16 h. The reaction was monitored by TLC; after completion of the reaction, the reaction mixture was diluted with ice cold water (35 mL) and extracted with EtOAc (2×40 mL). The combined organic extracts were dried over sodium sulfate, filtered and concentrated in vacuo to obtain the crude. The crude was purified through silica gel column chromatography using 20% EtOAc/hexanes to afford compound 60 (800 mg, 29%) and using 40% EtOAc/hexanes to afford compound 60A (1 g, 36%) as yellow solids.

Compound 60 analytical data:
TLC: 20% EtOAc/hexanes ($R_f$: 0.8); ¹H-NMR (DMSO-d₆, 400 MHz): δ 10.05 (s, 1H), 8.25 (d, J=10.0 Hz, 4H), 8.11 (d, J=8.8 Hz, 2H).

Compound 60A analytical data:
TLC: 20% EtOAc/hexanes ($R_f$: 0.3); ¹H-NMR (DMSO-d₆, 400 MHz): δ 10.07 (s, 1H), 8.98 (s, 1H), 8.19 (d, J=8.8 Hz, 2H), 8.13 (d, J=8.8 Hz, 2H), 8.04 (s, 1H).

Synthesis of 4-(2H-1,2,3-triazol-2-yl)benzaldehyde oxime (61)

To a stirred solution of compound 60 (200 mg, 1.15 mmol) in EtOH (5 mL) was added 50% aqueous ammonium hydroxide (0.38 mL, 5.78 mmol) at RT; heated to 90° C. and stirred for 2 h. The reaction was monitored by TLC; after completion of the reaction, the volatiles were removed in vacuo and diluted with water (100 mL) and extracted with EtOAc (2×100 mL). The combined organic extracts were dried over sodium sulfate, filtered and concentrated in vacuo to obtain the crude which was triturated with 10% EtOAc/hexanes (2×10 mL) and dried in vacuo to afford compound 61 (175 mg, 81%) as white solid. TLC: 30% EtOAc/hexanes ($R_f$: 0.3); ¹H-NMR (DMSO-d₆, 400 MHz): δ 11.37 (s, 1H), 8.21 (s, 1H), 8.15 (s, 2H), 8.06 (d, J=8.7 Hz, 2H), 7.78 (d, J=8.8 Hz, 2H).

Synthesis of (4-(2H-1,2,3-triazol-2-yl)phenyl)methanamine (62)

To a stirred solution of compound 61 (175 mg, 0.93 mmol) in MeOH (10 mL) under inert atmosphere were added 10% Pd/C (50 mg), at RT and stirred under hydrogen atmosphere (balloon pressure) for 6 h. The reaction was monitored by TLC; after completion of the reaction, the reaction mixture was filtered through celite and the filtrate was concentrated in vacuo to obtain the crude. The crude was purified through silica gel column chromatography using 10% MeOH/CH₂Cl₂ to afford compound 62 (45 mg, 28%) as white solid. TLC: 10% MeOH/CH₂Cl₂ ($R_f$: 0.2);

$^1$H-NMR (DMSO-d$_6$, 400 MHz): δ 8.12 (s, 2H), 8.01 (d, J=8.6 Hz, 2H), 7.58 (d, J=8.7 Hz, 2H), 5.64 (br s, 2H), 3.93 (s, 2H).

Example 15: Synthesis of (4-(1-benzyl-1H-1,2,3-triazol-5-yl)phenyl)methanamine (70)

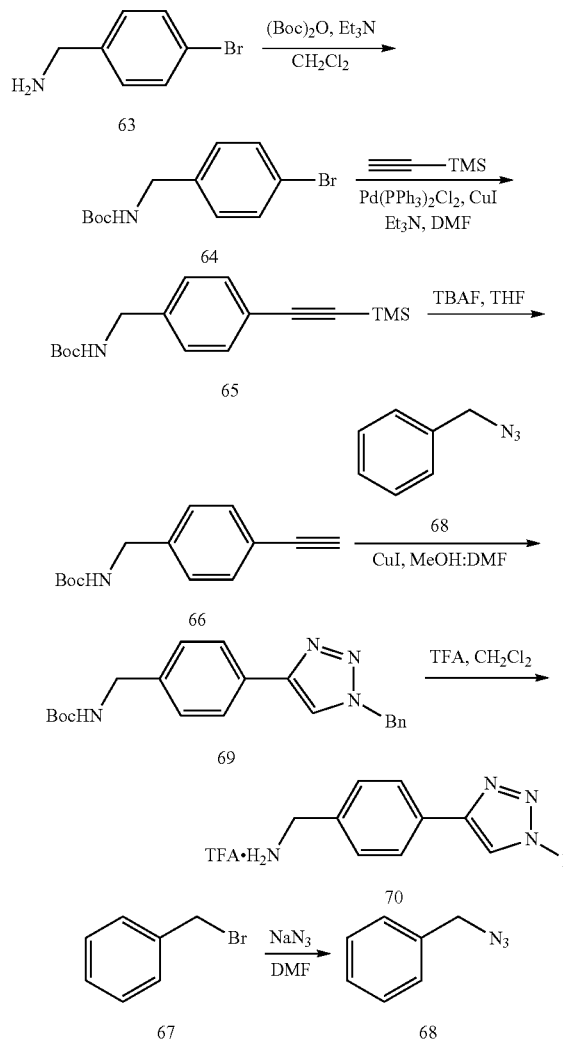

Synthesis of tert-butyl (4-bromobenzyl)carbamate (64)

To a stirred solution of (4-bromophenyl)methanamine 63 (5 g, 27.17 mmol) in CH$_2$Cl$_2$ (75 mL) under argon atmosphere were added triethylamine (11.32 mL, 80.59 mmol), Boc-anhydride (6.44 g, 29.54 mmol) at 0° C.; warmed to RT and stirred for 16 h. The reaction was monitored by TLC; after completion of the reaction, the reaction mixture was diluted with water (100 mL) and extracted with CH$_2$Cl$_2$ (3×100 mL). The combined organic extracts were washed with water (25 mL), dried over sodium sulfate, filtered and concentrated in vacuo to obtain the crude. The crude was purified through silica gel column chromatography using 5-8% EtOAc/hexanes to afford compound 64 (7 g, 91%) as white solid. TLC: 10% EtOAc/hexanes (R$_f$: 0.4); $^1$H-NMR (DMSO-d$_6$, 400 MHz): δ 7.50 (d, J=8.4 Hz, 2H), 7.41 (t, J=5.7 Hz, 1H), 7.19 (d, J=8.4 Hz, 2H), 4.08 (d, J=6.3 Hz, 2H), 1.38 (s, 9H).

Synthesis of tert-butyl (4-((trimethylsilyl)ethynyl)benzyl)carbamate (65)

To a stirred solution of compound 64 (3 g, 10.48 mmol) in DMF (60 mL) under argon atmosphere were added ethynyltrimethylsilane (14.88 mL, 104.79 mmol), copper iodide (207 mg, 1.04 mmol) and triethyl amine (15.14 mL, 104.95 mmol) in a sealed tube and purged under argon for 10 min. To this were added Pd(PPh$_3$)$_2$Cl$_2$ (742 mg, 1.04 mmol) and purged under argon for 10 min; heated to 70° C. and stirred for 16 h. The reaction was monitored by TLC; after completion of the reaction, the reaction mixture was poured into ice-cold water and extracted with EtOAc (2×100 mL). The combined organic extracts were dried over sodium sulfate, filtered and concentrated in vacuo to obtain the crude. The crude was purified through silica gel column chromatography using 10-15% EtOAc/hexanes to afford compound 65 (2.6 g, 82%) as dark brown solid. TLC: 10% EtOAc/hexanes (R$_f$: 0.4); $^1$H-NMR (DMSO-d$_6$, 500 MHz): δ 7.41-7.37 (m, 3H), 7.21 (d, J=7.8 Hz, 2H), 4.11 (d, J=6.1 Hz, 2H), 1.37 (s, 9H), 0.21 (s, 9H).

Synthesis of tert-butyl (4-ethynylbenzyl)carbamate (66)

To a stirred solution of compound 65 (2.6 g, 8.58 mmol) in THF (50 mL) under argon atmosphere was added tetra-n-butylammonium fluoride (10.3 mL, 2.08 mmol, 1 M solution in THF) drop wise for 10 min at 0° C.; warmed to RT and stirred for 4 h. The reaction was monitored by TLC; after completion of the reaction, the reaction mixture was diluted with EtOAc (50 mL), washed with saturated ammonium chloride solution (50 mL) and brine (50 mL). The organic extract was dried over sodium sulfate, filtered and concentrated in vacuo to obtain the crude. The crude was purified through silica gel column chromatography using 10-15% EtOAc/hexanes to afford compound 66 (1.5 g, 76%) as pale yellow solid. TLC: 10% EtOAc/hexanes (R$_f$: 0.3); $^1$H-NMR (DMSO-d$_6$, 500 MHz): δ 7.44-7.37 (m, 3H), 7.22 (d, J=7.8 Hz, 2H), 4.15-4.06 (m, 3H), 1.38 (s, 9H).

Synthesis of (azidomethyl) benzene (68)

To a stirred solution of (bromomethyl) benzene 67 (5 g, 29.24 mmol) in DMF (20 mL) under inert atmosphere was added sodium azide (2.85 g, 43.84 mmol) at RT and heated to 70° C. for 16 h. The reaction was monitored by TLC; after completion of the reaction, the reaction mixture was diluted with water (100 mL) and extracted with hexane (2×100 mL). The combined organic extracts were dried over sodium sulfate, filtered and concentrated in vacuo to afford compound 68 (4 g) as colorless oil. TLC: 100% hexane (R$_f$: 0.4); $^1$H-NMR (CDCl$_3$, 400 MHz): δ 7.43-7.29 (m, 5H), 4.34 (s, 2H).

Synthesis of tert-butyl (4-(1-benzyl-1H-1,2,3-triazol-5-yl)benzyl)carbamate (69)

To a stirred solution of compound 66 (1 g, 4.32 mmol) in MeOH: DMF (1: 1, 30 mL) under argon atmosphere were added compound 68 (1.74 g, 12.98 mmol) and copper iodide (857 mg, 4.32 mmol) in sealed tube at RT; heated to 80° C. and stirred for 16 h. The reaction was monitored by TLC; after completion of the reaction, the reaction mixture was cooled to RT and filtered and the residue was washed with EtOAc (100 mL). The filtrate was removed in vacuo to obtain the crude which was purified through silica gel column chromatography using 20-30% EtOAc/hexanes to afford compound 69 (1.1 g, 70%) as white solid. TLC: 30% EtOAc/hexanes ($R_f$: 0.2); $^1$H-NMR (DMSO-$d_6$, 500 MHz): δ 8.57 (s, 1H), 7.77 (d, J=8.1 Hz, 2H), 7.41-7.31 (m, 6H), 7.28 (d, J=8.1 Hz, 2H), 5.62 (s, 2H), 4.12 (d, J=6.1 Hz, 2H), 1.38 (s, 9H).

Synthesis of (4-(1-benzyl-1H-1,2,3-triazol-5-yl)phenyl)methanamine (70)

To a stirred solution of compound 69 (500 mg, 1.37 mmol) in CH$_2$Cl$_2$ (10 mL) under argon atmosphere was added trifluoro acetic acid (2 mL), dropwise for 10 min at 0° C.; warmed to RT and stirred for 4 h. The reaction was monitored by TLC; after completion of the reaction, the volatiles were removed in vacuo. The crude was triturated with diethyl ether (2×10 mL) and dried in vacuo to afford compound 70 (400 mg) as an off-white solid. TLC: 40% EtOAc/hexanes ($R_f$: 0.2); $^1$H-NMR (DMSO-$d_6$, 500 MHz): δ 8.67 (s, 1H), 8.24 (br s, 3H), 7.90 (d, J=8.1 Hz, 2H), 7.52 (d, J=8.1 Hz, 2H), 7.43-7.33 (m, 4H), 5.65 (s, 2H), 4.06 (q, J=5.4 Hz, 2H).

Example 16: Synthesis of (4-(1H-1,2,3-triazol-5-yl)phenyl)methanamine TFA salt (72)

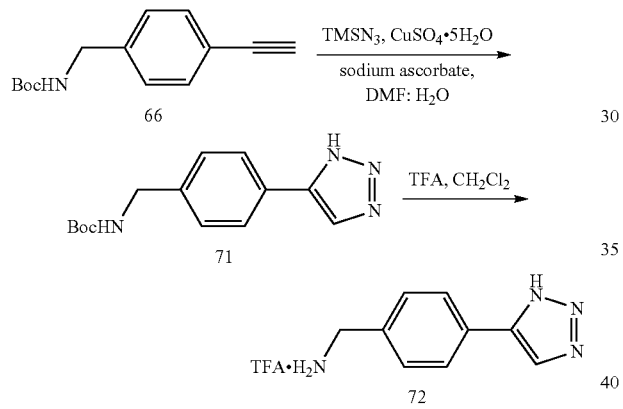

Synthesis of tert-butyl (4-(1H-1,2,3-triazol-5-yl)benzyl)carbamate (71)

To a stirred solution of compound 66 (500 mg, 2.16 mmol) in a mixture of DMF: H$_2$O (4: 1, 26 mL) were added azidotrimethylsilane (1.42 mL, 10.82 mmol), copper (II) sulfate pentahydrate (80.5 mg, 0.32 mmol) and sodium ascorbate (171.4 mg, 0.86 mmol) in sealed tube at RT; heated to 80° C. and stirred for 16 h. The reaction was monitored by TLC; after completion of the reaction, the reaction mixture was diluted with water (100 mL) and extracted with EtOAc (3×100 mL). The combined organic extracts were dried over sodium sulfate, filtered and concentrated in vacuo to obtain the crude. The crude was purified through combiflash chromatography using 50% EtOAc/hexanes to afford compound 71 (350 mg, 99%) as an off-white solid. TLC: 40% EtOAc/hexanes ($R_f$: 0.3); $^1$H NMR (DMSO-$d_6$, 400 MHz): δ 14.93 (br s, 1H), 8.22 (br s, 1H), 7.80 (d, J=7.2 Hz, 2H), 7.40 (t, J=5.6 Hz, 1H), 7.31 (d, J=7.8 Hz, 2H), 4.15 (d, J=5.8 Hz, 2H), 1.40 (s, 9H).

Synthesis of (4-(1H-1,2,3-triazol-5-yl)phenyl)methanamine TFA Salt (72)

To a stirred solution of compound 71(350 mg, 1.27 mmol) in CH$_2$Cl$_2$ (10 mL) under argon atmosphere was added trifluoro acetic acid (3 mL) dropwise for 10 min at 0° C.; warmed to RT and stirred for 3 h. The reaction was monitored by TLC; after completion of the reaction, the volatiles were removed in vacuo. The crude was triturated with diethyl ether (2×10 mL) and dried in vacuo to afford compound 72 (250 mg, crude) as an off-white solid. TLC: 30% EtOAc/hexanes ($R_f$: 0.2); $^1$H-NMR (DMSO-$d_6$, 500 MHz): δ 8.37 (br s, 1H), 8.17 (br s, to 3H), 7.92 (d, J=8.1 Hz, 2H), 7.54 (d, J=8.1 Hz, 2H), 4.07 (q, J=5.8 Hz, 2H).

Example 17: Synthesis of (3-(1H-1,2,3-triazol-5-yl)phenyl)methanamine (78)

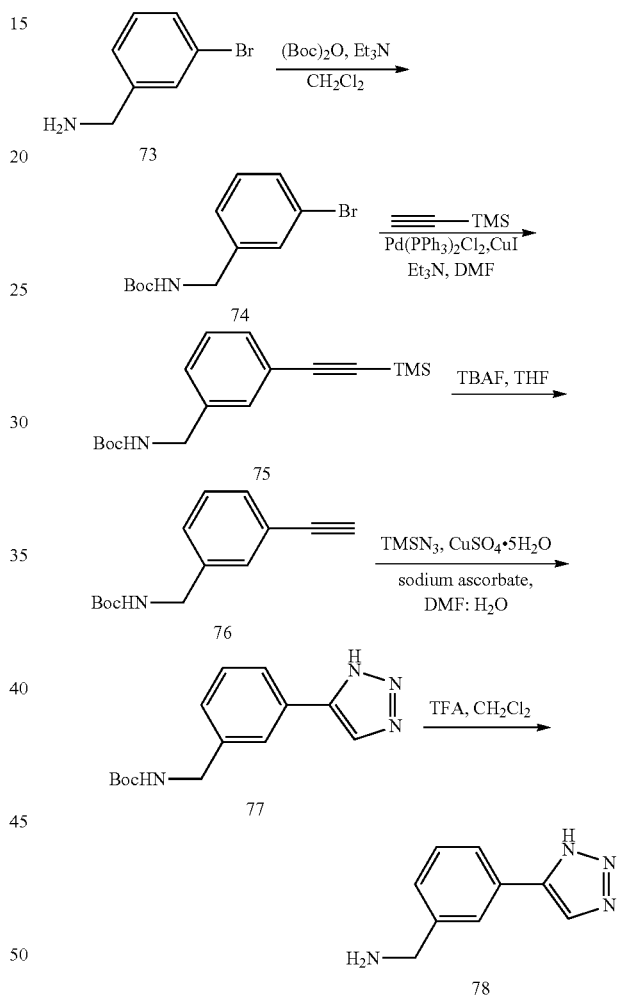

Synthesis of tert-butyl (3-bromobenzyl)carbamate (74)

To a stirred solution of (3-bromophenyl) methanamine 73 (5 g, 26.88 mmol) in CH$_2$Cl$_2$ (50 mL) under argon atmosphere were added triethylamine (1.16 mL, 80.59 mmol), Boc-anhydride (5.8 mL, 26.88 mmol) at 0° C.; warmed to RT and stirred for 16 h. The reaction was monitored by TLC; after completion of the reaction, the reaction mixture was diluted with water (100 mL) and extracted with CH$_2$Cl$_2$ (2×100 mL). The combined organic extracts were washed with water (25 mL), dried over sodium sulfate, filtered and concentrated in vacuo to obtain the crude. The crude was purified through silica gel column chromatography using 5%

EtOAc/hexanes to afford compound 74 (5 g, 65%) as white solid. TLC: 10% EtOAc/hexanes (R$_f$: 0.6); $^1$H-NMR (DMSO-d$_6$, 400 MHz): δ 7.45-7.37 (m, 3H), 7.32-7.20 (m, 2H), 4.12 (d, J=6.1 Hz, 2H), 1.39 (s, 9H).

Synthesis of tert-butyl (3-((trimethylsilyl) ethynyl) benzyl) carbamate (75)

To a stirred solution of tert-butyl (3-bromobenzyl) carbamate 74 (4 g, 13.98 mmol) in DMF (80 mL) under argon atmosphere were added ethynyltrimethylsilane (9.79 mL, 69.93 mmol), copper iodide (276 mg, 1.39 mmol) and triethyl amine (20 mL, 139.86 mmol) in a sealed tube and purged under argon for 30 min. To this were added Pd(PPh$_3$)$_2$Cl$_2$ (990 mg, 69.93 mmol) at RT and heated to 100° C. and stirred for 5 h. The reaction was monitored by TLC; after completion of the reaction, the reaction mixture was filtered through celite. The filtrate was concentrated in vacuo; the residue was diluted with EtOAc (200 mL) and washed with water (2×100 mL). The organic extract were dried over sodium sulfate, filtered and concentrated in vacuo to obtain the crude. The crude was purified through silica gel column chromatography using 5% EtOAc/hexanes to afford compound 75 (2.5 g, 59%) as colorless liquid. TLC: 10% EtOAc/hexanes (R$_f$: 0.5); $^1$H-NMR (DMSO-d$_6$, 500 MHz): δ 7.40 (t, J=6.1 Hz, 1H), 7.33-7.29 (m, 3H), 7.28-7.23 (m, 1H), 4.10 (d, J=6.1 Hz, 2H), 1.39 (s, 9H), 0.23 (s, 9H).

Synthesis of tert-butyl (3-ethynylbenzyl) carbamate (76)

To a stirred solution of compound 75 (2.5 g, 8.25 mmol) in THF (50 mL) under argon atmosphere was added tetra-n-butylammonium fluoride (9 mL, 9.07 mmol, 1 M solution in THF) dropwise for 10 min at 0° C.; warmed to RT and stirred for 4 h. The reaction was monitored by TLC; after completion of the reaction, the reaction mixture was quenched with saturated ammonium chloride solution (50 mL) extracted with EtOAc (2×100 mL). The combined organic extracts were dried over sodium sulfate, filtered and concentrated in vacuo to obtain the crude. The crude was purified through silica gel column chromatography using 8% EtOAc/hexanes to afford compound 76 (1.4 g, 73%) as colorless liquid. TLC: 10% EtOAc/hexanes (R$_f$: 0.3); $^1$H-NMR (DMSO-d$_6$, 500 MHz): δ 7.45-7.39 (m, 1H), 7.35-7.32 (m 3H), 7.29-7.25 (m, 1H), 4.16 (s, 1H), 4.11 (d, J=6.1 Hz, 2H), 1.39 (s, 9H)

Synthesis of tert-butyl (3-(1H-1,2,3-triazol-5-yl) benzyl)carbamate (77)

To a stirred solution of compound 76 (700 mg, 3.03 mmol) in a mixture of DMF: H$_2$O (4: 1, 20 mL) was added azidotrimethylsilane (2.17 mL, 15.15 mmol), copper (II) sulfate pentahydrate (11 mg, 0.045 mmol) and sodium ascorbate (240 mg, 1.21 mmol) in sealed tube at RT; heated to 90° C. and stirred for 6 h. The reaction was monitored by TLC; after completion of the reaction, the reaction mixture was diluted with water (100 mL) and extracted with EtOAc (2×75 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 77 (500 mg, 60%) as an off-white solid. TLC: 5% MeOH/CH$_2$Cl$_2$ (R$_f$: 0.3); $^1$H NMR (DMSO-d$_6$, 400 MHz): 14.95 (br s, 1H), 8.19 (br s, 1H), 7.75 (br s, 1H), 7.71 (d, J=7.5 Hz, 1H), 7.48-7.36 (m, 2H), 7.22 (br s, 1H), 4.18 (d, J=6.1 Hz, 2H), 1.40 (s, 9H).

Synthesis of (3-(1H-1,2,3-triazol-5-yl)phenyl)methanamine (78)

To a stirred solution of compound 77 (500 mg, 1.82 mmol) in CH$_2$Cl$_2$ (10 mL) under argon atmosphere was added trifluoro acetic acid (3 mL) dropwise for 10 min at 0° C.; warmed to RT and stirred for 5 h. The reaction was monitored by TLC; after completion of the reaction, the volatiles were removed in vacuo. The crude was triturated with diethyl ether (2×10 mL) and dried in vacuo to afford compound 78 (700 mg, crude) as an off-white solid. TLC: 10% MeOH/CH$_2$Cl$_2$ (R$_f$: 0.2); $^1$H-NMR (DMSO-d$_6$, 500 MHz): δ 15.07 (br s, 1H), 8.25 (br s, 3H), 8.01 (br s, 1H), 7.86 (d, J=7.2 Hz, 1H), 7.52 (t, J=7.7 Hz, 1H), 7.44 (d, J=6.9 Hz, 1H), 4.10 (d, J=3.2 Hz, 2H).

Example 18: Synthesis of (4-(pyrimidin-5-yl)phenyl)methanamine (83)

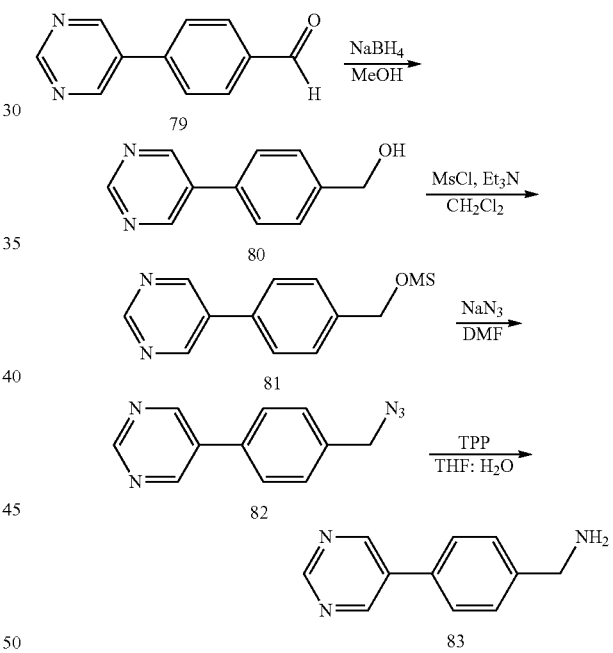

Synthesis of (4-(pyrimidin-5-yl)phenyl)methanol (80)

To a stirred solution of 4-(pyrimidin-5-yl)benzaldehyde 79 (500 mg, 2.71 mmol) in MeOH (20 mL) under argon atmosphere and sodium borohydride (155 mg, 39.99 mmol) at 0° C.; warmed to RT and stirred for 2 h. The reaction was monitored by TLC; after completion of the reaction, volatiles were removed in vacuo. The residue was diluted with brine solution (100 mL), extracted with EtOAc (2×50 mL). The combined organic extracts were dried over sodium sulphate, filtered and concentrated in vacuo to obtain the crude. The crude was purified through silica gel column chromatography using 5% MeOH/CH$_2$Cl$_2$ to afford compound 80 (260 mg, 51%) as white solid. TLC: 20% EtOAc/ hexanes (R$_f$: 0.4); $^1$H-NMR (CDCl$_3$, 500 MHz): δ 9.20 (s, 1H), 8.93 (s, 2H), 7.58 (d, J=8.5 Hz, 2H), 7.53 (d, J=8.0 Hz, 2H), 4.79 (s, 2H).

Synthesis of 4-(pyrimidin-5-yl)benzyl methanesulfonate (81)

To a stirred solution of compound 80 (260 mg, 1.39 mmol) in CH$_2$Cl$_2$ (10 mL) under argon atmosphere were added triethyl amine (0.3 mL, 2.09 mmol), methane sulfonyl chloride (0.16 mL, 2.09 mmol) at 0° C.; warmed to RT and stirred for 14 h. The reaction was monitored by TLC; after completion of the reaction, the reaction mixture was diluted with water (20 mL), washed with 10% NaHCO$_3$ solution (30 mL), dried over sodium sulfate, filtered and concentrated in vacuo to obtain crude compound 81 (300 mg) as thick syrup. The crude was carried to the next step without further purification. TLC: 5% MeOH/CH$_2$Cl$_2$ (R$_f$: 0.4).

Synthesis of 5-(4-(azidomethyl)phenyl)pyrimidine (82)

To a stirred solution of compound 81 (300 mg, crude) in DMF (6 mL) under argon atmosphere was added sodium azide (74 mg, 1.13 mmol) at RT; heated to 60° C. and stirred for 2 h. The reaction was monitored by TLC; after completion of the reaction, the reaction mixture was diluted with ice water (20 mL) and extracted with EtOAc (2×50 mL). The combined organic extracts were dried over sodium sulfate, filtered and concentrated in vacuo to obtain crude. The crude was purified through silica gel column chromatography using 20% EtOAc/hexanes to afford compound 82 (45 mg) as colorless thick syrup. TLC: 30% EtOAc/hexanes (R$_f$: 0.6); $^1$H-NMR (CDCl$_3$, 400 MHz): δ 9.22 (s, 1H), 8.96 (s, 2H), 7.61 (d, J=8.4 Hz, 2H), 7.48 (d, J=8.0 Hz, 2H), 4.43 (s, 2H).

Synthesis of (4-(pyrimidin-5-yl)phenyl)methanamine (83)

To a stirred solution of compound 82 (40 mg, 0.18 mmol) in THF: H$_2$O (9: 1, 2 mL) was added triphenyl phosphine (74 mg, 0.28 mmol) at RT and stirred for 16 h. The reaction was monitored by TLC; after completion of the reaction, the volatiles were removed in vacuo to obtain the crude. The crude was purified through silica gel column chromatography using 10% MeOH/CH$_2$Cl$_2$ to afford compound 83 (23 mg, 66%) as an off-white solid. TLC: 10% MeOH/CH$_2$Cl$_2$ (R$_f$: 0.2); $^1$H-NMR (DMSO-d$_6$, 400 MHz): δ 9.21 (s, 1H), 9.17 (s, 2H), 8.27 (br s, 2H), 7.87 (d, J=8.0 Hz, 2H), 7.64 (d, J=8.4 Hz, 2H), 4.07 (s, 2H).

Example 19: Synthesis of [1,1'-biphenyl]1-3-ylmethanamine hydrochloride (86)

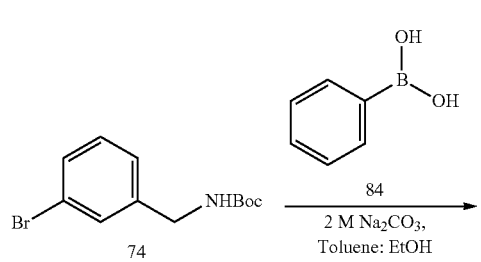

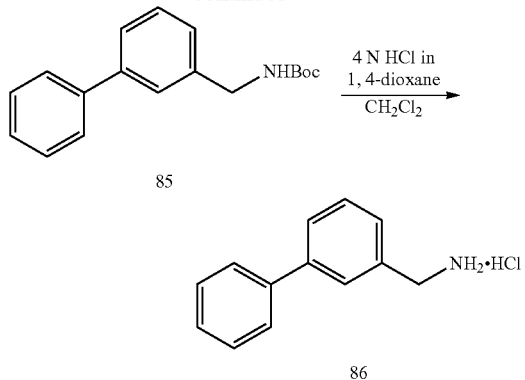

Synthesis of tert-butyl ([1,1'-biphenyl]-3-ylmethyl)carbamate (85)

To a stirred solution of tert-butyl (3-bromobenzyl)carbamate 74 (1 g, 3.49 mmol) in Toluene: EtOH (4: 1, 25 mL) under inert atmosphere were added phenylboronic acid 84 (512 mg, 4.19 mmol) and 2 M sodium carbonate solution (5 mL) at RT and purged under argon atmosphere for 20 min. To this was added Pd(dppf)Cl$_2$ (77 mg, 0.10 mmol) and heated to 100° C. for 16 h. The reaction was monitored by TLC; after completion of the reaction, the volatiles were dried in vacuo. The residue was diluted with water (50 mL) and EtOAc (50 mL), filtered through celite and washed with EtOAc (20 mL). The filtrate was dried over sodium sulfate, filtered and concentrated in vacuo to obtain the crude. The crude was purified through silica gel column chromatography using 2-8% EtOAc/hexanes to afford compound 85 (600 mg, 60%) as colorless syrup. TLC: 10% EtOAc/hexanes (R$_f$: 0.3); $^1$H-NMR (DMSO-d$_6$, 400 MHz): 7.63 (d, J=7.3 Hz, 2H), 7.55-7.45 (m, 4H), 7.43-7.34 (m, 3H), 7.24 (d, J=7.5 Hz, 1H), 4.20 (d, J=5.9 Hz, 2H), 1.40 (s, 9H).

Synthesis of [1,1'-biphenyl]-3-ylmethanamine hydrochloride (86)

To a stirred solution of compound 85 (600 mg, 2.12 mmol) in CH$_2$Cl$_2$ (10 mL) was added 4 N HCl in 1,4-Dioxane (10 mL) under argon atmosphere at 0° C.; warmed to RT and stirred for 2 h. The reaction was monitored by TLC; after completion of the reaction, the volatiles were removed in vacuo to afford compound 86 (300 mg, 64%) as pale yellow solid. TLC: 10% EtOAc/hexanes (R$_f$: 0.2); $^1$H NMR (DMSO-d$_6$, 400 MHz): δ 8.50 (br s, 3H), 7.86 (s, 1H), 7.74-7.64 (m, 3H), 7.55-7.45 (m, 4H), 7.43-7.36 (m, 1H), 4.09 (br s, 2H).

Example 20: Synthesis of 4'-(aminomethyl)-N,N-dimethyl-[1,1'-biphenyl]-4-amine hydrochloride (91)

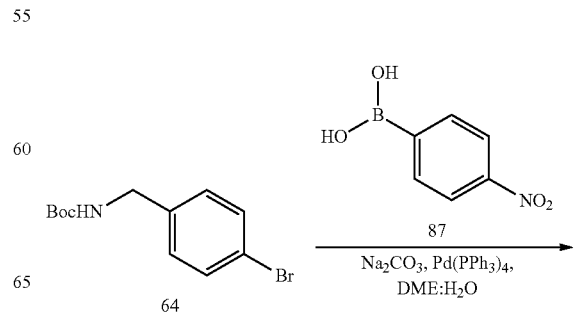

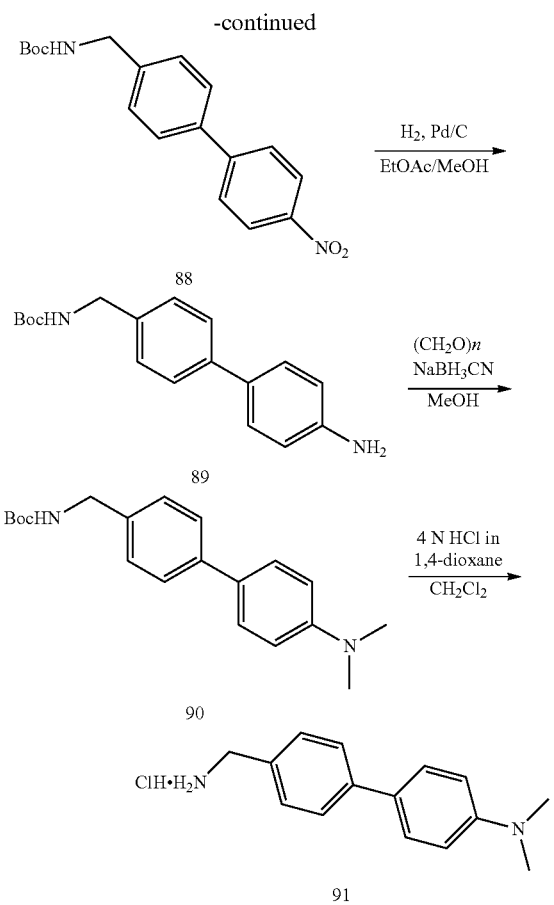

Synthesis of tert-butyl ((4'-nitro-[1,1'-biphenyl]-4-yl) methyl) carbamate (88)

To a stirring solution of tert-butyl (4-bromobenzyl) carbamate 64 (500 mg, 1.75 mmol) in 1,2 dimethoxy ethane: H$_2$O (10: 1, 22 mL) was added (4-nitrophenyl) boronic acid 87 (321 mg, 1.92 mmol), sodium carbonate (557 mg, 5.25 mmol) and purged under argon atmosphere for 15 min. To this was added Pd(PPh$_3$)$_4$ (202 mg, 0.17 mmol) and purged under argon atmosphere at RT; heated to reflux and stirred for 16 h. The reaction was monitored by TLC; after completion the reaction the volatiles were removed in vacuo to obtain the crude. The crude was purified through silica gel column chromatography using 20-40% EtOAc/hexanes to afford compound 88 (410 mg, 72%) as pale yellow solid. TLC: 20% EtOAc/hexanes (R$_f$: 0.4); $^1$H-NMR (DMSO-d$_6$, 400 MHz): δ 8.30 (d, J=8.9 Hz, 2H), 7.96 (d, J=8.9 Hz, 2H), 7.75 (d, J=8.2 Hz, 2H), 7.46 (t, J=5.9 Hz, 1H), 7.39 (d, J=8.2 Hz, 2H), 4.19 (d, J=6.2 Hz, 2H), 1.40 (s, 9H). LC-MS: 94.36%; 327.3 (M−1)$^+$; (column; X-select CSH C-18 (150×3 mm, 2.5 μm); RT 4.38 min. 2.5 mM Aq. NH$_4$OAc: ACN; 0.8 mL/min).

Synthesis of tert-butyl ((4'-amino-[1,1'-biphenyl]-4-yl)methyl)carbamate (89)

To a stirring solution of compound 88 (400 mg, 1.22 mmol) in EtOAc: MeOH (4: 1, 25 mL) under inert atmosphere was added 10% Pd/C (100 mg) at RT and stirred under hydrogen atmosphere (balloon pressure) at RT for 16 h. The reaction was monitored by TLC; after completion of the reaction, the reaction mixture was filtered through celite and washed with EtOAc: MeOH (1: 1, 100 mL). The filtrate was concentrated in vacuo to afford compound 89 (300 mg, 83%) as an off-white solid. TLC: 30% EtOAc/hexanes (R$_f$: 0.2); $^1$H NMR (DMSO-d$_6$, 400 MHz): δ 7.46 (d, J=8.3 Hz, 2H), 7.33 (d, J=8.5 Hz, 3H), 7.22 (d, J=8.2 Hz, 2H), 6.62 (d, J=8.6 Hz, 2H), 5.18 (s, 2H), 4.11 (d, J=6.2 Hz, 2H), 1.40 (s, 9H); LC-MS: 98.73%; 298.9 (M$^+$+1); (column; Ascentis Express C18, (50×3.0 mm, 2.7 μm); RT 2.00 min. 0.025% Aq. TFA+5% ACN: ACN+5% 0.025% Aq. TFA, 1.2 mL/min).

Synthesis of tert-butyl ((4'-(dimethylamino)-[1,1'-biphenyl]-4-yl)methyl) carbamate (90)

To a stirring solution of compound 89 (300 mg, 1.00 mmol) in MeOH (20 mL) under inert atmosphere were added paraformaldehyde (604 mg, 20.13 mmol) and sodium cyanoborohydride (1.27 g, 20.13 mmol) at RT and stirred for 6 h. The reaction was monitored by TLC; after completion of the reaction, the volatiles were removed in vacuo. The residue was diluted with EtOAc (100 mL) washed with water (50 mL). The organic extract was dried over sodium sulfate, filtered and concentrated in vacuo to obtain the crude. The crude was purified through silica gel column chromatography using 5-10% EtOAc/hexanes to afford compound 90 (300 mg, 91%) as an off-white solid. TLC: 30% EtOAc/hexanes (R$_f$: 0.8); $^1$H NMR (DMSO-d$_6$, 500 MHz): δ 7.50 (dd, J=13.2, 8.5 Hz, 4H), 7.37 (t, J=5.9 Hz, 1H), 7.25 (d, J=7.8 Hz, 2H), 6.79 (d, J=9.0 Hz, 2H), 4.12 (d, J=6.1 Hz, 2H), 2.93 (s, 6H), 1.40 (s, 9H); LC-MS: 98.91%; 327.1 (M$^+$+1); (column; Ascentis Express C18, (50×3.0 mm, 2.7 μm); RT 2.32 min. 0.025% Aq. TFA+5% ACN: ACN+5% 0.025% Aq. TFA, 1.2 mL/min).

Synthesis of 4'-(aminomethyl)-N,N-dimethyl-[1,1'-biphenyl]-4-amine hydrochloride (91)

To a stirring solution of compound 90 (300 mg, 0.92 mmol) in CH$_2$Cl$_2$ (5 mL) under inert atmosphere was added 4 N HCl in 1,4-dioxane (3 mL) at 0° C.; warmed to RT and stirred for 4 h. The reaction was monitored by TLC; after completion of the reaction, the volatiles were removed in vacuo to obtain the crude. The crude was triturated with EtOAc (2×5 mL) and dried in vacuo to afford compound 91 (300 mg) as pale yellow solid. TLC: 30% EtOAc/hexane (R$_f$: 0.1); $^1$H-NMR (DMSO-d$_6$, 500 MHz): δ 8.51 (br s, 3H), 7.70 (d, J=8.1 Hz, 4H), 7.57 (d, J=8.1 Hz, 2H), 7.42-7.19 (m, 2H), 4.04 (q, J=5.7 Hz, 2H), 3.05 (s, 6H); LC-MS: 85.63%; 226.6 (M$^+$+1); (column; Ascentis Express C18, (50×3.0 mm, 2.7 μm); RT 1.25 min. 0.025% Aq. TFA+5% ACN: ACN+5% 0.025% Aq. TFA, 1.2 mL/min).

Example 21: Synthesis of (4'-fluoro-[1,1'-biphenyl]-4-yl)methanamine hydrochloride (94)

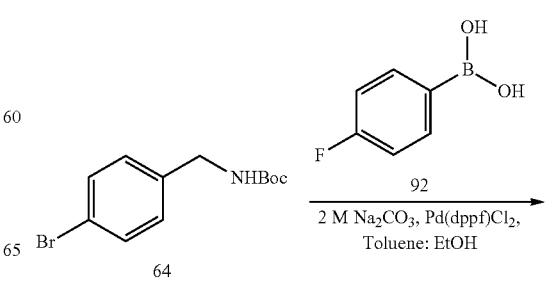

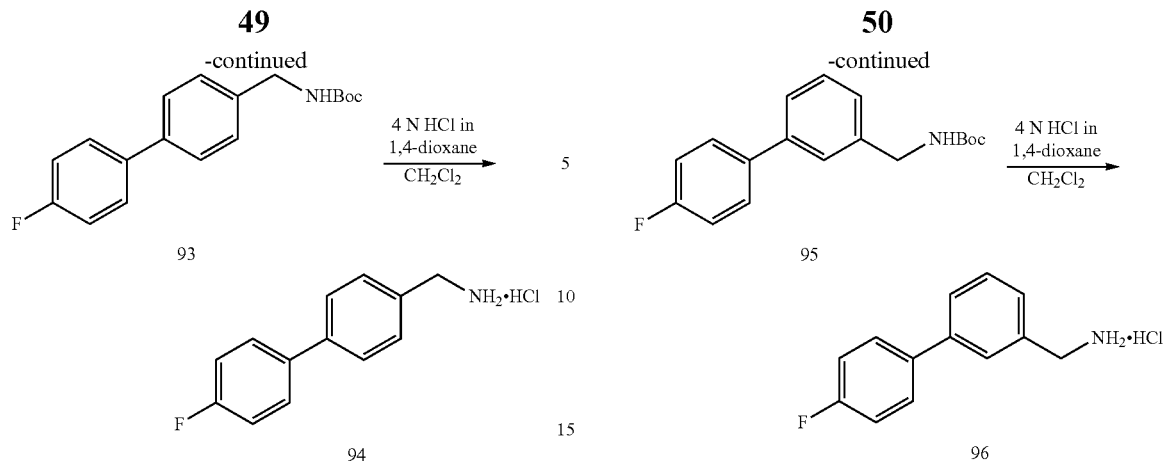

Synthesis of tert-butyl ((4'-fluoro-[1,1'-biphenyl]-4-yl)methyl)carbamate (93)

To a stirred solution of tert-butyl (4-bromobenzyl) carbamate 64 (500 mg, 1.74 mmol) in a mixture of toluene:EtOH (4: 1, 12.5 mL) under inert atmosphere were added (4-fluorophenyl)boronic acid 92 (257 mg, 1.83 mmol) and 2 M sodium carbonate solution (2.5 mL) at RT in a sealed tube and purged under argon atmosphere for 15 min. To this was added Pd(dppf)Cl$_2$ (38.4 mg, 0.05 mmol) and heated to 90° C. for 16 h. The reaction was monitored by TLC; after completion of the reaction, the reaction mixture was diluted with water (50 mL) and EtOAc (2×50 mL). The combined organic extracts were dried over sodium sulphate, filtered and concentrated in vacuo to obtain the crude. The crude was purified by combiflash chromatography using 10% EtOAc/hexanes to afford compound 93 (400 mg, 76%) as an off-white solid. TLC: 10% EtOAc/hexanes (R$_f$: 0.3); $^1$H-NMR (DMSO-d$_6$, 400 MHz): 7.67 (dd, J=8.4, 5.5 Hz, 2H), 7.58 (d, J=8.1 Hz, 2H), 7.43 (t, J=6.1 Hz, 1H), 7.31-7.24 (m, 4H), 4.14 (d, J=6.4 Hz, 2H), 1.39 (s, 9H)

Synthesis of (4'-fluoro-[1,1'-biphenyl]-4-yl)methanamine hydrochloride (94)

To a stirred solution of compound 93 (500 mg, 2.06 mmol) in CH$_2$Cl$_2$ (10 mL) under argon atmosphere was added 4 N HCl in 1,4-Dioxane (2.5 mL) at 0° C.; warmed to RT and stirred for 3 h. The reaction was monitored by TLC; after completion of the reaction, the volatiles were removed in vacuo to obtain the crude. The crude was washed with diethyl ether (2×5 mL), n-pentane (2×5 mL) to afford compound 94 (200 mg, 68%) as white solid. TLC: 20% EtOAc/hexanes (R$_f$: 0.2); $^1$H NMR (DMSO-d$_6$, 400 MHz): δ 8.40 (br s, 3H), 7.78-7.67 (m, 4H), 7.57 (d, J=8.2 Hz, 2H), 7.31 (t, J=8.8 Hz, 2H), 4.06 (br s, 2H).

Example 22: Synthesis of (4'-fluoro-[1,1'-biphenyl]-3-yl)methanamine hydrochloride (96)

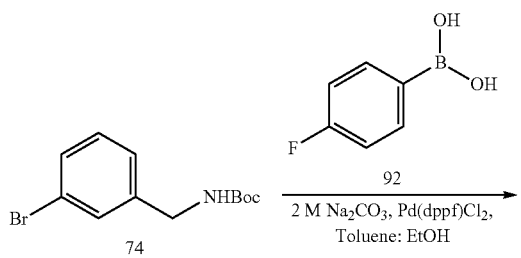

Synthesis of tert-butyl ((4'-fluoro-[1,1'-biphenyl]-3-yl)methyl)carbamate (95)

To a stirred solution of tert-butyl (3-bromobenzyl) carbamate 74 (100 mg, 0.34 mmol) in a mixture of toluene:EtOH (4: 1, 2.5 mL) under inert atmosphere were added 2 M aqueous sodium carbonate solution (0.5 mL) and (4-fluorophenyl) boronic acid 92 (58 mg, 0.41 to mmol) and at RT and purged under argon atmosphere for 15 min. To this was added Pd(dppf)Cl$_2$ (7.6 mg, 0.01 mmol) and heated to 80° C. for 6 h. The reaction was monitored by TLC; after completion of the reaction, the organic layer was separated dried over sodium sulphate, filtered and concentrated in vacuo to obtain the crude. The crude was purified through silica gel column chromatography using 2-8% EtOAc/hexanes to afford compound 95 (100 mg, 95%) as an off-white solid. TLC: 10% EtOAc/hexanes (R$_f$: 0.3); $^1$H-NMR (DMSO-d$_6$, 400 MHz): 7.67 (dd, J=8.7, 5.4 Hz, 2H), 7.52-7.48 (m, 2H), 7.40 (t, J=7.7 Hz, 2H), 7.29 (t, J=8.8 Hz, 2H), 7.23 (d, J=7.3 Hz, 1H), 4.19 (d, J=6.0 Hz, 2H), 1.40 (s, 9H).

Synthesis of (4'-fluoro-[1,1'-biphenyl]-3-yl) methanamine hydrochloride (96)

To a stirred solution of compound 95 (130 mg, 0.43 mmol) in CH$_2$Cl$_2$ (2 mL) under inert atmosphere was added 4 N HCl in 1,4-dioxane (2 mL) at 0° C.; warmed to RT and stirred for 2 h. The reaction was monitored by TLC; after completion of the reaction, the volatiles were removed in vacuo to afford compound 96 (90 mg, 88%) as an off-white solid. TLC: 30% EtOAc/hexanes (R$_f$: 0.1); LC-MS: 98.27%; 201.9 (M$^+$+1); (column; Ascentis Express C18, (50×3.0 mm, 2.7 μm); RT 1.76 min. 0.025% Aq. TFA+5% ACN: ACN+5% 0.025% Aq. TFA, 1.2 mL/min).

Example 23: Synthesis of 4'-(aminomethyl)-[1,1'-biphenyl]-3-ol hydrochloride (99)

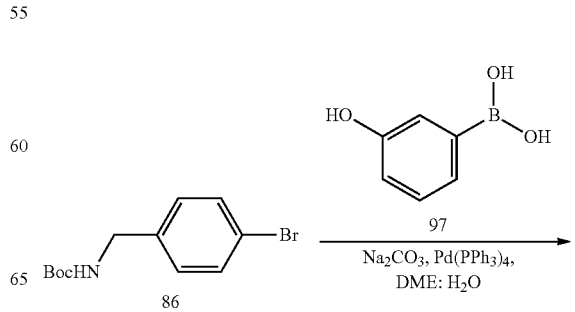

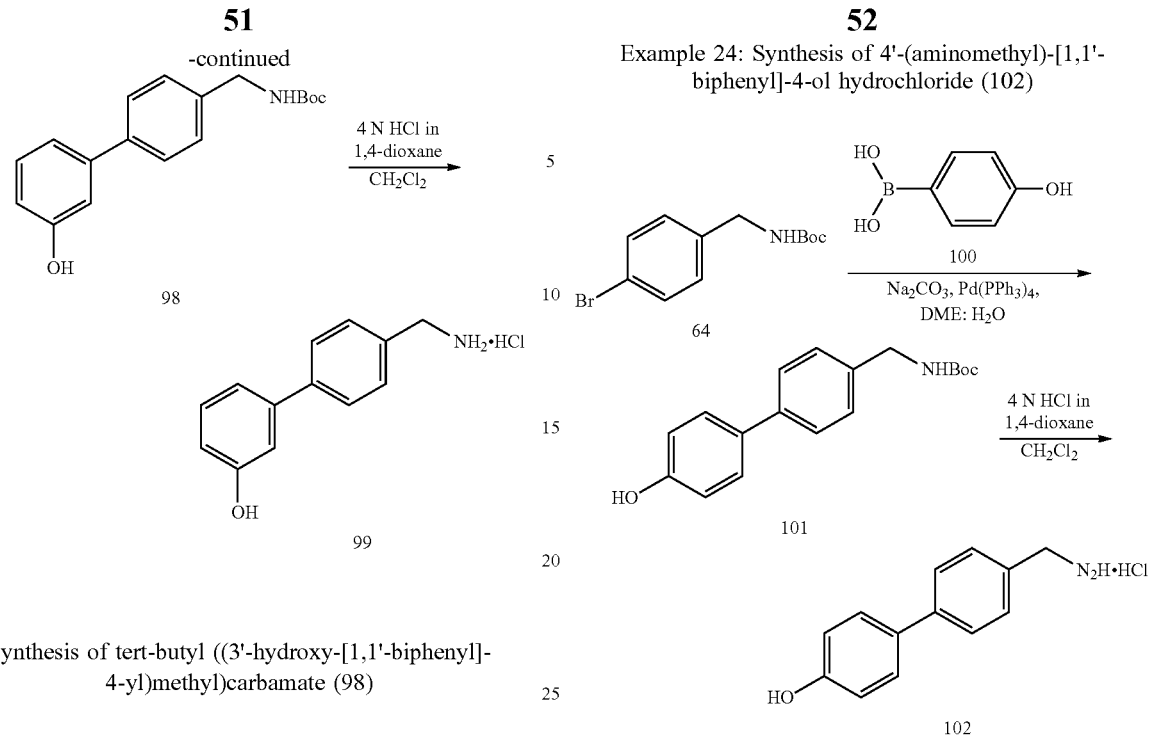

Synthesis of tert-butyl ((3'-hydroxy-[1,1'-biphenyl]-4-yl)methyl)carbamate (98)

To a stirred solution of compound 86 (500 mg, 1.74 mmol) in 1,2 dimethoxy ethane: $H_2O$ (4: 1, 72.5 mL) were added (3-hydroxyphenyl) boronic acid 97 (290 mg, 2.10 mmol), sodium carbonate (505 mg, 4.76 mmol) and purged under argon atmosphere for 5 min. To this was added Pd(PPh$_3$)$_4$ (202 mg, 0.17 mmol) at RT; heated to 100° C. and stirred for 16 h. The reaction was monitored by TLC; after completion the reaction mixture was extracted with EtOAc (3×100 mL). The combined organic extracts were dried over sodium sulfate, filtered and concentrated in vacuo to obtain the crude. The crude was purified through silica gel column chromatography using 10-20% EtOAc/hexanes to afford compound 98 (400 mg, 77%) as pale yellow oil. TLC: 20% EtOAc/hexanes (R$_f$: 0.2); $^1$H-NMR (DMSO-d$_6$, 400 MHz): δ 9.48 (s, 1H), 7.53 (d, J=8.1 Hz, 2H), 7.40 (t, J=5.9 Hz, 1H), 7.29 (d, J=8.1 Hz, 2H), 7.23 (t, J=7.8 Hz, 1H), 7.04 (d, J=7.8 Hz, 1H), 6.99 (s, 1H), 6.75 (dd, J=8.0, 1.6 Hz, 1H), 4.15 (d, J=6.1 Hz, 2H), 1.40 (s, 9H).

Synthesis of 4'-(aminomethyl)-[1,1'-biphenyl]-3-ol hydrochloride (99)

To a stirred solution of tert-butyl ((3'-hydroxy-[1,1'-biphenyl]-4-yl) methyl) carbamate 98 (800 mg, 2.67 mmol) in $CH_2Cl_2$ (15 mL) under inert atmosphere was added 4 N HCl in 1,4-dioxane (10 mL) at 0° C.; warmed to RT and stirred for 3 h. The reaction was monitored by TLC; after completion of the reaction, the volatiles were removed in vacuo to obtain the crude. The crude was triturated with diethyl ether (20 mL), n-pentane (20 mL) and dried in vacuo to afford compound 99 (550 mg, 88%) as an off-white solid. TLC: 20% EtOAc/hexanes (R$_f$: 0.2); $^1$H-NMR (DMSO-d$_6$, 500 MHz): δ 9.55 (s, 1H), 8.30 (br s, 3H), 7.63 (d, J=8.1 Hz, 2H), 7.52 (d, J=8.1 Hz, 2H), 7.24 (t, J=7.8 Hz, 1H), 7.08-6.99 (m, 2H), 6.77 (dd, J=8.0, 1.6 Hz, 1H), 4.04 (s, 2H).

Example 24: Synthesis of 4'-(aminomethyl)-[1,1'-biphenyl]-4-ol hydrochloride (102)

Synthesis of tert-butyl ((4'-hydroxy-[1,1'-biphenyl]-4-yl)methyl)carbamate (101)

To a stirred solution of compound 64 (1 g, 3.49 mmol) in 1,2 dimethoxy ethane: $H_2O$ (4: 1, 10 mL) were added (4-hydroxyphenyl) boronic acid 100 (580 mg, 4.19 mmol), sodium carbonate (741 mg, 6.99 mmol) and purged under argon atmosphere for 15 min. To this was added Pd(PPh$_3$)$_4$ (404 mg, 0.34 mmol) at RT; heated to 100° C. and stirred for 16 h. The reaction was monitored by TLC; after completion the reaction mixture was diluted with water (100 mL) and extracted with EtOAc (2×100 mL). The combined organic extracts were dried over sodium sulfate, filtered and concentrated in vacuo to obtain the crude. The crude was purified through silica gel column chromatography using 2-10% EtOAc/hexanes to afford compound 101 (400 mg, 33%) as pale brown solid. TLC: 10% EtOAc/hexanes (R$_f$: 0.3); $^1$H-NMR (DMSO-d$_6$, 400 MHz): δ 9.48 (s, 1H), 7.51 (d, J=8.2 Hz, 2H), 7.46 (d, J=8.6 Hz, 2H), 7.37 (t, J=5.8 Hz, 1H), 7.26 (d, J=8.2 Hz, 2H), 6.83 (d, J=8.6 Hz, 2H), 4.13 (d, J=6.1 Hz, 2H), 1.40 (s, 9H).

Synthesis of 4'-(aminomethyl)-[1,1'-biphenyl]-4-ol hydrochloride (102)

To a stirred solution of compound 101 (200 mg, 0.66 mmol) in $CH_2Cl_2$ (5 mL) under inert atmosphere was added 4 N HCl in 1,4-dioxane (5 mL) at 0° C.; warmed to RT and stirred for 6 h. The reaction was monitored by TLC; after completion of the reaction, the volatiles were removed in vacuo to obtain the crude. The crude was washed with diethyl ether (2×10 mL) and dried in vacuo to afford compound 102 (135 mg, 86%) as an off-white solid. TLC: 30% EtOAc/hexanes (R$_f$: 0.1); $^1$H-NMR (DMSO-d$_6$, 400 MHz): δ 9.60 (s, 1H), 8.25 (br s, 3H), 7.63 (d, J=8.2 Hz, 2H), 7.53-7.47 (m, 4H), 6.86 (d, J=8.6 Hz, 2H), 4.04 (s, 2H).

Example 25: Synthesis of 4'-((methylamino)methyl)-[1,1'-biphenyl]-4-ol hydrochloride (105)

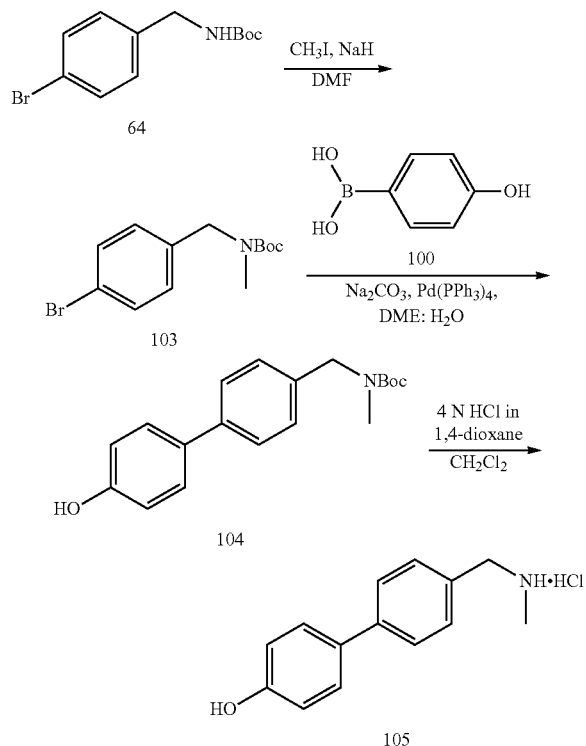

Synthesis of tert-butyl (4-bromobenzyl)(methyl)carbamate (103)

To a stirred solution of tert-butyl (4-bromobenzyl) carbamate 64 (300 mg, 1.04 mmol) in DMF (6 mL) under inert atmosphere was added sodium hydride (60%, 50 mg, 2.09 mmol) at 0° C. and stirred for 15 min. To this was added methyl iodide (0.19 mL, 3.14 mmol) at 0° C.; warmed to RT and stirred for 4 h. The reaction was monitored by TLC; after completion of the reaction, the reaction mixture was quenched with ice cold water (100 mL) and extracted with diethyl ether (2×50 mL). The combined organic extracts were washed with brine (50 mL), dried over sodium sulphate, filtered and concentrated in vacuo to obtain the crude. The crude compound was purified through silica gel column chromatography using 5% EtOAc/hexanes to afford compound 103 (250 mg, 80%) as colorless syrup. TLC: 10% EtOAc/hexanes ($R_f$: 0.2); $^1$H-NMR (DMSO-$d_6$, 400 MHz): δ 7.55 (d, J=8.3 Hz, 2H), 7.17 (d, J=8.5 Hz, 2H), 4.33 (s, 2H), 2.75 (s, 3H), 1.38 (br s, 9H).

Synthesis of tert-butyl ((4'-hydroxy-[1,1'-biphenyl]-4-yl) methyl)(methyl)carbamate (104)

To a stirred solution compound 103 (250 mg, 0.83 mmol) in 1,2 dimethoxy ethane: H$_2$O (4: 1, 20 mL) were added (4-hydroxyphenyl) boronic acid 100 (115 mg, 0.83 mmol), sodium carbonate (265 mg, 2.50 mmol) and purged under argon atmosphere for 15 min. To this was added Pd(PPh$_3$)$_4$ (94 mg, 0.083 mmol) at RT; heated to 100° C. and stirred for 16 h. The reaction was monitored by TLC; after completion the reaction mixture was diluted with water (50 mL) and extracted with EtOAc (2×75 mL). The combined organic extracts were dried over sodium sulfate, filtered and concentrated in vacuo to obtain the crude. The crude was purified through silica gel column chromatography using 30% EtOAc/hexanes to afford compound 104 (150 mg, 57%) as an off-white solid. TLC: 40% EtOAc/hexanes ($R_f$: 0.3); $^1$H-NMR (DMSO-$d_6$, 500 MHz): 9.51 (s, 1H), 7.55 (d, J=7.5 Hz, 2H), 7.47 (d, J=8.7 Hz, 2H), 7.25 (d, J=8.1 Hz, 2H), 6.84 (d, J=8.7 Hz, 2H), 4.38 (s, 2H), 2.76 (s, 3H), 1.42 (br s, 9H).

Synthesis of 4'-((methylamino) methyl)-[1,1'-biphenyl]-4-ol hydrochloride (105)

To a stirred solution of compound 104 (150 mg, 0.47 mmol) in CH$_2$Cl$_2$ (5 mL) under inert atmosphere was added 4 N HCl in 1,4-dioxane (3 mL) at 0° C.; warmed to RT and stirred for 3 h. The reaction was monitored by TLC; after completion of the reaction, the volatiles were removed in vacuo to obtain the crude. The crude was washed with EtOAc (2×5 mL), diethyl ether (2×5 mL) and dried in vacuo to afford compound 105 (100 mg, 84%) as an off-white solid. TLC: 10% MeOH/CH$_2$Cl$_2$ ($R_f$: 0.2); $^1$H-NMR (DMSO-$d_6$, 500 MHz): δ 9.63 (s, 1H), 9.13 (br s, 2H), 7.64 (d, J=8.1 Hz, 2H), 7.53 (dd, J=11.1, 8.2 Hz, 4H), 6.86 (d, J=8.7 Hz, 2H), 4.11 (s, 2H), 2.54 (s, 3H).

Example 26: Synthesis of 4'-(aminomethyl)-2-chloro-[1,1'-biphenyl]-4-ol (109)

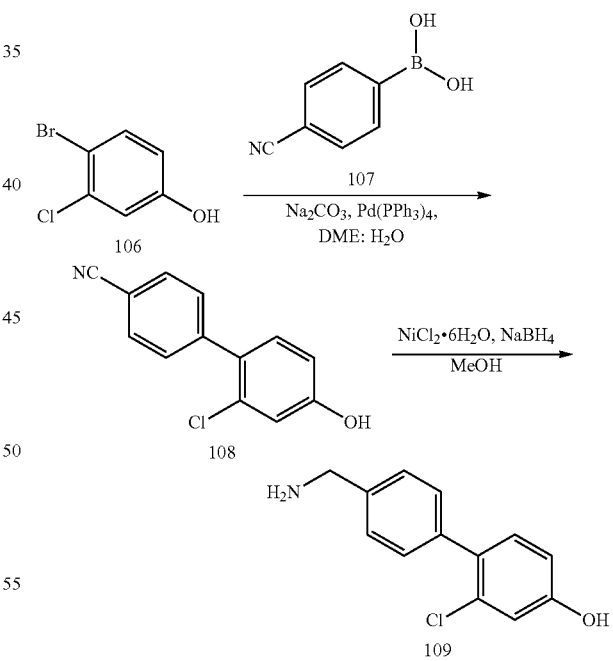

Synthesis of 2'-chloro-4'-hydroxy-[1,1'-biphenyl]-4-carbonitrile (108)

To a stirred solution of 4-bromo-3-chlorophenol 106 (500 mg, 2.41 mmol) in 1,2 dimethoxy ethane: H$_2$O (4: 1, 20 mL) under inert atmosphere were added (4-cyanophenyl) boronic acid 107 (389 mg, 2.65 mmol), sodium carbonate (766 mg, 7.23 mmol) in sealed tube and purged under argon atmosphere for 10 min. To this was added Pd(PPh$_3$)$_4$ (278 mg, 0.24 mmol) at RT; heated to 100° C. and stirred for 16 h. The reaction was monitored by TLC; after completion the reaction mixture was filtered through celite, washed with EtOAc (2×20 mL). The filtrate was dried over sodium sulfate, filtered and concentrated in vacuo to obtain the crude. The crude was purified through silica gel flash column chromatography using 20% EtOAc/hexanes. The compound was diluted in 10% sodium hydroxide solution (20 mL), washed with diethyl ether (2×10 mL) and the aqueous layer was extracted with EtOAc (2×30 mL). The combined organic extracts were dried over sodium sulfate, filtered and concentrated in vacuo to afford compound 108 (340 mg, 62%) as an off-white solid. TLC: 5% MeOH/CH$_2$Cl$_2$ (R$_f$: 0.4); $^1$H-NMR (DMSO-d$_6$, 400 MHz): δ 10.15 (br s, 1H), 7.87 (d, J=8.6 Hz, 2H), 7.58 (d, J=8.5 Hz, 2H), 7.26 (d, J=8.5 Hz, 1H), 6.94 (s, 1H), 6.84 (dd, J=8.5, 2.4 Hz, 1H).

Synthesis of 4'-(aminomethyl)-2-chloro-[1,1'-biphenyl]-4-ol (109)

To a stirred solution of compound 108 (300 mg, 1.31 mmol) in MeOH (10 mL) under argon atmosphere were added sodium borohydride (247 mg, 6.55 mmol) and nickel dichloride hexahydrate (31 mg, 0.13 mmol) at 0° C.; warmed to RT and stirred for 2.5 h. The reaction was monitored by TLC; after completion of the reaction, the reaction mixture was quenched with ice-cold water (30 mL), filtered through celite, washed with 10% MeOH/CH$_2$Cl$_2$ (2×10 mL) and the filtrate was concentrated in vacuo to afford crude. The crude was purified through silica gel column chromatography using 2% MeOH/CH$_2$Cl$_2$. The obtained compound was washed with diethyl ether (15 mL), n-pentane (10 mL) and dried in vacuo to afford compound 109 (200 mg, 66%) as an off white solid. TLC: 10% MeOH/CH$_2$Cl$_2$ (R$_f$: 0.2); $^1$H-NMR (DMSO-d$_6$, 500 MHz): δ 7.37 (d, J=7.8 Hz, 2H), 7.30 (d, J=8.7 Hz, 2H), 7.19 (d, J=8.4 Hz, 1H), 6.91 (s, 1H), 6.81 (dd, J=2.5, 8.4, 2.4 Hz, 1H), 3.76 (s, 2H). LC-MS: 95.17%; 233.9 (M$^+$+1); (column; Ascentis Express C18, (50×3.0 mm, 2.7 μm); RT 1.61 min. 0.025% Aq. TFA+5% ACN: ACN+5% 0.025% Aq. TFA, 1.2 mL/min).

Example 27: Synthesis of 4'-(aminomethyl)-2'-chloro-[1,1'-biphenyl]-4-ol (112)

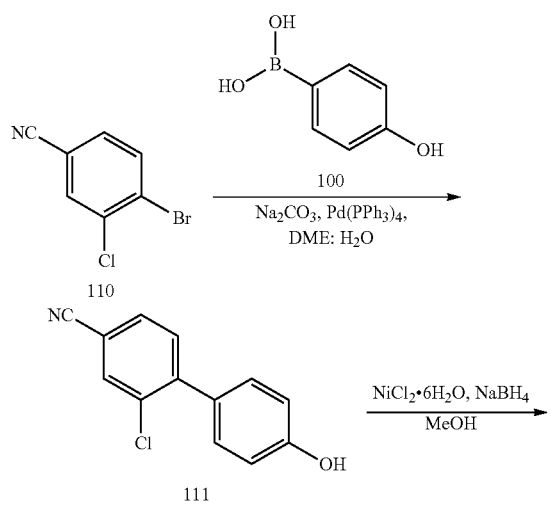

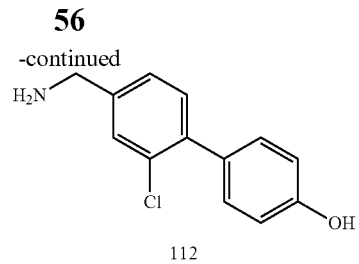

Synthesis of 2-chloro-4'-hydroxy-[1,1'-biphenyl]-4-carbonitrile (111)

To a stirred solution of 4-bromo-3-chlorobenzonitrile 110 (200 mg, 0.93 mmol) in 1,2 dimethoxy ethane: H$_2$O (3: 1, 10 mL) were added (4-hydroxyphenyl) boronic acid 100 (141 mg, 1.02 mmol), sodium carbonate (295 mg, 2.79 mmol) and purged under argon atmosphere for 20 min. To this was added Pd(PPh$_3$)$_4$ (107 mg, 0.09 mmol) at RT; heated to 80° C. and stirred for 16 h. The reaction was monitored by TLC; after completion the volatiles were removed in vacuo to obtain the crude. The crude was purified through silica gel column chromatography using 30% EtOAc/hexanes to afford compound 111 (100 mg, 47%) as an off-white solid. TLC: 30% EtOAc/hexanes (R$_f$: 0.4); $^1$H-NMR (DMSO-d$_6$, 500 MHz): δ 9.79 (s, 1H), 8.12 (s, 1H), 7.85 (dd, J=7.9, 1.7 Hz, 1H), 7.56 (d, J=8.0 Hz, 1H), 7.31 (d, J=8.7 Hz, 2H), 6.87 (d, J=8.7 Hz, 2H).

Synthesis of 4'-(aminomethyl)-2'-chloro-[1,1'-biphenyl]-4-ol (112)

To a stirred solution of compound 111 (400 mg, 1.74 mmol) in MeOH (25 mL) under argon atmosphere were added sodium borohydride (331 mg, 8.77 mmol) and nickel dichloride hexahydrate (41 mg, 0.17 mmol) at 0° C.; warmed to RT and stirred for 2.5 h. The reaction was monitored by TLC; after completion of the reaction, the reaction mixture was quenched with ice-cold water (30 mL), filtered through celite and the filtrate was concentrated in vacuo to afford compound 112 (300 mg, 73%) as an off white solid. TLC: 40% EtOAc/hexanes (R$_f$: 0.4); $^1$H-NMR (DMSO-d$_6$, 500 MHz): δ 7.45 (s, 1H), 7.27-7.24 (m, 1H), 7.12 (d, J=8.5 Hz, 1H), 6.69 (d, J=8.5 Hz, 2H), 3.70 (br s, 2H).

Example 28: Synthesis of (R)-4'(1-aminoethyl)-[1,1'-biphenyl]-4-ol (114)

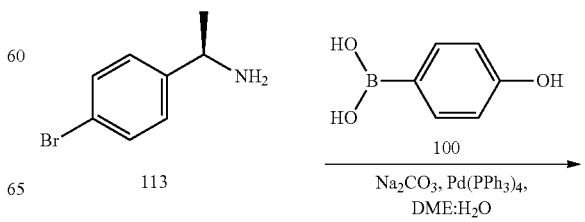

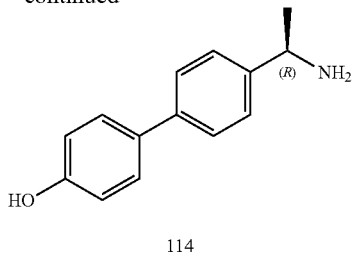

114

Synthesis of (R)-4'-(1-aminoethyl)-[1,1'-biphenyl]-4-ol (114)

To a stirred solution of (R)-1-(4-bromophenyl) ethan-1-amine 113 (500 mg, 2.50 mmol) in 1,2 dimethoxy ethane: H₂O (4: 1, 15 mL) were added (4-hydroxyphenyl) boronic acid 100 (414 mg, 3.00 mmol), sodium carbonate (927 mg, 8.75 mmol) and purged under argon atmosphere for 30 min. To this was added Pd(PPh₃)₄ (288 mg, 0.25 mmol) at RT; heated to 80-90° C. and stirred for 16 h. The reaction was monitored by TLC; after completion the reaction mixture was diluted with water (50 mL) and extracted with EtOAc (2×100 mL). The to combined organic extracts were dried over sodium sulfate, filtered and concentrated in vacuo to obtain the crude. The crude was purified through silica gel column chromatography using 10% MeOH/CH₂Cl₂ to afford compound 114 (350 mg, crude) as an off-white solid. TLC: 10% MeOH/CH₂Cl₂ (R$_f$: 0.3); LC-MS: 47.11%; 451.1 (M⁺+1); (column; Ascentis Express C18, (50×3.0 mm, 2.7 μm); RT 1.64 min. 0.025% Aq. TFA+5% ACN: ACN+5% 0.025% Aq. TFA, 1.2 mL/min);

Example 29: Synthesis of (S)-4'(1-aminoethyl)-[1,1'-biphenyl]-4-ol (116)

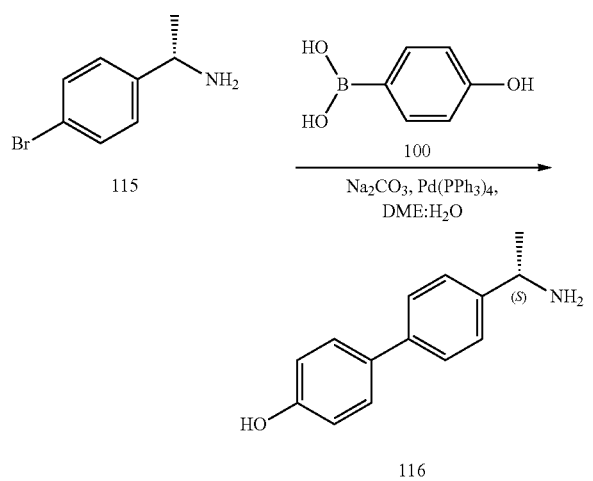

Synthesis of (S)-4'-(1-aminoethyl)-[1,1'-biphenyl]-4-ol (116)

To a stirred solution of (S)-1-(4-bromophenyl) ethan-1-amine 115 (150 mg, 0.75 mmol) in 1,2 dimethoxy ethane: H₂O (4: 1, 6 mL) were added (4-hydroxyphenyl) boronic acid 100 (124 mg, 0.90 mmol), sodium carbonate (278 mg, 2.62 mmol) and purged under argon atmosphere for 30 min. To this was added Pd(PPh₃)₄ (86 mg, 0.075 mmol) at RT; heated to 80-90° C. and stirred for 16 h. The reaction was monitored by TLC; after completion the reaction mixture was diluted with water (50 mL) and extracted with EtOAc (2×100 mL). The combined organic extracts were dried over sodium sulfate, filtered and concentrated in vacuo to obtain the crude. The crude was purified through silica gel column chromatography using 10% MeOH/CH₂Cl₂ to afford compound 116 (70 mg, 44%) as an off-white solid. TLC: 10% MeOH/CH₂Cl₂ (R$_f$: 0.3); ¹H-NMR (DMSO-d₆, 500 MHz): 9.56 (br s, 1H), 7.59-7.56 (m, 2H), 7.50-7.45 (m, 4H), 6.85 (d, J=8.7 Hz, 2H), 6.37 (br s, 2H), 4.25 (q, J=6.4 Hz, 1H), 1.42 (d, J=6.7 Hz, 3H).

Example 30: Synthesis of 2((4'-(aminomethyl)-[1,1'-biphenyll-]4-yl)oxy)-N,N-dimethylethan-1-amine hydrochloride (120)

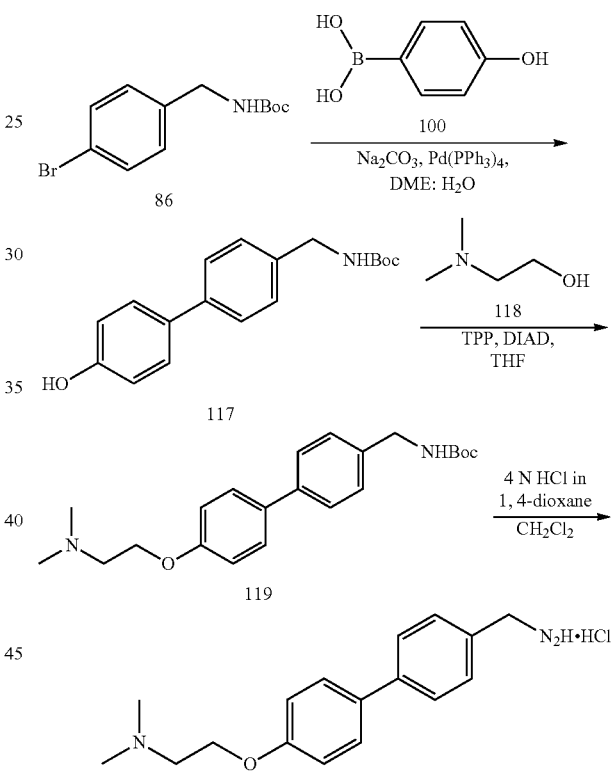

Synthesis of tert-butyl ((4'-hydroxy-[1,1'-biphenyl]-4-yl)methyl)carbamate (117)

To a stirring solution of tert-butyl (4-bromobenzyl) carbamate 86 (2 g, 6.99 mmol) in 1,2 dimethoxy ethane: H₂O (4: 1, 20 mL) were added (4-hydroxyphenyl) boronic acid 100 (1.15 g, 8.39 mmol), sodium carbonate (1.48 g, 13.98 mmol) and purged under argon atmosphere for 15 min. To this was added Pd(PPh₃)₄ (808 mg, 0.70 mmol) at RT; heated to 100° C. and stirred for 16 h. The reaction was monitored by TLC; after completion the reaction mixture was diluted with water (100 mL) and extracted with EtOAc (2×100 mL). The combined organic extracts were dried over sodium sulfate, filtered and concentrated in vacuo to obtain the crude. The crude was purified through silica gel column chromatography using 2-10% EtOAc/hexanes to afford compound 117 (800 mg, 33%) as pale brown solid. TLC: 10% EtOAc/hexanes ($R_f$: 0.3); $^1$H-NMR (DMSO-$d_6$, 400 MHz): δ 9.48 (s, 1H), 7.51 (d, J=8.2 Hz, 2H), 7.46 (d, J=8.6 Hz, 2H), 7.37 (t, J=5.8 Hz, 1H), 7.26 (d, J=8.2 Hz, 2H), 6.83 (d, J=8.6 Hz, 2H), 4.13 (d, J=6.1 Hz, 2H), 1.40 (s, 9H).

Synthesis of tert-butyl ((4'-(2-(dimethylamino) ethoxy)-[1,1'-biphenyl]-4-yl) methyl) carbamate (119)

To a compound 117 (400 mg, 1.33 mmol) in THF (10 mL) under inert atmosphere was added diisopropyl azodicarboxylate (811 mg, 4.01 mmol) and triphenyl phosphine (1 g, 4.01 mmol) at 0° C. and stirred for 10 min. To this was added 2-(dimethylamino) ethan-1-ol 118 (180 mg, 2.00 mmol) at 0° C.; warmed to RT and stirred for 16 h. The reaction was monitored by TLC and LC-MS; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silica gel column chromatography using 3% MeOH/$CH_2Cl_2$ to afford compound 119 (300 mg, 60%) as an off-white solid. TLC: 10 MeOH/$CH_2Cl_2$ ($R_f$: 0.3); $^1$H NMR (DMSO-$d_6$, 400 MHz): δ 7.56 (t, J=7.9 Hz, 5H), 7.40 (t, J=6.0 Hz, 1H), 7.28 (d, J=8.2 Hz, 2H), 7.01 (d, J=8.2 Hz, 2H), 4.14 (d, J=6.1 Hz, 2H), 4.10 (t, J=5.8 Hz, 2H), 2.70 (t, J=5.7 Hz, 2H), 2.27 (s, 6H), 1.40 (s, 9H); LC-MS: 93.71%; 371.0 (M$^+$+1); (column; Ascentis Express C18, (50×3.0 mm, 2.7 μm); RT 2.03 min. 0.025% Aq. TFA+5% ACN: ACN+5% 0.025% Aq. TFA, 1.2 mL/min).

Synthesis of 2-((4'-(aminomethyl)-[1,1'-biphenyl]-4-yl) oxy)-N, N-dimethylethan-1-amine hydrochloride (120)

To a stirring solution of compound 119 (300 mg, 0.81 mmol) in $CH_2Cl_2$ (5 mL) was added 4 N HCl in 1,4-Dioxane (5 mL) under inert atmosphere at 0° C.; warmed to RT and stirred for 3 h. The reaction was monitored by TLC; after completion of the reaction, the volatiles were removed in vacuo. The crude was washed with $CH_2Cl_2$ (5 mL), diethyl ether (5 mL) and dried in vacuo to afford compound 120 (250 mg, HCl salt) as an off-white solid. TLC: 50% EtOAc/hexanes ($R_f$: 0.2); $^1$H-NMR (DMSO-$d_6$, 400 MHz): δ 10.49 (br s, 1H), 8.39 (br s, 3H), 7.67 (dd, J=5.9, 8.5 Hz, 4H), 7.54 (d, J=8.3 Hz, 2H), 7.11 (d, J=8.8 Hz, 2H), 4.41 (t, J=5.0 Hz, 2H), 4.08-4.02 (m, 2H), 3.52 (t, J=4.5 Hz, 2H), 2.85 (s, 6H); LC-MS: 99.61%; 271.3 (M$^+$+1); (column; X-select CSH C-18 (150×3 mm, 2.5 μm); RT 2.28 min. 2.5 mM Aq. NH$_4$OAc: ACN; 0.8 mL/min).

Example 31: Synthesis of tert-butyl ((3'-hydroxy-[1,1'-biphenyl]-4-yl)methyl)carbamate (122)

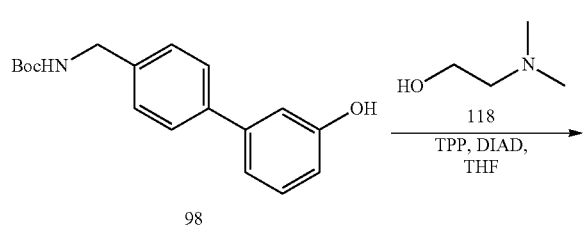

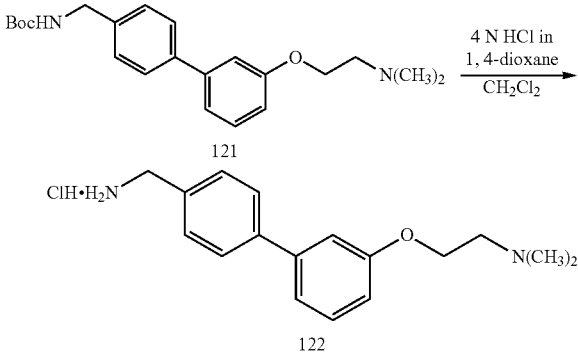

Synthesis of tert-butyl ((3'-(2-(dimethylamino) ethoxy)-[1,1'-biphenyl]-4-yl)methyl) carbamate (121)

To a stirred solution of triphenyl phosphine (1.75 g, 6.68 mmol) and diisopropyl azodicarboxylate (1.35 g, 6.68 mmol) in THF (5 mL) under inert atmosphere was added compound 98 (400 mg, 1.33 mmol) and 2-(dimethylamino) ethan-1-ol 118 (178 mg, 2.00 mmol) at 0° C.; warmed to RT and stirred for 16 h. The reaction was monitored by TLC; after completion of the reaction, the volatiles were removed in vacuo to obtain the crude. The crude was purified through silica gel flash column chromatography using 50% EtOAc/hexanes-10% to MeOH/$CH_2Cl_2$ to afford compound 121 (300 mg, crude) as colorless liquid. TLC: 10% MeOH/$CH_2Cl_2$ ($R_f$: 0.4); LC-MS: 60.86%; 371.1 (M$^+$+1); (column; Ascentis Express C18, (50×3.0 mm, 2.7 μm); RT 1.75 min. 0.025% Aq. TFA+5% ACN: ACN+5% 0.025% Aq. TFA, 1.2 mL/min).

Synthesis of 2-((4'-(aminomethyl)-[1,1'-biphenyl]-3-yl) oxy)-N,N-dimethylethan-1-amine hydrochloride (122)

To a stirred solution of compound 121 (300 mg, 0.81 mmol) in $CH_2Cl_2$ (10 mL) under inert atmosphere was added 4 N HCl in 1,4-dioxane (3 mL) at 0° C.; warmed to RT and stirred for 3 h. The reaction was monitored by TLC; after completion of the reaction, the volatiles were removed in vacuo to obtain the crude. The crude was washed with EtOAc (2×5 mL), diethyl ether (2×5 mL) and dried in vacuo to afford compound 122 (300 mg, 92%) as an off-white solid. TLC: 10% MeOH/$CH_2Cl_2$ ($R_f$: 0.2); $^1$H-NMR (DMSO-$d_6$, 400 MHz): δ 8.46 (br s, 3H), 7.74 (d, J=8.3 Hz, 2H), 7.59 (d, J=8.2 Hz, 2H), 7.43 (t, J=8.4 Hz, 1H), 7.36-7.27 (m, 2H), 7.03 (dd, J=8.1, 1.7 Hz, 1H), 4.46 (t, J=5.1 Hz, 2H), 4.09-4.03 (m, 2H), 3.57 (s, 6H), 2.82 (t, J=4.8 Hz, 2H).

Example 32: Synthesis of 3-(3-(aminomethyl)benzyl)phenol hydrochloride (125)

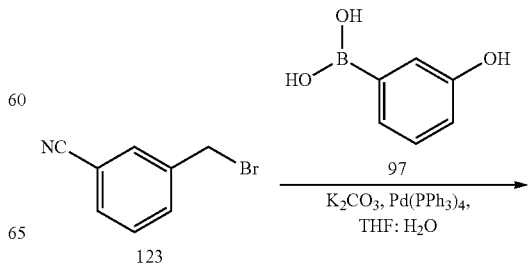

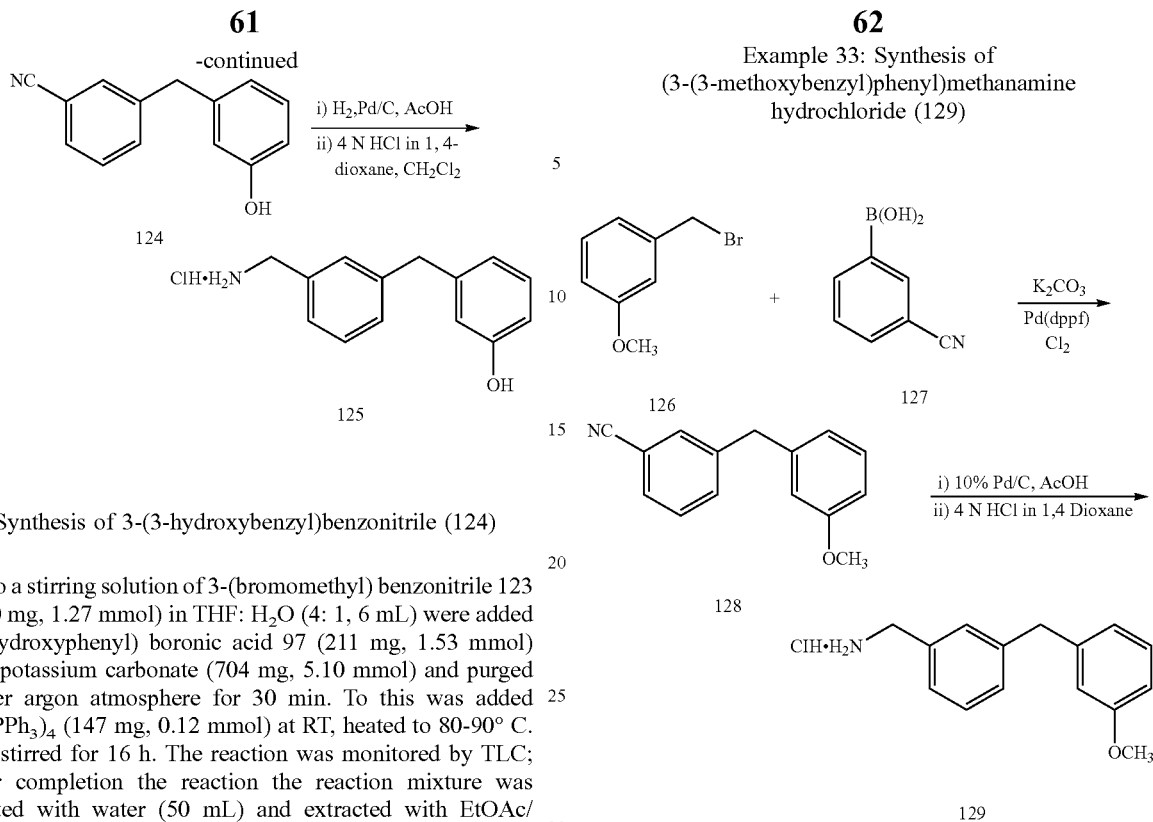

Synthesis of 3-(3-hydroxybenzyl)benzonitrile (124)

To a stirring solution of 3-(bromomethyl) benzonitrile 123 (250 mg, 1.27 mmol) in THF: H$_2$O (4: 1, 6 mL) were added (3-hydroxyphenyl) boronic acid 97 (211 mg, 1.53 mmol) and potassium carbonate (704 mg, 5.10 mmol) and purged under argon atmosphere for 30 min. To this was added Pd(PPh$_3$)$_4$ (147 mg, 0.12 mmol) at RT, heated to 80-90° C. and stirred for 16 h. The reaction was monitored by TLC; after completion the reaction the reaction mixture was diluted with water (50 mL) and extracted with EtOAc/hexanes (2×100 mL). The combined organic extracts were dried over sodium sulfate, filtered and concentrated in vacuo to obtain the crude. The crude was purified through silica gel column chromatography using 10% EtOAc/hexanes to afford compound 124 (135 mg, 51%) as thick syrup. TLC: 20% EtOAc/hexanes (R$_f$: 0.6); $^1$H NMR (DMSO-d$_6$, 400 MHz): δ 9.29 (s, 1H), 7.70 (s, 1H), 7.66 (dt, J=7.5, 1.4 Hz, 1H), 7.57 (dd, J=7.7, 1.6 Hz, 1H), 7.53-7.47 (m, 1H), 7.11-7.06 (m, 1H), 6.66 (d, J=7.7 Hz, 1H), 6.61-6.57 (m, 2H), 3.91 (s, 2H).

Synthesis of 3-(3-(aminomethyl)benzyl)phenol hydrochloride (125)

To a stirring solution of compound 124 (125 mg, 0.59 mmol) in acetic acid (5 mL) under inert atmosphere was added 10% Pd/C (30 mg) at RT and stirred under hydrogen atmosphere (balloon pressure) at RT for 16 h. The reaction was monitored by TLC; after completion of the reaction, the reaction mixture was filtered through celite and washed with MeOH (50 mL). The filtrate was concentrated in vacuo to obtain the crude compound.

To the above crude compound under inert atmosphere was added 4 N HCl in 1,4-dioxane (1.5 mL) at 0° C.; warmed to RT and stirred for 2 h. The reaction was monitored by TLC; after completion of the reaction, the volatiles were removed in vacuo to obtain the crude. The crude was washed with EtOAc (2×5 mL) and dried in vacuo to afford compound 125 (115 mg) as an off-white solid. TLC: 10% MeOH/CH$_2$Cl$_2$ (R$_f$: 0.2); $^1$H-NMR (DMSO-d$_6$, 400 MHz): δ 9.33 (br s, 1H), 8.39 (br s, 2H), 7.44-7.15 (m, 5H), 7.06 (t, J=7.8 Hz, 1H), 6.69-6.55 (m, 2H), 3.97 (q, J=5.6 Hz, 1H), 3.84 (s, 1H), 3.57 (s, 3H); LC-MS: 85.51%; 213.9 (M$^+$+1); (column; Ascentis Express C18, (50×3.0 mm, 2.7 μm); RT 1.57 min. 0.025% Aq. TFA+5% ACN: ACN+5% 0.025% Aq. TFA, 1.2 mL/min).

Example 33: Synthesis of (3-(3-methoxybenzyl)phenyl)methanamine hydrochloride (129)

Synthesis of 3-(3-methoxybenzyl)benzonitrile (128)

To a stirring solution of 1-(bromomethyl)-3-methoxybenzene 126 (1 g, 4.97 mmol) in THF: H$_2$O (4: 1, 20 mL) were added potassium carbonate (2.74 g, 19.90 mmol), (3-cyanophenyl) boronic acid 127 (877 mg, 5.97 mmol) and purged under argon atmosphere for 15 min. To this was added Pd(dppf)Cl$_2$ (363 mg, 0.49 mmol) and purged under argon atmosphere for 10 min at RT; heated to 100° C. and stirred for 16 h. The reaction was monitored by TLC; after completion of the reaction, the reaction mixture diluted with water (60 mL) and extracted with EtOAc (2×50 mL). The combined organic extracts were dried over sodium sulfate, filtered and concentrated in vacuo to obtain the crude. The crude was purified through silica gel column chromatography using 7% EtOAc/hexanes to afford compound 128 (610 mg, 55%) as colorless syrup. TLC: 30% EtOAc/hexanes (R$_f$: 0.5); $^1$H NMR (DMSO-d$_6$, 400 MHz): δ 7.74-7.72 (m, 1H), 7.66 (td, J=7.6, 1.3 Hz, 1H), 7.59 (td, J=7.9, 1.1 Hz, 1H), 7.50 (t, J=7.7 Hz, 1H), 7.21 (t, J=7.9 Hz, 1H), 6.91-6.74 (m, 3H), 3.97 (s, 2H), 3.32 (s, 3H).

Synthesis of (3-(3-methoxybenzyl) phenyl)methanamine hydrochloride (129)

To a stirring solution of 3-(3-methoxybenzyl) benzonitrile 128 (600 mg, 2.69 mmol) in acetic acid (15 mL) under argon atmosphere was added 10% Pd/C (200 mg, dry) at RT and stirred under hydrogen atmosphere (balloon pressure) at RT for 6 h. The reaction was monitored by TLC; after completion of the reaction, the reaction mixture was diluted with EtOAc (50 mL), filtered through celite and washed with 5% MeOH/CH$_2$Cl$_2$ (100 mL). The filtrate was concentrated in vacuo to obtain the crude.

The above crude was dissolved in $CH_2Cl_2$ (5 mL) under argon atmosphere was added 4 N HCl in 1,4-dioxane (5 mL) at 0° C.; warmed to RT and stirred for 2 h. The volatiles were removed in vacuo. The crude was washed with EtOAc (2×20 mL), pentane (20 mL) and dried in vacuo to afford compound 129 (520 mg, 74%) as color less syrup. TLC: 50% EtOAc/hexanes ($R_f$: 0.2); $^1$H NMR (DMSO-$d_6$, 400 MHz): δ 8.14 (br s, 3H), 7.38-7.16 (m, 6H), 6.91-6.69 (m, 3H), 3.98 (s, 2H), 3.91 (s, 2H), 3.72 (s, 3H); LC-MS: 99.95%; 227.9 ($M^+$+1) (column; Ascentis Express C-18 (50×3.0 mm, 2.7 μm); RT 1.82 min. 0.025% Aq.TFA+5% ACN: ACN+5% 0.025% Aq TFA, 1.2 mL/min).

Example 34: Synthesis of 3-(4-methoxybenzyl)phenyl)methanamine hydrochloride (132)

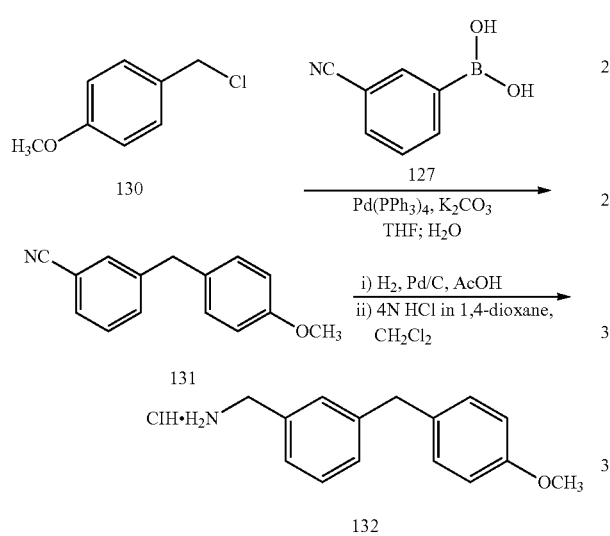

Synthesis of 3-(4-methoxybenzyl) benzonitrile (131)

To a stirring solution of 1-(chloromethyl)-4-methoxybenzene 130 (1 g, 6.41 mmol) in THF: $H_2O$ (4: 1, 20 mL) were added (3-cyanophenyl) boronic acid 127 (1.13 g, 7.69 mmol) and potassium carbonate (3.53 g, 25.64 mmol) and purged under argon atmosphere for 30 min. To this was added $Pd(PPh_3)_4$ (740 mg, 0.64 mmol) at RT, heated to 80-90° C. and stirred for 16 h. The reaction was monitored by TLC; after completion the reaction the reaction mixture was diluted with water (50 mL) and extracted with EtOAc/hexanes (2×100 mL). The combined organic extracts were dried over sodium sulfate, filtered and concentrated in vacuo to obtain the crude. The crude was purified through silica gel column chromatography using 7% EtOAc/hexanes to afford compound 131 (650 mg, 46%) as white solid. TLC: 10% EtOAc/hexanes ($R_f$: 0.5); $^1$H NMR (DMSO-$d_6$, 400 MHz): δ 10.63 (s, 1H), 9.17 (br t, J=5.6 Hz, 1H), 8.58 (d, J=2.0 Hz, 1H), 7.92 (dd, J=2.3, 9.0, 2.3 Hz, 1H), 7.78 (d, J=7.2 Hz, 1H), 7.70-7.59 (m, 4H), 7.42 (d, J=8.4 Hz, 1H), 7.39-7.31 (m, 2H), 6.70 (d, J=9.0 Hz, 1H), 4.62 (br d, J=5.5 Hz, 2H), 3.08 (s, 6H);

Synthesis of (3-(4-methoxybenzyl) phenyl) methanamine hydrochloride (132)

To a stirring solution of compound 131 (150 mg, 0.67 mmol) in acetic acid (5 mL) to under inert atmosphere was added 10% Pd/C (50 mg) at RT and stirred under hydrogen atmosphere (balloon pressure) at RT for 16 h. The reaction was monitored by TLC; after completion of the reaction, the reaction mixture was filtered through celite and washed with MeOH (50 mL). The filtrate was concentrated in vacuo to obtain the crude compound.

To the above crude compound under inert atmosphere was added 4 N HCl in 1,4-dioxane (1.5 mL) at 0° C.; warmed to RT and stirred for 30 min. The reaction was monitored by TLC; after completion of the reaction, the volatiles were removed in vacuo to obtain the crude. The crude was washed with EtOAc (2×5 mL) and dried in vacuo to afford compound 132 (100 mg, 56%) as white solid. TLC: 10% MeOH/$CH_2Cl_2$ ($R_f$: 0.2); $^1$1-NMR (DMSO-$d_6$, 500 MHz): δ 8.00 (br s, 3H), 7.35-7.28 (m, 3H), 7.22 (d, J=7.2 Hz, 1H), 7.14 (d, J=8.7 Hz, 2H), 6.85 (d, J=8.4 Hz, 2H), 3.97 (s, 2H), 3.87 (s, 2H), 3.71 (s, 3H); LC-MS: 79.31%; 227.9 ($M^+$+1); (column; Ascentis Express C18, (50×3.0 mm, 2.7 μm); RT 1.80 min. 0.025% Aq. TFA+5% ACN: ACN+5% 0.025% Aq. TFA, 1.2 mL/min).

Example 35: Synthesis of (3-(3-methoxyphenoxy)phenyl)methanamine hydrochloride (136)

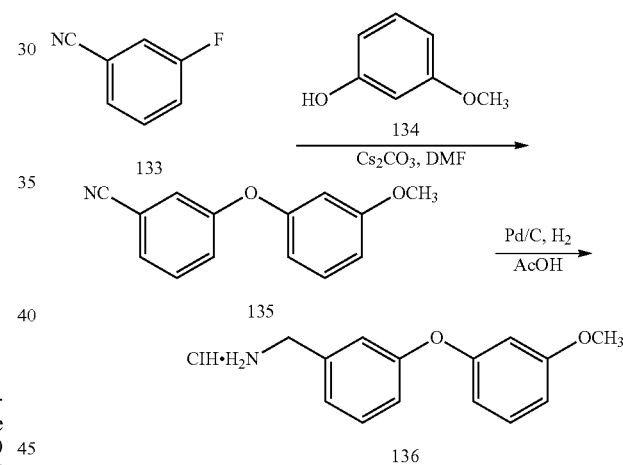

Synthesis of 3-(3-methoxyphenoxy) benzonitrile (135) (SAP-MA1521-36)

To a stirring solution of 3-fluorobenzonitrile 133 (1 g, 8.25 mmol) in DMF (20 mL) under argon atmosphere were added 3-methoxyphenol 134 (1.02 g, 8.25 mmol), cesium carbonate (4.0 g, 12.38 mmol) at RT; heated to 140° C. and stirred for 4 h. The reaction was monitored by TLC; after completion of the reaction, the reaction mixture was diluted with water (50 mL) and extracted with EtOAc (2×60 mL). The combined organic extracts were dried over sodium sulfate, filtered and concentrated in vacuo to obtain the crude. The crude was purified through silica gel (100-200 mesh) flash column chromatography using 7-10% EtOAc/hexanes to afford compound 135 (850 mg, 46%) as colorless syrup. TLC: 20% EtOAc/hexanes ($R_f$: 0.5); 1H-NMR (DMSO-d6, 400 MHz): δ 7.63-7.54 (m, 2H), 7.48 (dd, J=2.7, 1.1 Hz, 1H), 7.36-7.30 (m, 2H), 6.81-6.78 (m, 1H), 6.67 (t, J=2.3 Hz, 1H), 6.63-6.60 (m, 1H), 3.75 (s, 3H);

Synthesis of (3-(3-methoxyphenoxy) phenyl) methanamine hydrochloride (136)

To a stirring solution of compound 135 (1 g, 4.46 mmol) in acetic acid (15 mL) under inert atmosphere was added 10% Pd/C (300 mg) at RT and stirred under hydrogen atmosphere (balloon pressure) at RT for 16 h. The reaction was monitored by TLC; after completion of the reaction, the reaction mixture was filtered through celite and washed with 50% MeOH/CH$_2$Cl$_2$ (3×40 mL). The filtrate was concentrated in vacuo to obtain the crude amine.

The above crude amine was in CH$_2$Cl$_2$ (15 mL) under inert atmosphere was added 4 N HCl in 1,4-dioxane (5 mL) at 0° C. and stirred for 1 h. The volatiles were removed in vacuo and the obtained crude was washed with diethylether (20 mL) and dried in vacuo to afford compound 136 (600 mg, 51%) as an off-white solid. TLC: 5% MeOH/CH$_2$Cl$_2$ (R$_f$: 0.4); $^1$H NMR (DMSO-d$_6$, 400 MHz): δ 7.71 (br s, 3H), 7.45-7.37 (m, 1H), 7.32-7.25 (m, 2H), 7.23 (s, 1H), 6.99 (dd, J=8.0, 1.8 Hz, 1H), 6.78-6.67 (m, 1H), 6.59-6.52 (m, 2H), 3.99 (s, 2H), 3.73 (s, 3H); LC-MS: 96.34%; 229.9 (M$^+$+1); (column; Ascentis Express C18, (50×3.0 mm, 2.7 μm); RT 1.77 min. 0.025% Aq. TFA+5% ACN: ACN+5% 0.025% Aq. TFA, 1.2 mL/min).

Example 36: Synthesis of (3-(4-methoxyphenoxy)phenyl)methanamine (139)

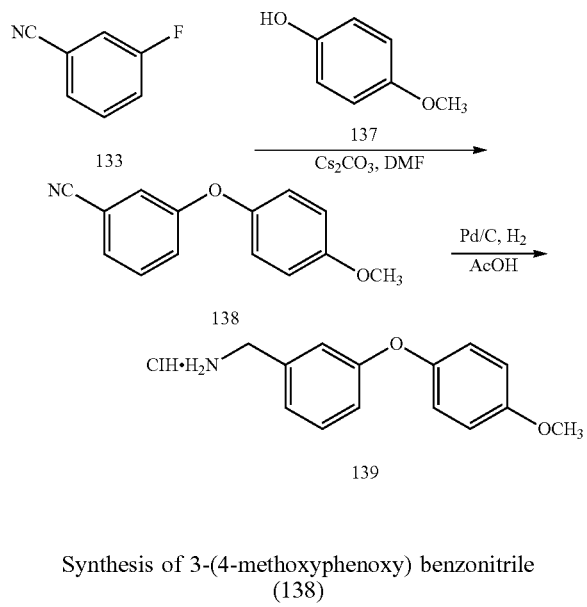

Synthesis of 3-(4-methoxyphenoxy) benzonitrile (138)

To a stirring solution of 3-fluorobenzonitrile 133 (1 g, 8.25 mmol) in DMF (20 mL) under argon atmosphere were added 4-methoxyphenol 137 (1.02 g, 8.25 mmol), cesium carbonate (4.0 g, 12.38 mmol) at RT and stirred for 16 h. The reaction was monitored by TLC; after completion of the reaction, the reaction mixture was diluted with water (50 mL) and extracted with EtOAc (2×60 mL). The combined organic extracts were dried over sodium sulfate, filtered and concentrated in vacuo to obtain the crude. The crude was purified through silica gel flash column chromatography using 7-10% EtOAc/hexanes to afford compound 138 (850 mg, 46%) as white solid. TLC: 20% EtOAc/hexanes (R$_f$: 0.4); $^1$H NMR (DMSO-d$_6$, 500 MHz): δ 7.56-7.49 (m, 2H), 7.34 (s, 1H), 7.23 (dd, J=7.5, 2.0 Hz, 1H), 7.06 (d, J=8.7 Hz, 2H), 6.99 (d, J=9.0 Hz, 2H), 3.76 (s, 3H); LC-MS: 83.43%; 224.9 (M$^+$); (column; Ascentis Express C18, (50×3.0 mm, 2.7 μm); RT 2.70 min. 0.025% Aq. TFA+5% ACN: ACN+5% 0.025% Aq. TFA, 1.2 mL/min).

Synthesis of (3-(4-methoxyphenoxy)phenyl)methanamine hydrochloride (139)

To a stirring solution of compound 138 (700 mg, 3.12 mmol) in acetic acid (15 mL) under inert atmosphere was added 10% Pd/C (250 mg) at RT and stirred under hydrogen atmosphere (balloon pressure) at RT for 16 h. The reaction was monitored by TLC; after completion of the reaction, the reaction mixture was filtered through celite and washed with 50% MeOH/CH$_2$Cl$_2$ (3×30 mL). The filtrate was concentrated in vacuo to obtain the crude amine.

The above crude amine was in CH$_2$Cl$_2$ (10 mL) under inert atmosphere was added 4 N HCl in 1,4-dioxane (3 mL) at 0° C. and stirred for 1 h. The volatiles were removed in vacuo and the obtained crude was triturated with EtOAc (10 mL) and dried in vacuo to afford compound 139 (400 mg, 48%) as an off-white solid. TLC: 20% EtOAc/hexanes (R$_f$: 0.2); $^1$H NMR (DMSO-d$_6$, 400 MHz): δ 8.13 (br s, 3H), 7.40-7.35 (m, 1H), 7.19 (d, J=7.7 Hz, 1H), 7.12 (s, 1H), 7.03-6.95 (m, 4H), 6.90 (dd, J=8.2, 1.9 Hz, 1H), 3.98 (s, 2H), 3.76 (s, 3H); LC-MS: 92.35%; 230.0 (M$^+$+1); (column; Ascentis Express C18, (50×3.0 mm, 2.7 μm); RT 1.77 min. 0.025% Aq. TFA+5% ACN: ACN+5% 0.025% Aq. TFA, 1.2 mL/min).

Example 37: Synthesis of (3-((3-methoxyphenyl)thio)phenyl)methanamine hydrochloride (143)

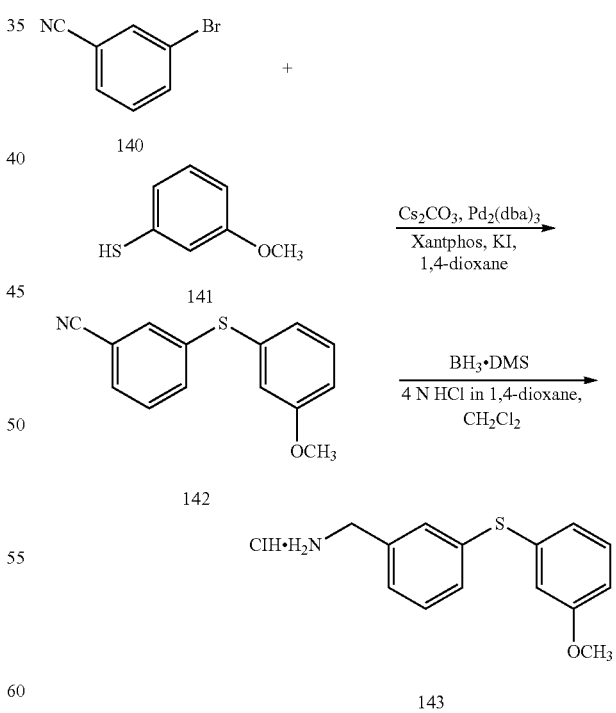

Synthesis of 3-((3-methoxyphenyl)thio)benzonitrile (142)

To a stirring solution of 3-bromobenzonitrile 140 (1 g, 5.49 mmol) in 1,4-dioxane (25 mL) were added 3-methoxybenzenethiol 141 (1.2 g, 8.24 mmol), and cesium carbonate (5.4 g, 16.49 mmol) at RT in a sealed tube and purged under argon atmosphere for 15 min. To this were added potassium iodide (912 mg, 5.49 mmol), Pd$_2$(dba)$_3$ (251 mg, 0.27 mmol), Xantphos (222 mg, 0.38 mmol) at RT; heated to 110° C. and stirred for 16 h. The reaction was monitored by TLC; after completion of the reaction, the reaction mixture was filtered through celite, washed with CH$_2$Cl$_2$ (2×30 mL). The organic extract was dried over sodium sulfate, filtered and concentrated in vacuo to obtain the crude. The crude was purified through silica gel column chromatography using 2-10% EtOAc/hexanes to afford compound 142 (1.1 g, 85%) as pale yellow thick syrup. TLC: 10% EtOAc/hexanes (R$_f$: 0.4); $^1$H-NMR (CDCl$_3$, 400 MHz): δ 7.49-7.43 (m, 3H), 7.38-7.25 (m, 2H), 7.05-6.88 (m, 3H), 3.80 (s, 3H);

Synthesis of
(3-((3-methoxyphenyl)thio)phenyl)methanamine
hydrochloride (143)

To a stirring solution of compound 142 (200 mg, 0.83 mmol) in THF (5 mL) under inert atmosphere was added borane dimethyl sulfide complex (0.33 mL, 1.66 mmol) dropwise for 15 min at 0° C.; warmed to RT and stirred for 16 h. The reaction was monitored by TLC; after completion of the reaction, the reaction mixture was quenched with MeOH (5 mL) and refluxed for 2 h. The volatiles were removed in vacuo to obtain the crude compound (200 mg).

To the above crude compound (200 mg) in CH$_2$Cl$_2$ (10 mL) under inert atmosphere was added 4 N HCl in 1,4-dioxane (2 mL) at 0° C.; warmed to RT and stirred for 2 h. The reaction was monitored by TLC; after completion of the reaction, the volatiles were removed in vacuo to obtain the crude which was triturated with diethyl ether (3×25 mL) and dried in vacuo to afford compound 143 (120 mg). TLC: 10% MeOH/CH$_2$Cl$_2$ (R$_f$: 0.4). $^1$H-NMR (DMSO-d$_6$, 500 MHz): δ 8.44 (br s, 3H), 7.57 (br s, 1H), 7.49-7.41 (m, 2H), 7.36-7.26 (m, 2H), 6.88 (t, J=6.5 Hz, 2H), 6.84 (br s, 1H), 4.01 (br s, 2H), 3.73 (s, 3H).

Example 38: Synthesis of
(3-((4-methoxyphenyl)thio)phenyl)methanamine
hydrochloride (146)

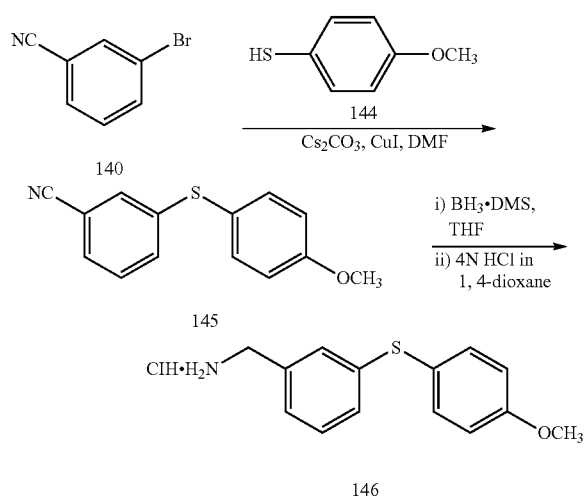

Synthesis of 3-((4-methoxyphenyl)thio)benzonitrile
(145)

To a stirring solution of 3-bromobenzonitrile 140 (1 g, 5.49 mmol) in DMF (20 mL) under argon atmosphere were added cesium carbonate (5.40 g, 16.48 mmol), 4-methoxybenzenethiol 144 (769 mg, 5.49 mmol) in a sealed tube at RT; heated to 70° C. and stirred for 16 h. The reaction was monitored by TLC; after completion of the reaction, reaction mixture was diluted with water (200 mL) and extracted with EtOAc (2×100 mL). The combined organic extracts were dried over sodium sulfate, filtered and concentrated in vacuo to obtain the crude. The crude was purified through silica gel flash column chromatography using 5% EtOAc/hexanes to afford compound 145 (230 mg, 17%) as an off-white solid. TLC: 10% EtOAc/hexanes (R$_f$: 0.4); $^1$H NMR (DMSO-d$_6$, 400 MHz): δ 7.62 (dt, J=7.8, 1.3 Hz, 1H), 7.53-7.45 (m, 4H), 7.39-7.35 (m, 1H), 7.07 (d, J=8.9 Hz, 2H), 3.81 (s, 3H).

Synthesis of
(3-((4-methoxyphenyl)thio)phenyl)methanamine
hydrochloride (146)

To a stirring solution of compound 145 (230 mg, 0.95 mmol) in THF (5 mL) under inert atmosphere was added borane dimethyl sulfide complex (0.4 mL, 1.90 mmol, 5.0 M solution in ether) dropwise for 5 min at 0° C.; warmed to RT and stirred for 6 h. The reaction was monitored by TLC; after completion of the reaction, the reaction mixture was quenched with MeOH (5 mL); heated to 60° C. and stirred for 1 h.

To the above reaction mixture under inert atmosphere was added 4 N HCl in 1,4-dioxane (2 mL) at 0° C.; warmed to RT and stirred for 1 h. The reaction was monitored by TLC; after completion of the reaction, the volatiles were removed in vacuo to obtain the crude which was triturated with diethylether (2×5 mL) and dried in vacuo to afford compound 146 (170 mg, 63%). TLC: 5% MeOH/CH$_2$Cl$_2$ (R$_f$: 0.1). $^1$H-NMR (DMSO-d$_6$, 500 MHz): δ 8.37 (br s, 3H), 7.42 (d, J=8.7 Hz, 2H), 7.38-7.30 (m, 3H), 7.06 (dt, J=6.9, 1.7 Hz, 1H), 7.02 (d, J=8.7 Hz, 2H), 3.96 (q, J=5.5 Hz, 2H), 3.79 (s, 3H); LC-MS: 93.31%; 245.8 (M$^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min).

Example 39: Compound Preparation

Acids similar to compound 6 (compounds 9, 14, 19, 22, 25) were synthesized as mentioned above and converted to final products either using commercially available amines or prepared amines employing typical procedure A and the results are captured in the Table 1:

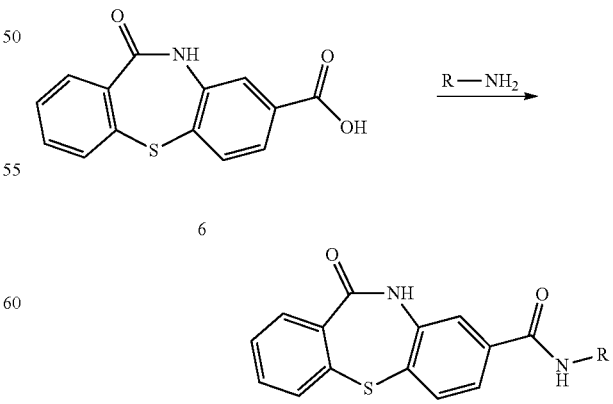

Typical Procedure A:

To a stirred solution of compound 6 (100 mg, 0.37 mmol) in DMF (5 mL) under inert atmosphere were added EDCI.HCl (95 mg, 0.55 mmol), HOBt (71 mg, 0.55 mmol), amine 27 (81 mg, 0.44 mmol) and diisopropylethylamine (0.2 mL, 1.05 mmol) at 0° C. warmed to RT and stirred for 16 h. The reaction was monitored by TLC; after completion of the reaction, the volatiles were removed in vacuo to obtain the crude. The crude was either directly dried in vacuo or triturated or purified through silica gel column chromatography to afford the desired compound.

TABLE 1

| Compound No. | Structure | Procedure, Intermediate amine | Rx. Yield (%) | Mass Spec. Found | Mass Spec. Calculated | $^1$H-NMR |
|---|---|---|---|---|---|---|
| 537 | 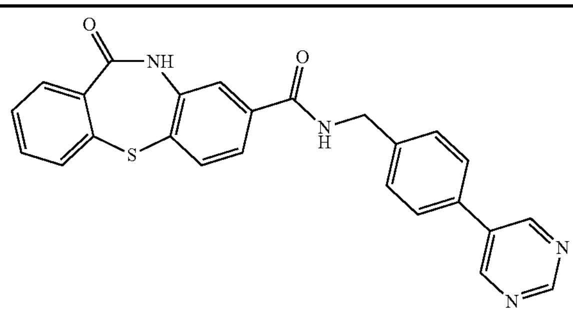 | A, 6, 83 | 56 | 439.0 (M$^+$ + 1); | 438.12 for $C_{25}H_{18}N_4O_2S$ | $^1$H-NMR (DMSO-$d_6$, 400 MHz): δ 10.77 (s, 1H), 9.18-9.10 (m, 4H), 7.78-7.72 (m, 3H), 7.71-7.63 (m, 3H), 7.57-7.42 (m, 5H), 4.51 (d, J = 6.0 Hz, 2H); |
| 538 | 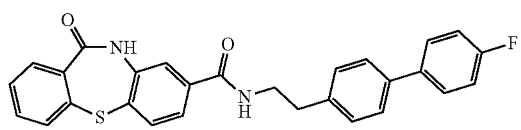 [SMILES: O=C(NCCc1ccc(-c2ccc(F)cc2)cc1)c1ccc2c(c1)NC(=O)c1ccccc1S2] | A, 6, 94 | 84 | 469.0 (M$^+$ + 1); | 468.13 for $C_{28}H_{21}FN_2O_2S$ | $^1$H-NMR (DMSO-$d_6$, 400 MHz): δ 10.78 (s, 1H), 8.63 (t, J = 5.2 Hz, 1H), 7.71-7.63 (m, 5H), 7.59-7.51 (m, 4H), 7.50-7.43 (m, 2H), 7.34-7.22 (m, 4H), 3.49 (q, J = 6.4 Hz, 2H), 2.85 (t, J = 7.0 Hz, 2H); |
| 565 | 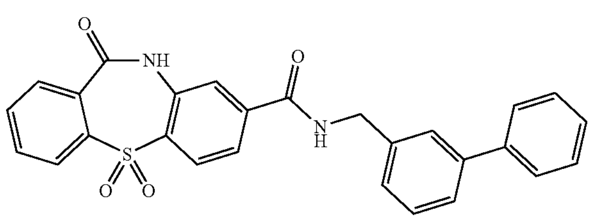 [SMILES: O=C(NCc1cccc(-c2ccccc2)c1)c1ccc2c(c1)NC(=O)c1ccccc1S2(=O)=O] | A, 9, 86 | 33 | 469.1 (M$^+$ + 1); | 468.11 for $C_{27}H_{20}N_2O_4S$ | $^1$H-NMR (DMSO-$d_6$, 500 MHz): δ 11.49 (s, 1H), 9.29 (t, J = 5.5 Hz, 1H), 8.04 (d, J = 8.1 Hz, 1H), 8.00-7.93 (m, 2H), 7.92-7.79 (m, 4H), 7.63-7.57 (m, 3H), 7.52 (d, J = 7.5 Hz, 1H), 7.48-7.37 (m, 3H), 7.37-7.32 (m, 1H), 7.28 (d, J = 7.2 Hz, 1H), 4.54-4.52 (m, 2H); |
| 563 | 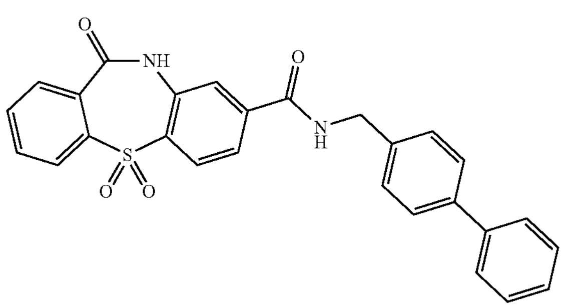 [SMILES: O=C(NCc1ccc(-c2ccccc2)cc1)c1ccc2c(c1)NC(=O)c1ccccc1S2(=O)=O] | A, 9, 27 | 19 | 469.2 (M$^+$ + 1); | 468.11 for $C_{27}H_{20}N_2O_4S$ | $^1$H-NMR (DMSO-$d_6$, 400 MHz): δ 11.51 (s, 1H), 9.31 (t, J = 5.8 Hz, 1H), 8.06 (d, J = 8.2 Hz, 1H), 8.01-7.96 (m, 2H), 7.91 (dd, J = 7.5, 1.6 Hz, 1H), 7.89-7.83 (m, 3H), 7.65-7.59 (m, 4H), 7.47-7.42 (m, 2H), 7.39 (d, J = 8.4 Hz, 2H), 7.37-7.32 (m, 1H), 4.51 (d, J = 5.9 Hz, 2H); |

TABLE 1-continued

| Compound No. | Structure | Procedure, Intermediate amine | Rx. Yield (%) | Mass Spec. Found | Mass Spec. Calculated | 1H-NMR |
|---|---|---|---|---|---|---|
| 566 | 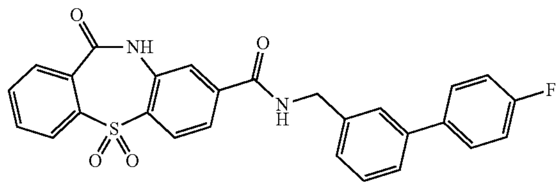 [SMILES: O=C(NCc1cccc(-c2ccc(F)cc2)c1)c1ccc2c(c1)NC(=O)c1ccccc1S2(=O)=O] | A, 9, 96 | 34 | 486.9 (M+ + 1); | 486.10 for C27H19FN2O4S | 1H-NMR (DMSO-d6, 400 MHz): δ 11.52 (s, 1H), 9.31 (t, J = 5.7 Hz, 1H), 8.06 (d, J = 8.5 Hz, 1H), 8.01-7.95 (m, 2H), 7.93-7.82 (m, 4H), 7.66 (dd, J = 8.8, 5.5 Hz, 2H), 7.59-7.56 (m, 1H), 7.52 (d, J = 7.8 Hz, 1H), 7.41 (t, J = 7.6 Hz, 1H), 7.32-7.25 (m, 3H), 4.54 (d, J = 5.9 Hz, 2H); |
| 564 | 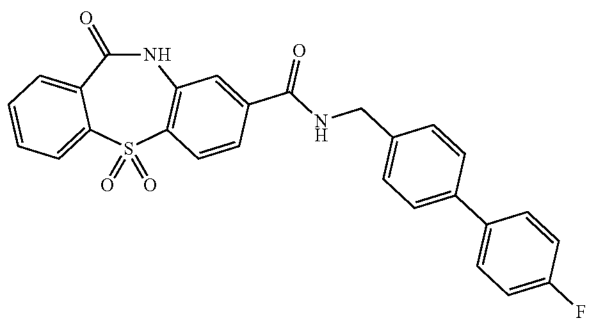 [SMILES: O=C(NCc1ccc(-c2ccc(F)cc2)cc1)c1ccc2c(c1)NC(=O)c1ccccc1S2(=O)=O] | A, 9, 94 | 25 | 487.0 (M+ + 1); | 486.10 for C27H19FN2O4S | 1H-NMR (DMSO-d6, 400 MHz): δ 11.54 (s, 1H), 9.34 (t, J = 6.1 Hz, 1H), 8.09 (d, J = 8.2 Hz, 1H), 8.02 (td, J = 7.9, 1.1 Hz, 2H), 7.96-7.86 (m, 4H), 7.70 (dd, J = 5.5, 8.7 Hz, 2H), 7.62 (d, J = 8.3 Hz, 2H), 7.41 (d, J = 8.2 Hz, 2H), 7.30 (t, J = 8.9 Hz, 2H), 4.53 (d, J = 5.7 Hz, 2H); |
| 639 | 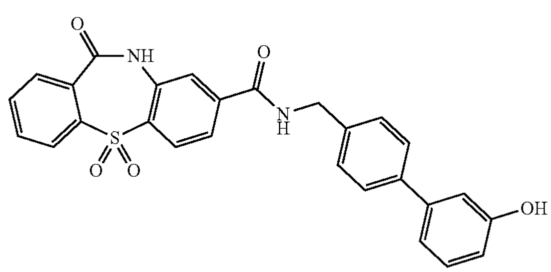 | A, 9, 99 | 20 | 485.1 (M+ + 1); | 484.11 for C27H20N2O5S | 1H-NMR (DMSO-d6, 400 MHz): δ 11.51 (s, 1H), 9.48 (s, 1H), 9.30 (t, J = 5.8 Hz, 1H), 8.06 (d, J = 8.2 Hz, 1H), 8.01-7.95 (m, 2H), 7.94-7.81 (m, 4H), 7.54 (d, J = 8.2 Hz, 2H), 7.36 (d, J = 8.2 Hz, 2H), 7.23 (t, J = 7.9 Hz, 1H), 7.03 (d, J = 8.2 Hz, 1H), 6.80-6.98 (m, 1H), 6.76-6.72 (m, 1H), 4.50 (d, J = 5.9 Hz, 2H); |
| 638 | 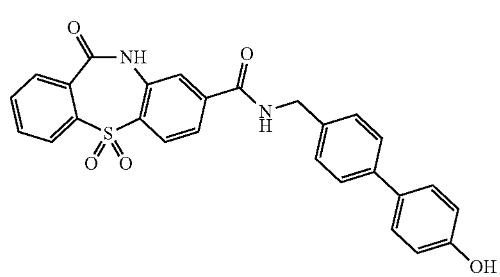 [SMILES: O=C(NCc1ccc(-c2ccc(O)cc2)cc1)c1ccc2c(c1)NC(=O)c1ccccc1S2(=O)=O] | A, 9, 102 | 29 | 484.9 (M+ + 1); | 484.11 for C27H20N2O5S | 1H NMR (DMSO-d6, 400 MHz): δ 11.52 (br s, 1H), 9.51 (s, 1H), 9.29 (t, J = 5.8 Hz, 1H), 8.06 (d, J = 8.2 Hz, 1H), 7.98 (td, J = 7.7, 1.0 Hz, 2H), 7.93-7.82 (m, 4H), 7.52 (d, J = 8.2 Hz, 2H), 7.45 (d, J = 8.6 Hz, 2H), 7.33 (d, J = 8.2 Hz, 2H), 6.83 (d, J = 8.6 Hz, |

TABLE 1-continued

| Compound No. | Structure | Procedure, Intermediate amine | Rx. Yield (%) | Mass Spec. Found | Mass Spec. Calculated | ¹H-NMR |
|---|---|---|---|---|---|---|
| | | | | | | 2H), 4.48 (d, J = 5.6 Hz, 2H); |
| 646 | 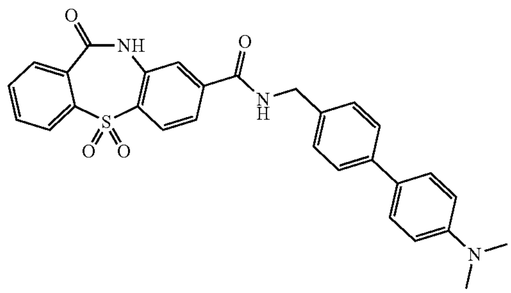 [SMILES: CN(C)c1ccc(-c2ccc(CNC(=O)c3ccc4c(c3)NC(=O)c3ccccc3S4(=O)=O)cc2)cc1] | A[b], 9, 91 | 30 | 512.0 (M⁺ + 1); | 511.16 for $C_{29}H_{25}N_3O_4S$ | ¹H-NMR (DMSO-$d_6$, 400 MHz): δ 11.52 (s, 1H), 9.28 (t, J = 5.9 Hz, 1H), 8.06 (d, J = 8.2 Hz, 1H), 7.98 (dd, J = 7.9, 1.0 Hz, 2H), 7.93-7.83 (m, 4H), 7.52 (d, J = 8.3 Hz, 2H), 7.48 (d, J = 8.8 Hz, 2H), 7.31 (d, J = 8.1 Hz, 2H), 6.78 (d, J = 8.9 Hz, 2H), 4.47 (d, J = 5.7 Hz, 2H), 2.92 (s, 6H); |
| 568 | 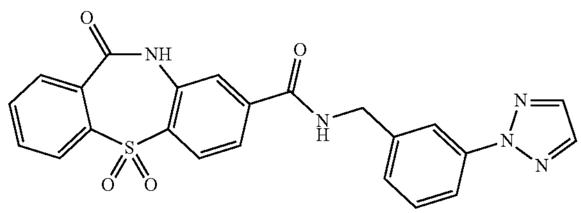 [SMILES: O=C(NCc1cccc(-n2nccn2)c1)c1ccc2c(c1)NC(=O)c1ccccc1S2(=O)=O] | A, 9, 58 | 20 | 460.2 (M⁺ + 1); | 459.10 for $C_{23}H_{17}N_5O_4S$ | ¹H NMR (DMSO-$d_6$, 400 MHz): δ 11.51 (s, 1H), 9.39 (t, J = 5.9 Hz, 1H), 8.09 (s, 2H), 8.07 (d, J = 8.2 Hz, 1H), 8.01-7.96 (m, 3H), 7.93-7.83 (m, 5H), 7.52 (t, J = 7.8 Hz, 1H), 7.36 (d, J = 7.4 Hz, 1H), 4.57 (d, J = 5.9 Hz, 2H); |
| 567 | 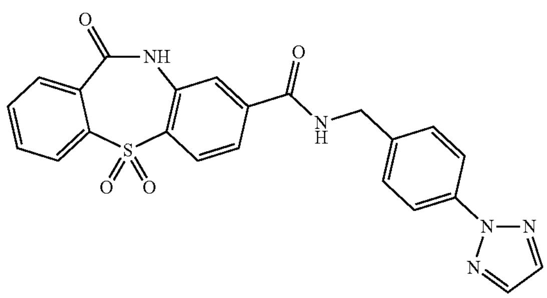 [SMILES: O=C(NCc1ccc(-n2nccn2)cc1)c1ccc2c(c1)NC(=O)c1ccccc1S2(=O)=O] | A, 9, 62 | 57 | 460.0 (M⁺ + 1); | 459.10 for $C_{23}H_{17}N_5O_4S$ | ¹H NMR (DMSO-$d_6$, 400 MHz): δ 11.51 (br s, 1H), 9.35 (t, J = 5.8 Hz, 1H), 8.09 (s, 2H), 8.07 (d, J = 8.0 Hz, 1H), 8.01-7.95 (m, 4H), 7.93-7.83 (m, 4H), 7.49 (d, J = 8.6 Hz, 2H), 4.53 (d, J = 5.7 Hz, 2H); |
| 570 | 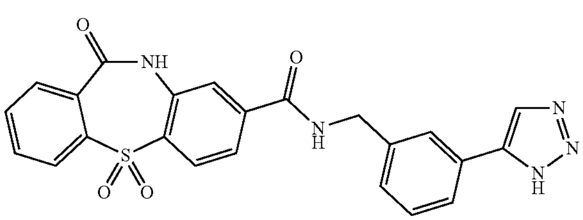 [SMILES: O=C(NCc1cccc(-c2cnn[nH]2)c1)c1ccc2c(c1)NC(=O)c1ccccc1S2(=O)=O] | A, 9, 78 | 11 | 460.0 (M⁺ + 1); | 459.10 for $C_{23}H_{17}N_5O_4S$ | ¹H NMR (DMSO-$d_6$, 500 MHz): δ 15.06 (br s, 1H), 11.51 (br s, 1H), 9.33 (t, J = 5.8 Hz, 1H), 8.29 (br s, 1H), 8.06 (d, J = 8.1 Hz, 1H), 8.01-7.95 (m, 2H), 7.93-7.83 (m, 4H), 7.81 (br s, 1H), 7.73 (d, J = 7.5 Hz, 1H), 7.40 (t, J = 7.7 Hz, 1H), 7.29 (d, J = 7.5 Hz, 1H), 4.53 (d, J = 5.5 Hz, 2H); |

TABLE 1-continued

| Compound No. | Structure | Procedure, Intermediate amine | Rx. Yield (%) | Mass Spec. Found | Mass Spec. Calculated | $^1$H-NMR |
|---|---|---|---|---|---|---|
| 569 | 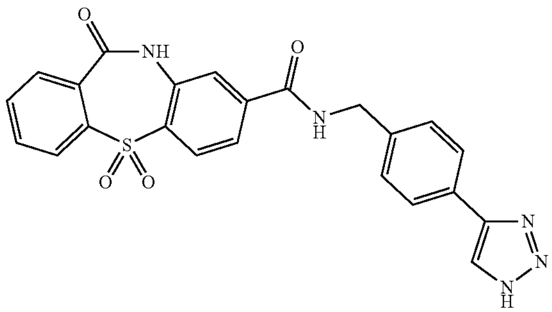 [SMILES: O=C(NCc1ccc(-c2c[nH]nn2)cc1)c1ccc2c(c1)NC(=O)c1ccccc1S2(=O)=O] | A, 9, 72 | 11 | 460.0 (M$^+$ + 1); | 459.10 for C$_{23}$H$_{17}$N$_5$O$_4$S | $^1$H NMR (DMSO-d$_6$, 500 MHz): δ 11.60 (br s, 1H), 9.30 (t, J = 5.8 Hz, 1H), 8.28 (br s, 1H), 8.05 (d, J = 8.1 Hz, 1H), 8.01-7.95 (m, 2H), 7.90 (dt, J = 7.1, 1.2 Hz, 1H), 7.87-7.83 (m, 3H), 7.80 (d, J = 8.1 Hz, 2H), 7.38 (d, J = 8.1 Hz, 2H), 4.49 (d, J = 5.8 Hz, 2H); |
| 569-A | 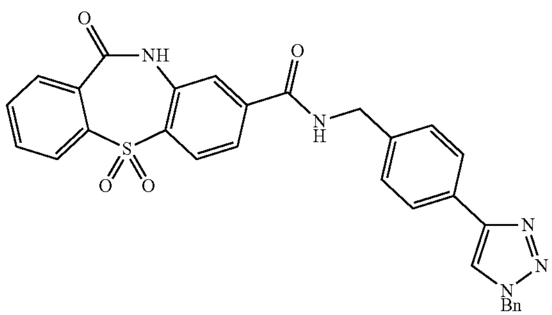 [SMILES: O=C(NCc1ccc(-c2cn(Cc3ccccc3)nn2)cc1)c1ccc2c(c1)NC(=O)c1ccccc1S2(=O)=O] | A, 9, 70 | 21 | 549.9 (M$^+$ + 1); | 549.15 for C$_{30}$H$_{23}$N$_5$O$_4$S | $^1$H NMR (DMSO-d$_6$, 500 MHz): δ 11.51 (s, 1H), 9.29 (t, J = 5.9 Hz, 1H), 8.59 (s, 1H), 8.06 (d, J = 8.1 Hz, 1H), 8.01-7.96 (m, 2H), 7.90 (dt, J = 7.5, 1.2 Hz, 1H), 7.88-7.84 (m, 3H), 7.79 (d, J = 8.1 Hz, 2H), 7.41-7.32 (m, 7H), 5.63 (s, 2H), 4.49 (d, J = 5.8 Hz, 2H); |
| 643 | 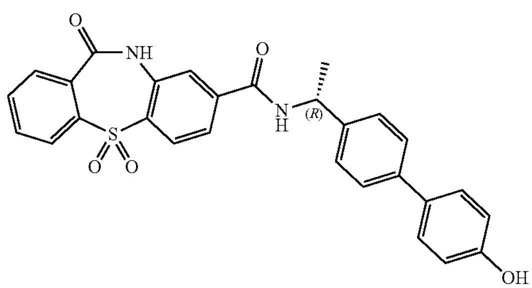 | A, 9, 114 | 11 | 497.2 (M − 1)$^+$; | 498.12 for C$_{28}$H$_{22}$N$_2$O$_5$S | $^1$H-NMR (DMSO-d$_6$, 400 MHz): δ 11.48 (br s, 1H), 9.49 (s, 1H), 9.05 (d, J = 7.3 Hz, 1H), 8.04 (d, J = 8.4 Hz, 1H), 8.00-7.94 (m, 2H), 7.93-7.80 (m, 4H), 7.50 (d, J = 8.2 Hz, 2H), 7.44 (d, J = 8.6 Hz, 2H), 7.38 (d, J = 7.9 Hz, 2H), 6.82 (d, J = 8.6 Hz, 2H), 5.15 (t, J = 7.7 Hz, 1H), 1.47 (d, J = 6.9 Hz, 3H); |
| 640 | 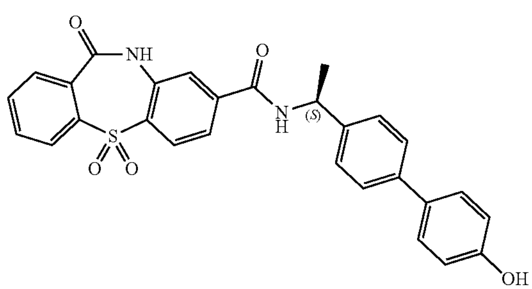 | A, 9, 116 | 18 | 499.2 (M$^+$ + 1); | 498.12 for C$_{28}$H$_{22}$N$_2$O$_5$S | $^1$H-NMR (DMSO-d$_6$, 400 MHz): δ 11.48 (s, 1H), 9.49 (s, 1H), 9.06 (d, J = 7.7 Hz, 1H), 8.05 (d, J = 8.3 Hz, 1H), 8.01-7.95 (m, 2H), 7.93-7.82 (m, 4H), 7.50 (d, J = 8.3 Hz, 2H), 7.44 (d, J = 8.6 Hz, 2H), 7.38 (d, J = 8.2 Hz, 2H), 6.82 (d, J = 8.7 Hz, 2H), 5.15 (t, J = 7.5 Hz, 1H), 1.47 (d, J = 7.0 Hz, 3H); |

TABLE 1-continued

| Compound No. | Structure | Procedure, Intermediate amine | Rx. Yield (%) | Mass Spec. Found | Mass Spec. Calculated | $^1$H-NMR |
|---|---|---|---|---|---|---|
| 662 | 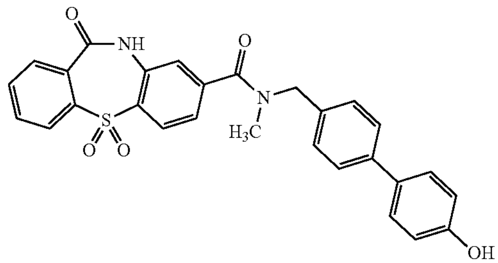 [SMILES: CN(Cc1ccc(-c2ccc(O)cc2)cc1)C(=O)c1ccc2c(c1)NC(=O)c1ccccc1S2(=O)=O] | A, 9, 105 | 36 | 499.1 (M$^+$ + 1); | 498.12 for C$_{28}$H$_{22}$N$_2$O$_5$S | $^1$H-NMR (DMSO-d$_6$, 500 MHz): (rotamers): δ 11.46 (br s, 1H), 9.53 (br s, 1H), 8.06-7.81 (m, 5H), 7.63-7.31 (m, 7H), 7.15 (d, J = 6.4 Hz, 1H), 6.84 (d, J = 7.2 Hz, 2H), 4.71-4.65 (m, 1.5H), 4.42 (s, 0.5H), 2.91, 2.79 (s, 3H); |
| 530 | 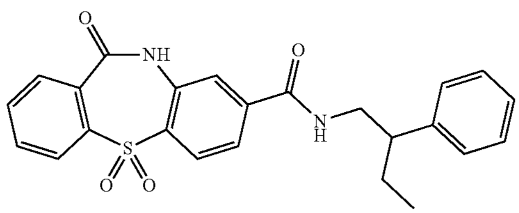 [SMILES: CCC(CNC(=O)c1ccc2c(c1)NC(=O)c1ccccc1S2(=O)=O)c1ccccc1] | A, 9, 47 | 42 | 435.1 (M$^+$ + 1); | 434.13 for C$_{24}$H$_{22}$N$_2$O$_4$S | $^1$H-NMR (DMSO-d$_6$, 400 MHz): 11.48 (s, 1H), 8.66 (t, J = 5.6 Hz, 1H), 8.03-7.94 (m, 3H), 7.93-7.82 (m, 2H), 7.74 (s, 1H), 7.67 (dd, J = 8.3, 1.5 Hz, 1H), 7.32-7.25 (m, 2H), 7.22-7.14 (m, 3H), 3.53-3.40 (m, 2H), 2.85-2.75 (m, 1H), 1.80-1.67 (m, 1H), 1.61-1.46 (m, 1H), 0.71 (t, J = 7.4 Hz, 3H); |
| 471 | 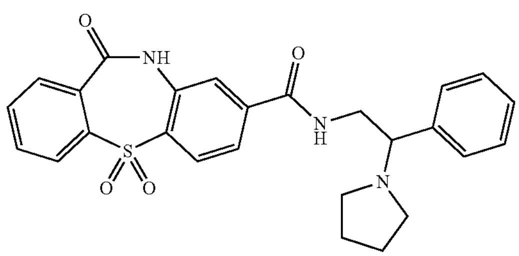 [SMILES: O=C(NCC(c1ccccc1)N1CCCC1)c1ccc2c(c1)NC(=O)c1ccccc1S2(=O)=O] | A, 9, 51 | 18 | 476.0 (M$^+$ + 1); | 475.16 for C$_{26}$H$_{25}$N$_3$O$_4$S | $^1$H-NMR (CD$_3$OD + CDCl$_3$ 400 MHz): δ 8.04-7.96 (m, 3H), 7.86-7.75 (m, 2H), 7.58 (s, 1H), 7.47 (dd, J = 8.2, 1.6 Hz, 1H), 7.37-7.23 (m, 5H), 4.00 (dd, J = 11.4, 2.9 Hz, 1H), 3.61-3.51 (m, 2H), 2.71-2.63 (m, 2H), 2.55-2.46 (m, 2H), 1.81-1.76 (m, 4H); |
| 472 | 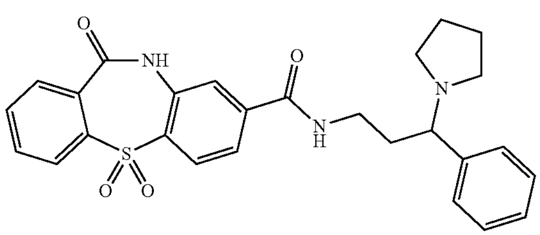 [SMILES: O=C(NCCC(c1ccccc1)N1CCCC1)c1ccc2c(c1)NC(=O)c1ccccc1S2(=O)=O] | A, 9, 54 | 44 | 490.0 (M$^+$ + 1); | 489.17 for C$_{27}$H$_{27}$N$_3$O$_4$S | $^1$H-NMR (CD$_3$OD + CDCl$_3$ 400 MHz): δ 8.06 (d, J = 8.3 Hz, 1H), 8.04-7.97 (m, 2H), 7.86-7.80 (m, 1.5 H), 7.79-7.76 (m, 1.5H), 7.64 (dd, J = 8.3, 1.6 Hz, 1H), 7.50-7.37 (m, 5H), 4.14-4.02 (m, 1H), 3.27-3.22 (m, 2H), 3.15-3.07 (m, 2H), 3.03-2.92 (m, 2H), 2.56-2.45 (m, 1H), 2.41-2.30 (m, |

TABLE 1-continued

| Compound No. | Structure | Procedure, Intermediate amine | Rx. Yield (%) | Mass Spec. Found | Mass Spec. Calculated | ¹H-NMR |
|---|---|---|---|---|---|---|
| | | | | | | 1H), 2.03-1.92 (m, 4H); |
| 533 | 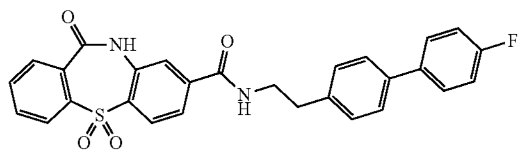 [SMILES: O=C(NCCc1ccc(-c2ccc(F)cc2)cc1)c1ccc2c(c1)NC(=O)c1ccccc1S2(=O)=O] | A, 9, 94 | 55 | 501.9 (M⁺ + 1); | 500.12 for $C_{28}H_{21}FN_2O_4S$ | ¹H-NMR (DMSO-$d_6$, 400 MHz): δ 11.51 (br s, 1H), 8.82 (t, J = 5.4 Hz, 1H), 8.04 (d, J = 8.2 Hz, 1H), 8.01-7.95 (m, 2H), 7.93-7.83 (m, 2H), 7.81 (s, 1H), 7.76 (dd, J = 8.5, 0.9 Hz, 1H), 7.67 (dd, J = 5.5, 8.7 Hz, 2H), 7.56 (d, J = 8.0 Hz, 2H), 7.31 (d, J = 8.0 Hz, 2H), 7.26 (t, J = 8.8 Hz, 2H), 3.51 (q, J = 6.5 Hz, 2H), 2.87 (t, J = 7.2 Hz, 2H); |
| 481 | 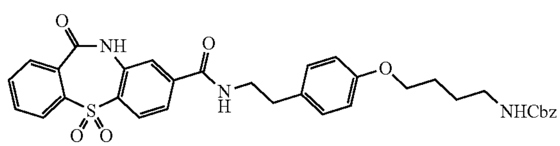 [SMILES: O=C(NCCCCOc1ccc(CCNC(=O)c2ccc3c(c2)NC(=O)c2ccccc2S3(=O)=O)cc1)OCc1ccccc1] | A, 9, 44 | 51 | 628.1 (M⁺ + 1); | $C_{34}H_{33}N_3O_7S$ 627.20 | ¹H NMR (DMSO-$d_6$, 400 MHz): δ 11.52 (s, 1H), 8.76 (t, J = 5.5 Hz, 1H), 8.03 (d, J = 8.3 Hz, 1H), 8.00-7.96 (m, 2H), 7.92-7.83 (m, 2H), 7.79 (s, 1H), 7.75 (dd, J = 8.2, 1.4 Hz, 1H), 7.44-7.22 (m, 6H), 7.11 (d, J = 8.6 Hz, 2H), 6.82 (d, J = 8.5 Hz, 2H), 5.00 (s, 2H), 3.90 (t, J = 6.2 Hz, 2H), 3.43 (q, J = 6.7 Hz, 2H), 3.04 (q, J = 6.7 Hz, 2H), 2.74 (t, J = 7.3 Hz, 2H), 1.71-1.63 (m, 2H), 1.58-1.49 (m, 2H); |
| 469 | 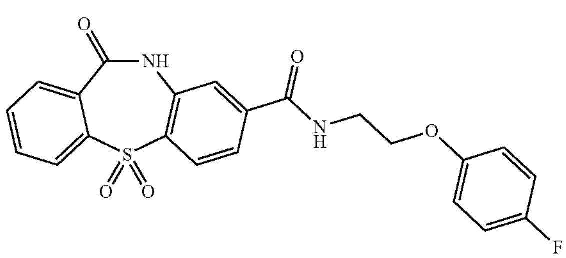 [SMILES: O=C(NCCOc1ccc(F)cc1)c1ccc2c(c1)NC(=O)c1ccccc1S2(=O)=O] | A, 159, 265 | 29 | 440.9 (M⁺ + 1); | $C_{22}H_{17}FN_2O_5S$ 440.08 | ¹H NMR (DMSO-$d_6$, 400 MHz): δ 11.51 (s, 1H), 8.92 (s, 1H), 8.04 (d, J = 8.2 Hz, 1H), 7.98 (td, J = 7.5, 0.9 Hz, 2H), 7.93-7.77 (m, 4H), 7.10 (t, J = 9.3 Hz, 2H), 7.00-6.91 (m, 2H), 4.08 (t, J = 5.5 Hz, 2H), 3.61 (q, J = 5.6 Hz, 2H); |

TABLE 1-continued

| Compound No. | Structure | Procedure, Intermediate amine | Rx. Yield (%) | Mass Spec. Found | Mass Spec. Calculated | ¹H-NMR |
|---|---|---|---|---|---|---|
| 657 | 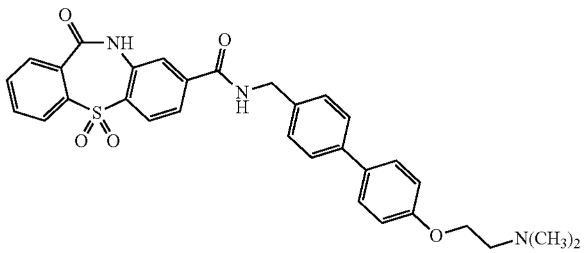 [SMILES: CN(C)CCOc1ccc(-c2ccc(CNC(=O)c3ccc4c(c3)NC(=O)c3ccccc3S4(=O)=O)cc2)cc1] | A, 9, 120 | 38 | 556.1 (M⁺ + 1); | 555.18 for $C_{31}H_{29}N_3O_5S$ | ¹H-NMR (DMSO-$d_6$, 400 MHz): δ = 11.52 (br. s., 1H), 9.32 (t, J = 5.7 Hz, 1H), 8.06 (d, J = 8.2 Hz, 1H), 7.98 (dd, J = 1.0, 7.6 Hz, 2H), 7.93 - 7.83 (m, 4H), 7.57 (t, J = 8.9 Hz, 4H), 7.36 (d, J = 8.2 Hz, 2H), 7.05 (d, J = 8.8 Hz, 2H), 4.49 (d, J = 5.9 Hz, 2H), 4.23 (t, J = 5.3 Hz, 2H), 3.10 (br. s., 2H), 2.56 (br. s., 5H) |
| 808-A | 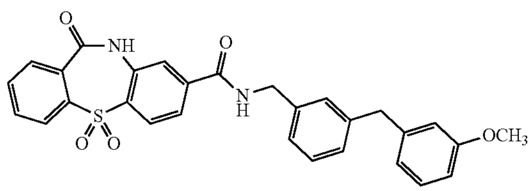 [SMILES: COc1cccc(Cc2cccc(CNC(=O)c3ccc4c(c3)NC(=O)c3ccccc3S4(=O)=O)c2)c1] | A$^c$, 9, 129 | 60 | 513.1 (M⁺ + 1); | 512.14 for $C_{29}H_{24}N_2O_5S$ | ¹H NMR (DMSO-$d_6$, 400 MHz): δ 11.48 (br s, 1H), 9.24 (t, J = 5.9 Hz, 1H), 8.04 (d, J = 8.3 Hz, 1H), 8.01-7.96 (m, 2H), 7.93-7.78 (m, 4H), 7.25-7.20 (m, 1H), 7.18-7.08 (m, 4H), 6.79-6.74 (m, 2H), 6.72-6.69 (m, 1H), 4.43 (br d, J = 5.8 Hz, 2H), 3.87 (s, 2H), 3.65 (s, 3H); |
| 809-A | 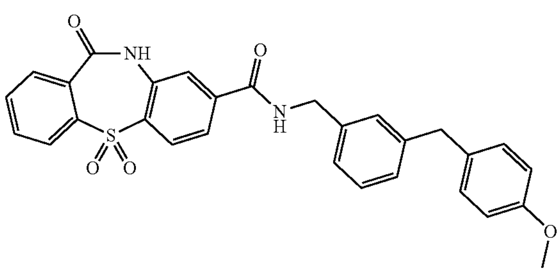 [SMILES: COc1ccc(Cc2cccc(CNC(=O)c3ccc4c(c3)NC(=O)c3ccccc3S4(=O)=O)c2)cc1] | A$^d$, 9, 132 | 53 | 513.0 (M⁺ + 1); | 512.14 for $C_{29}H_{24}N_2O_5S$ | ¹H-NMR (DMSO-$d_6$, 400 MHz): δ 11.51 (s, 1H), 9.23 (t, J = 6.0 Hz, 1H), 8.05 (d, J = 8.3 Hz, 1H), 8.01-7.96 (m, 2H), 7.93-7.78 (m, 4H), 7.24-7.19 (m, 1H), 7.14-7.05 (m, 5H), 6.81 (d, J = 8.8 Hz, 2H), 4.42 (d, J = 5.9 Hz, 2H), 3.83 (s, 2H), 3.68 (s, 3H); |
| 810-A | 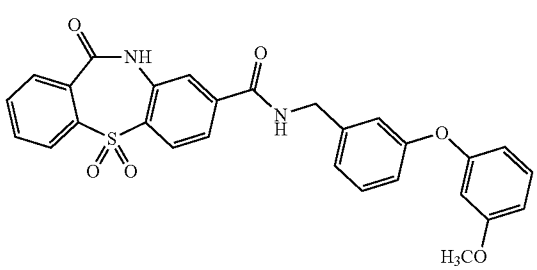 [SMILES: COc1cccc(Oc2cccc(CNC(=O)c3ccc4c(c3)NC(=O)c3ccccc3S4(=O)=O)c2)c1] | A$^c$, 9, 136 | 32 | 515.0 (M⁺ + 1); | 514.12 for $C_{28}H_{22}N_2O_6S$ | ¹H-NMR (DMSO-$d_6$, 400 MHz): δ 11.51 (s, 1H), 9.27 (t, J = 6.0 Hz, 1H), 8.05 (d, J = 8.2 Hz, 1H), 7.99 (td, J = 7.6, 1.1 Hz, 2H), 7.93-7.77 (m, 4H), 7.33 (t, J = 7.9 Hz, 1H), 7.24 (t, J = 8.2 Hz, 1H), 7.07 (d, J = 7.7 Hz, 1H), 6.95 (s, 1H), 6.88 (dd, J = 8.0, 1.9 Hz, 1H), 6.68-6.65 |

TABLE 1-continued

| Compound No. | Structure | Procedure, Intermediate amine | Rx. Yield (%) | Mass Spec. Found | Mass Spec. Calculated | 1H-NMR |
|---|---|---|---|---|---|---|
| | | | | | | (m, J = 8.3, 1.7 Hz, 1H), 6.56-6.48 (m, 2H), 4.45 (d, J = 5.8 Hz, 2H), 3.68 (s, 3H); |
| 811-A | 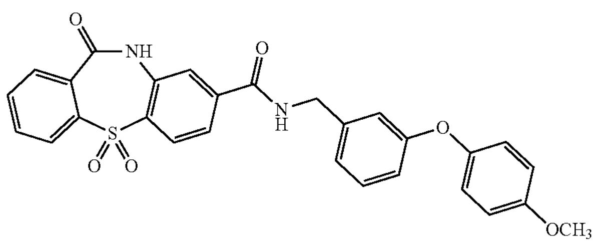 [SMILES: COc1ccc(Oc2cccc(CNC(=O)c3ccc4c(c3)NC(=O)c3ccccc3S4(=O)=O)c2)cc1] | $A^c$, 9, 139 | 47 | 515.0 (M$^+$ + 1); | 514.12 for $C_{28}H_{22}N_2O_6S$ | 1H-NMR (DMSO-d$_6$, 400 MHz): δ 11.51 (s, 1H), 9.25 (t, J = 5.8 Hz, 1H), 8.05 (d, J = 8.3 Hz, 1H), 8.01-7.95 (m, 2H), 7.93-7.82 (m, 3H), 7.78 (dd, J = 8.3, 1.3 Hz, 1H), 7.27 (t, J = 7.9 Hz, 1H), 7.02-6.91 (m, 5H), 6.86 (s, 1H), 6.77 (dd, J = 8.2, 1.9 Hz, 1H), 4.42 (d, J = 5.8 Hz, 2H), 3.72 (s, 3H); |
| 812-A | 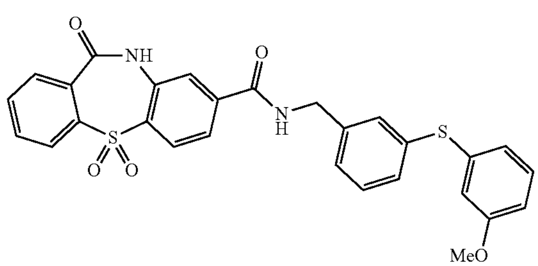 [SMILES: COc1cccc(Sc2cccc(CNC(=O)c3ccc4c(c3)NC(=O)c3ccccc3S4(=O)=O)c2)c1] | $A^b$, 9, 143 | 57 | 531.0 (M$^+$ + 1); | 530.10 for $C_{28}H_{22}N_2O_5S_2$ | 1H-NMR (DMSO-d$_6$, 500 MHz): δ 11.51 (br s, 1H), 9.26 (t, J = 5.9 Hz, 1H), 8.06-7.74 (m, 7H), 7.36-7.31 (m, 1H), 7.26-7.19 (m, 4H), 6.84-6.73 (m, 3H), 4.44 (br s, 2H), 3.63 (s, 3H); |
| 722 | 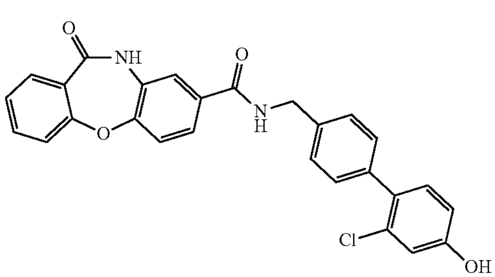 [SMILES: O=C(NCc1ccc(-c2ccc(O)cc2Cl)cc1)c1ccc2c(c1)NC(=O)c1ccccc1O2] | $A^e$, 14, 109 | 38 | 471.0 (M$^+$ + 1); | 470.10 for $C_{27}H_{19}ClN_2O_4$ | 1H-NMR (DMSO-d$_6$, 400 MHz): δ 10.63 (s, 1H), 9.95 (s, 1H), 9.06 (t, J = 6.1 Hz, 1H), 7.79 (dd, J = 7.7, 1.7 Hz, 1H), 7.73-7.61 (m, 3H), 7.43 (d, J = 8.3 Hz, 1H), 7.39-7.30 (m, 6H), 7.18 (d, J = 8.4 Hz, 1H), 6.91 (d, J = 2.5 Hz, 1H), 6.80 (dd, J = 8.4, 2.5 Hz, 1H), 4.49 (d, J = 6.0 Hz, 2H); |

TABLE 1-continued

| Compound No. | Structure | Procedure, Intermediate amine | Rx. Yield (%) | Mass Spec. Found | Mass Spec. Calculated | $^1$H-NMR |
|---|---|---|---|---|---|---|
| 721 | 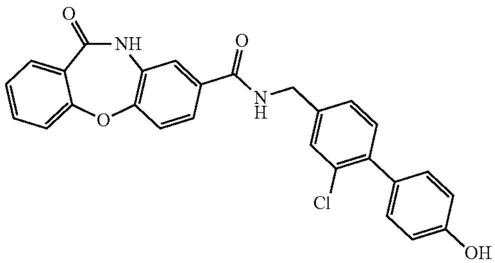 [SMILES: O=C(NCc1ccc(-c2ccc(O)cc2)c(Cl)c1)c1ccc2c(c1)NC(=O)c1ccccc1O2] | C, 14, 112 | 29 | 471.0 (M$^+$ + 1); | 470.10 for C$_{27}$H$_{19}$ClN$_2$O$_4$ | $^1$H-NMR (DMSO-d$_6$, 400 MHz): δ 10.64 (s, 1H), 9.57 (s, 1H), 9.09 (t, J = 5.9 Hz, 1H), 7.79 (dd, J = 7.7, 1.7 Hz, 1H), 7.72-7.61 (m, 3H), 7.45-7.42 (m, 2H), 7.39-7.27 (m, 4H), 7.22 (d, J = 8.6 Hz, 2H), 6.82 (d, J = 8.7 Hz, 2H), 4.46 (d, J = 5.7 Hz, 2H); |
| 717 | 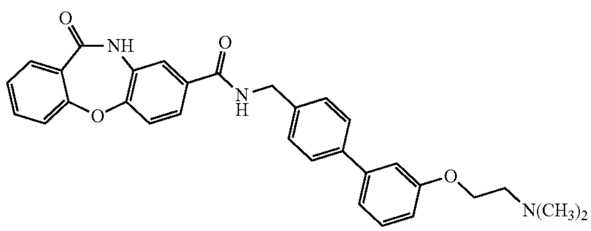 [SMILES: CN(C)CCOc1cccc(-c2ccc(CNC(=O)c3ccc4c(c3)NC(=O)c3ccccc3O4)cc2)c1] | A$^c$, 14, 122 | 3 | 508.1 (M$^+$ + 1); | 507.22 for C$_{31}$H$_{29}$N$_3$O$_4$ | $^1$H-NMR (DMSO-d$_6$, 400 MHz): δ 10.64 (s, 1H), 9.07 (br t, J = 5.8 Hz, 1H), 7.79 (br d, J = 6.7 Hz, 1H), 7.73-7.60 (m, 5H), 7.46-7.28 (m, 6H), 7.24-7.12 (m, 2H), 6.98-6.87 (m, 1H), 4.49 (br d, J = 5.6 Hz, 2H), 4.16 (br t, J = 5.5 Hz, 2H), 2.85-2.73 (m, 2H), 2.33 (br s, 6H); |
| 740 | 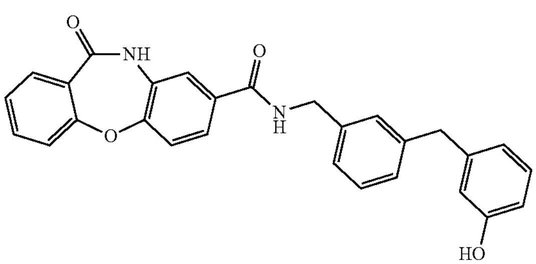 [SMILES: O=C(NCc1cccc(Cc2cccc(O)c2)c1)c1ccc2c(c1)NC(=O)c1ccccc1O2] | A, 14, 125 | 23 | 451.0 (M$^+$ + 1); | 450.16 for C$_{28}$H$_{22}$N$_2$O$_4$ | $^1$H-NMR (DMSO-d$_6$, 400 MHz): δ 10.62 (s, 1H), 9.23 (s, 1H), 8.99 (t, J = 6.0 Hz, 1H), 7.78 (dd, J = 7.8, 1.6 Hz, 1H), 7.68 (s, 1H), 7.66-7.59 (m, 2H), 7.43-7.31 (m, 3H), 7.23 (t, J = 7.8 Hz, 1H), 7.16-7.01 (m, 4H), 6.64-6.53 (m, 3H), 4.41 (d, J = 5.9 Hz, 2H), 3.81 (s, 2H); |
| 741-A | 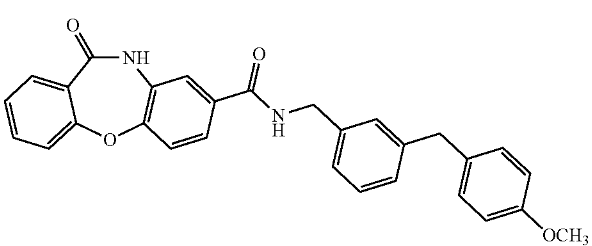 [SMILES: COc1ccc(Cc2cccc(CNC(=O)c3ccc4c(c3)NC(=O)c3ccccc3O4)c2)cc1] | A, 14, 132 | 38 | 465.0 (M$^+$ + 1); | 464.17 for C$_{29}$H$_{24}$N$_2$O$_4$ | $^1$H-NMR (DMSO-d$_6$, 400 MHz): δ 10.63 (s, 1H), 8.98 (t, J = 6.0 Hz, 1H), 7.78 (dd, J = 7.8, 1.6 Hz, 1H), 7.68 (s, 1H), 7.66-7.61 (m, 2H), 7.42 (d, J = 8.3 Hz, 1H), 7.38-7.31 (m, 2H), 7.21 (t, J = 7.8 Hz, 1H), 7.14-7.04 (m, 5H), 6.82 (d, J = 8.7 Hz, 2H), 4.40 (d, J = 6.0 Hz, 2H), 3.83 (s, 2H), 3.68 (s, 3H); |

TABLE 1-continued

| Compound No. | Structure | Procedure, Intermediate amine | Rx. Yield (%) | Mass Spec. Found | Mass Spec. Calculated | $^1$H-NMR |
|---|---|---|---|---|---|---|
| 744-A | 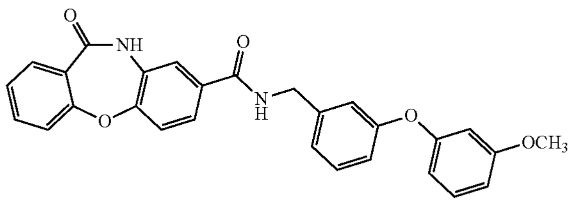 [SMILES: COc1cccc(Oc2cccc(CNC(=O)c3ccc4c(c3)NC(=O)c3ccccc3O4)c2)c1] | A$^b$, 14, 136 | 36 | 467.0 (M$^+$ + 1); | 466.15 for C$_{28}$H$_{22}$N$_2$O$_5$ | $^1$H-NMR (DMSO-d$_6$, 400 MHz): δ 10.63 (s, 1H), 9.03 (t, J = 6.0 Hz, 1H), 7.79 (dd, J = 7.7, 1.7 Hz, 1H), 7.70-7.59 (m, 3H), 7.42 (d, J = 8.4 Hz, 1H), 7.39-7.30 (m, 3H), 7.25 (t, J = 8.2 Hz, 1H), 7.07 (d, J = 7.8 Hz, 1H), 6.95 (s, 1H), 6.87 (dd, J = 8.0, 1.9 Hz, 1H), 6.70-6.66 (m, 1H), 6.58-6.47 (m, 2H), 4.43 (d, J = 5.9 Hz, 2H), 3.69 (s, 3H); |
| 745-A | 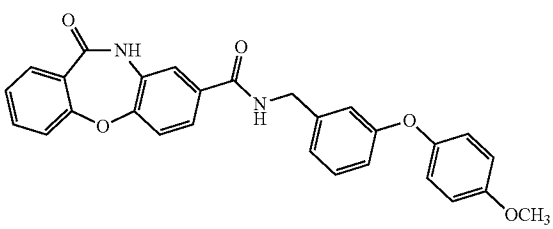 [SMILES: COc1ccc(Oc2cccc(CNC(=O)c3ccc4c(c3)NC(=O)c3ccccc3O4)c2)cc1] | A$^b$, 14, 139 | 33 | 467.0 (M$^+$ + 1); | 466.15 for C$_{28}$H$_{22}$N$_2$O$_5$ | $^1$H-NMR (DMSO-d$_6$, 400 MHz): δ 10.62 (s, 1H), 9.00 (t, J = 6.0 Hz, 1H), 7.79 (dd, J = 7.8, 1.6 Hz, 1H), 7.70-7.58 (m, 3H), 7.43-7.31 (m, 3H), 7.27 (t, J = 7.9 Hz, 1H), 7.02-6.91 (m, 4H), 6.86 (s, 1H), 6.76 (dd, J = 8.2, 1.8 Hz, 1H), 4.40 (d, J = 5.9 Hz, 2H), 3.71 (s, 3H); |
| 742-A | 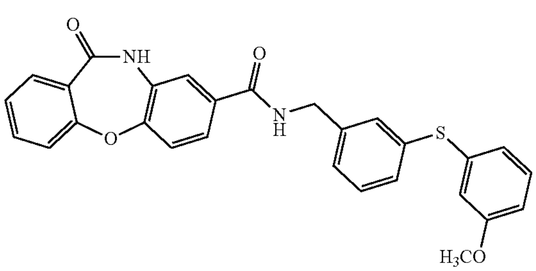 [SMILES: COc1cccc(Sc2cccc(CNC(=O)c3ccc4c(c3)NC(=O)c3ccccc3O4)c2)c1] | A, 14, 143 | 53 | 483.0 (M$^+$ + 1); | 482.13 for C$_{28}$H$_{22}$N$_2$O$_5$S | $^1$H NMR (DMSO-d$_6$, 400 MHz): δ 10.63 (s, 1H), 9.03 (br t, J = 5.9 Hz, 1H), 7.79 (dd, J = 7.8, 1.6 Hz, 1H), 7.68-7.56 (m, 3H), 7.44-7.31 (m, 4H), 7.29-7.18 (m, 4H), 6.86-6.75 (m, 3H), 4.42 (d, J = 5.9 Hz, 2H), 3.65 (s, 3H); |
| 743-A | 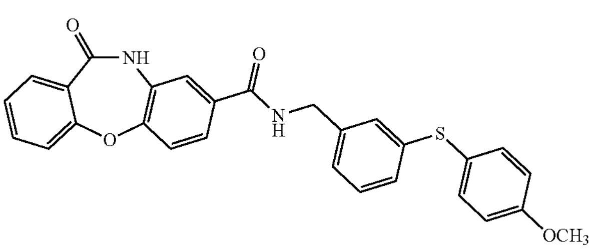 [SMILES: COc1ccc(Sc2cccc(CNC(=O)c3ccc4c(c3)NC(=O)c3ccccc3O4)c2)cc1] | A, 14, 146 | 38 | 483.2 (M$^+$ + 1); | 482.13 for C$_{28}$H$_{22}$N$_2$O$_4$S | $^1$H-NMR (DMSO-d$_6$, 400 MHz): δ 10.64 (s, 1H), 8.98 (t, J = 6.1 Hz, 1H), 7.79 (dd, J = 7.8, 1.6 Hz, 1H), 7.67-7.55 (m, 3H), 7.43-7.32 (m, 5H), 7.26-7.21 (m, 1H), 7.12-7.05 (m, 2H), 6.97 (d, J = 8.3 Hz, 1H), 6.94 (d, J = 8.8 Hz, 2H), 4.37 (d, J = 5.9 |

TABLE 1-continued

| Compound No. | Structure | Procedure, Intermediate amine | Rx. Yield (%) | Mass Spec. Found | Mass Spec. Calculated | ¹H-NMR |
|---|---|---|---|---|---|---|
| | | | | | | Hz, 2H), 3.70 (s, 3H); |
| 510 | 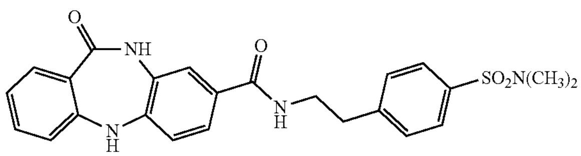 | A, 19, 33 | 22% | 465.0 (M⁺ + 1); | 464.15 for $C_{24}H_{24}N_4O_4S$ | ¹H-NMR (DMSO-$d_6$, 400 MHz): δ 9.90 (s, 1H), 8.36 (t, J = 5.4 Hz, 1H), 8.11 (s, 1H), 7.72-7.64 (m, 3H), 7.49 (d, J = 8.2 Hz, 2H), 7.43 (s, 1H), 7.39-7.31 (m, 2H), 6.99 (dd, J = 8.0, 3.4 Hz, 2H), 6.91 (t, J = 7.5 Hz, 1H), 3.49 (q, J = 6.7 Hz, 2H), 2.93 (t, J = 7.2 Hz, 2H), 2.56 (s, 6H); |
| 508 | 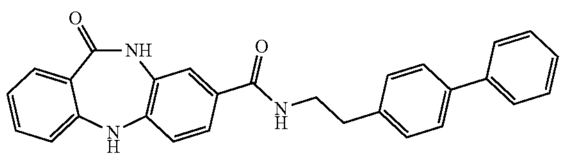 [SMILES: O=C(NCCc1ccc(-c2ccccc2)cc1)c1ccc2c(c1)NC(=O)c1ccccc1N2] | A, 19, 26 | 69% | 434.1 (M⁺ + 1); | 433.18 for $C_{28}H_{23}N_3O_2$ | ¹H-NMR (DMSO-$d_6$, 400 MHz): 9.91 (s, 1H), 8.38 (t, J = 5.4 Hz, 1H), 8.12 (s, 1H), 7.69 (dd, J = 7.8, 1.4 Hz, 1H), 7.61 (dd, J = 18.4, 7.8 Hz, 4H), 7.49-7.40 (m, 4H), 7.38-7.30 (m, 4H), 7.00 (t, J = 7.6 Hz, 2H), 6.91 (t, J = 7.5 Hz, 1H), 3.48 (q, J = 6.5 Hz, 2H), 2.86 (t, J = 7.2 Hz, 2H); |
| 498 | 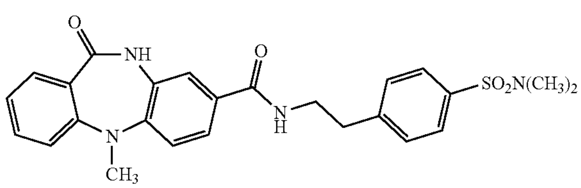 | A, 22, 33 | 28 | 479.0 (M⁺ + 1); | 478.17 for $C_{25}H_{26}N_4O_4S$ | ¹H-NMR (DMSO-$d_6$, 400 MHz): δ 10.29 (s, 1H), 8.45 (t, J = 5.5 Hz, 1H), 7.67-7.62 (m, 3H), 7.54-7.47 (m, 5H), 7.21 (t, J = 8.7 Hz, 2H), 7.10 (t, J = 7.5 Hz, 1H), 3.50 (q, J = 6.7 Hz, 2H), 3.29 (s, 3H), 2.93 (t, J = 7.0 Hz, 2H), 2.54 (s, 6H); |
| 501 | 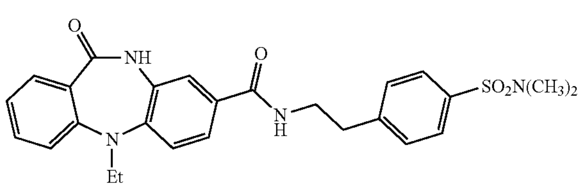 | A, 25, 33 | 40 | 493.1 (M⁺ + 1); | 492.18 for $C_{26}H_{28}N_4O_4S$ | ¹H-NMR (DMSO-$d_6$, 400 MHz): δ 10.31 (s, 1H), 8.48 (t, J = 5.5 Hz, 1H), 7.64 (d, J = 8.2 Hz, 2H), 7.60 (dd, J = 7.6, 1.5 Hz, 1H), 7.55-7.46 (m, 5H), 7.20 (t, J = 8.7 Hz, 2H), 7.10 (t, J = 7.4 Hz, 1H), 3.82-3.74 (m, 2H), 3.50 (q, J = 5.8 Hz, 2H), |

TABLE 1-continued

| Compound No. | Structure | Procedure, Intermediate amine | Rx. Yield (%) | Mass Spec. Found | Mass Spec. Calculated | 1H-NMR |
|---|---|---|---|---|---|---|
| | | | | | | 2.93 (t, J = 7.0 Hz, 2H), 2.54 (s, 6H), 1.12 (t, J = 7.0 Hz, 3H); |

A[a]: DIPEA (5 equiv);
A[b]: EDCI (2 equiv), HOBt (2 equiv);

Example 40: Synthesis of N-(4-bromobenzyl)-11-oxo-10,11-dihydrodibenzo[b,f][1,4]thiazepine-8-carboxamide 5,5-dioxide (147):—A common intermediate

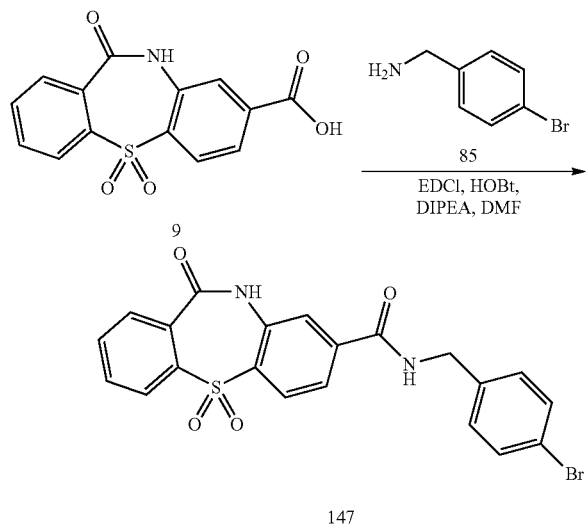

147

Example 41: Synthesis of N-(3-bromobenzyl)-11-oxo-10,11-dihydrodibenzo[b,f][1,4]thiazepine-8-carboxamide 5,5-dioxide (148): A common intermediate

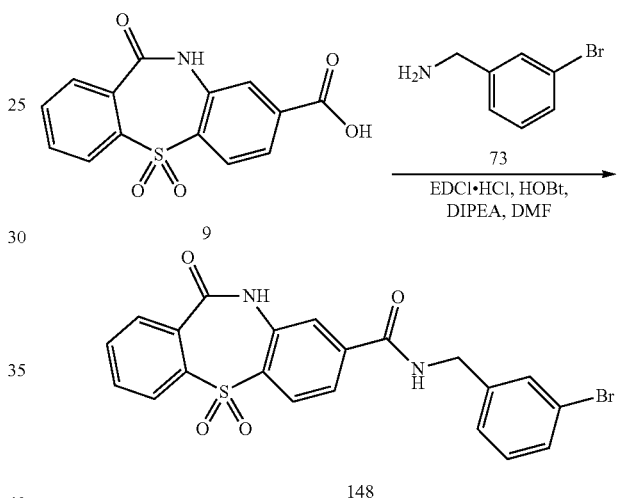

148

Synthesis of N-(4-bromobenzyl)-11-oxo-10,11-dihydrodibenzo[b,f][1,4]thiazepine-8-carboxamide 5,5-dioxide (147)

To a stirring solution of compound 9 (4 g, 13.20 mmol) in DMF (75 mL) under inert atmosphere were added EDCI·HCl (4.8 g, 13.97 mmol), HOBt (3.6 g, 26.66 mmol), (4-bromophenyl)methanamine 85 (2.6 g, 13.97 mmol) and diisopropylethylamine (7.3 mL, 39.60 mmol) at 0° C.; warmed to RT and stirred for 16 h. The reaction was monitored by TLC; after completion of the reaction, the reaction mixture was poured into ice-cold water (400 mL). The precipitated solid was filtered and dried in vacuo. The solid was further azeotrope using toluene (100 mL), washed 20% EtOAc/hexanes (150 mL) and dried in vacuo to afford compound 147 (5.8 g, 93%) as an off-white solid. TLC: 10% MeOH/CH$_2$Cl$_2$ (R$_f$: 0.4); $^1$H NMR (DMSO-d$_6$, 400 MHz): δ 11.52 (br s, 1H), 9.31 (t, J=5.9 Hz, 1H), 8.06 (d, J=8.2 Hz, 1H), 7.98 (dd, J=7.5, 1.1 Hz, 2H), 7.93-7.80 (m, 4H), 7.51 (d, J=8.4 Hz, 2H), 7.26 (d, J=8.5 Hz, 2H), 4.43 (d, J=5.9 Hz, 2H); LC-MS: 83.37%; 472.9 (M$^+$+2); (column; Ascentis Express C18, (50×3.0 mm, 2.7 μm); RT 2.43 min. 0.025% Aq. TFA+5% ACN: ACN+5% 0.025% Aq. TFA, 1.2 mL/min).

Synthesis of N-(3-bromobenzyl)-11-oxo-10,11-dihydrodibenzo[b, f][1,4]thiazepine-8-carboxamide 5,5-dioxide (148)

To a stirring solution of compound 9 (300 mg, 0.99 mmol) in DMF (8 mL) under inert atmosphere were added EDCI·HCl (283 mg, 1.48 mmol), HOBt (200 mg, 1.48 mmol), (3-bromophenyl) methanamine 73 (202 mg, 1.08 mmol) and diisopropylethylamine (0.36 mL, 1.98 mmol) at 0° C.; warmed to RT and stirred for 16 h. The reaction was monitored by TLC; after completion of the reaction, the reaction mixture was poured into ice-cold water (50 mL) and stirred for 15 min. The precipitated solid was filtered washed with water (50 mL), diethylether (20 mL), n-pentane (10 mL) dried in vacuo to afford compound 148 (350 mg, to 76%) as an off-white solid. TLC: 5% MeOH/CH$_2$Cl$_2$ (R$_f$: 0.5); $^1$H NMR (DMSO-d$_6$, 400 MHz): δ 11.33 (br s, 1H), 9.27 (t, J=5.9 Hz, 1H), 8.01 (d, J=8.3 Hz, 1H), 7.97-7.90 (m, 2H), 7.87 (td, J=7.5, 1.3 Hz, 1H), 7.83-7.78 (m, 2H), 7.74 (d, J=8.3 Hz, 1H), 7.52-7.48 (m, 1H), 7.44 (dt, J=6.8, 2.1 Hz, 1H), 7.33-7.28 (m, 2H), 4.45 (d, J=5.9 Hz, 2H); LC-MS: 83.97%; 470.8 (M$^+$+1); (column; Ascentis Express C18, (50×3.0 mm, 2.7 μm); RT 2.43 min. 0.025% Aq. TFA+5% ACN: ACN+5% 0.025% Aq. TFA, 1.2 mL/min).

Example 42: Synthesis of N-(4-bromobenzyl)-11-oxo-10,11-dihydrodibenzo[b,f][1,4]oxazepine-8-carboxamide (149): A common intermediate

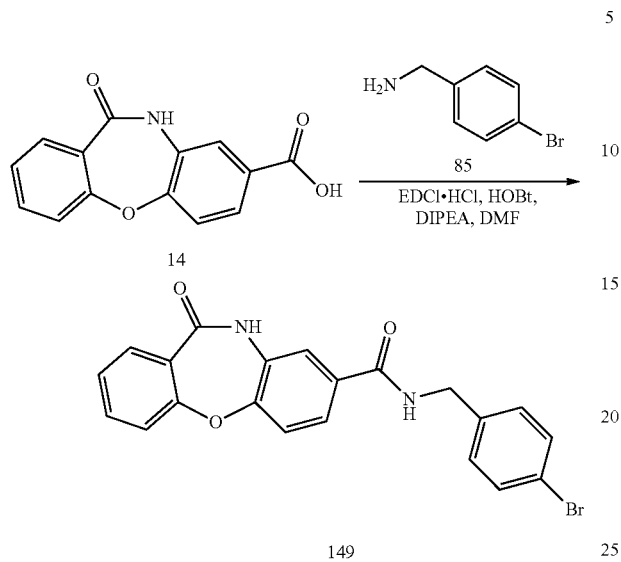

149

Synthesis of N-(4-bromobenzyl)-11-oxo-10,11-dihydrodibenzo[b,f][1,4]oxazepine-8-carboxamide (149)

To a stirring solution of compound 14 (2 g, 7.87 mmol) in DMF (15 mL) under inert atmosphere were added EDCI·HCl (2.85 g, 15.74 mmol), HOBt (2.12 g, 15.74 mmol), (4-bromophenyl) methanamine 85 (1.47 g, 7.87 mmol) and diisopropylethylamine (4.4 mL, 23.61 mmol) at 0° C.; warmed to RT and stirred for 16 h. The reaction was monitored by TLC; after completion of the reaction, the reaction mixture was poured into ice-cold water (400 mL). The precipitated solid was filtered and dried in vacuo to afford compound 149 (3.2 g, 88%) as an off-white solid. TLC: 10% MeOH/CH$_2$Cl$_2$ (R$_f$: 0.3); $^1$H NMR (DMSO-d$_6$, 400 MHz): δ 10.63 (s, 1H), 9.04 (t, J=5.8 Hz, 1H), 7.78 (dd, J=7.7, 1.3 Hz, 1H), 7.69 (s, 1H), 7.67-7.61 (m, 2H), 7.51 (d, J=8.4 Hz, 2H), 7.43 (d, J=8.4 Hz, 1H), 7.38-7.32 (m, 2H), 7.25 (d, J=8.4 Hz, 2H), 4.41 (d, J=5.8 Hz, 2H); LC-MS: 97.04%; 423.4 (M$^+$+1); (column; Ascentis Express C18, (50×3.0 mm, 2.7 μm); RT 2.48 min. 0.025% Aq. TFA+5% ACN: ACN+5% 0.025% Aq. TFA, 1.2 mL/min).

Example 43: Commercial Available Boronic Acids and Boronic Acid Derivatives

The following boronic acids were obtained from commercial sources.

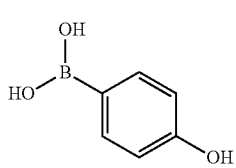

100

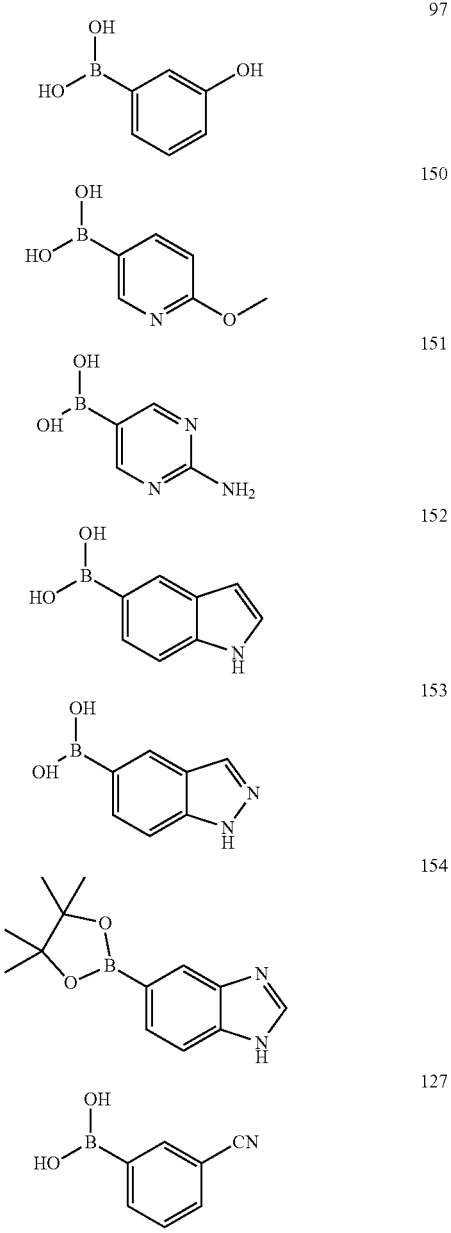

Example 44: Compound Preparation

The common intermediates 147, 148 and 149 were converted to final products using either commercially available coupling reagents or prepared coupling reagents employing typical procedure B & C and the results are captured in the Table 2:

Typical Procedure B:

To a stirring solution of N-(4-bromobenzyl)-11-oxo-10,11-dihydrodibenzo[b,f][1,4]thiazepine-8-carboxamide 5,5-dioxide 147 (150 mg, 0.31 mmol) in 1,2 dimethoxy ethane: H$_2$O (4: 1, 8 mL) were added sodium carbonate (124 mg, 1.17 mmol), (6-methoxypyridin-3-yl)boronic acid 150 (63 mg, 0.42 mmol) and purged under argon atmosphere for 20 min. To this was added Pd(dppf)Cl$_2$ (45 mg, 0.039 mmol) at RT; heated to 100-110° C. and stirred for 16 h. The reaction was monitored by TLC; after completion the volatiles were removed in vacuo to obtain the crude. The crude was either directly dried in vacuo or triturated or purified through silica gel column chromatography to afford the desired compound.

Typical Procedure C:

To a stirring solution of N-(4-bromobenzyl)-11-oxo-10,11-dihydrodibenzo[b,f][1,4]thiazepine-8-carboxamide 5,5-dioxide 147 (150 mg, 0.31 mmol) in 1,4 dioxane: H$_2$O (3:1, 10 mL) were added cesium carbonate (341 mg, 1.05 mmol), (1H-indazol-5-yl)boronic acid 153 (113 mg, 0.70 mmol) and purged under argon atmosphere for 15 min. To this was added Pd(dppf)Cl$_2$ (26 mg, 0.035 mmol) at RT; heated to 100° C. and stirred for 16 h. The reaction was monitored by TLC; after completion the volatiles were removed in vacuo to obtain the crude. The crude was either directly dried in vacuo or triturated or purified through silica gel column chromatography to afford the desired compound.

TABLE 2

Synthesis using cross coupling reaction:

| Compound No. | Structure | Procedure, Intermediate, coupling reagents | Rx. Yield % | Mass Spec. Found | Mass Spec. Calculated | $^1$H-NMR |
|---|---|---|---|---|---|---|
| 774 | 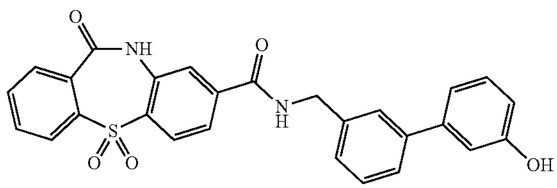 [SMILES: O=C(NCc1cccc(-c2cccc(O)c2)c1)c1ccc2c(c1)NC(=O)c1ccccc1S2(=O)=O] | B$^g$, 148, 97 | 39 | 485.0 (M$^+$ + 1) | 484.11 for C$_{27}$H$_{20}$N$_2$O$_5$S | $^1$H-NMR (DMSO-d$_6$, 400 MHz): δ 11.51 (s, 1H), 9.49 (s, 1H), 9.31 (t, J = 6.0 Hz, 1H), 8.05 (d, J = 8.2 Hz, 1H), 7.98 (td, J = 7.5, 1.0 Hz, 2H), 7.93-7.82 (m, 4H), 7.53 (s, 1H), 7.46 (dt, J = 7.8, 1.4 Hz, 1H), 7.39 (t, J = 7.6 Hz, 1H), 7.30-7.24 (m, 1H), 7.24-7.21 (m, 1H), 7.02 (d, J = 7.8 Hz, 1H), 6.98 (s, 1H), 6.77-6.73 (m, 1H), 4.53 (d, J = 5.8 Hz, 2H); |
| 773 | 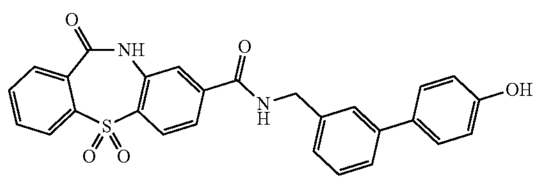 [SMILES: O=C(NCc1cccc(-c2ccc(O)cc2)c1)c1ccc2c(c1)NC(=O)c1ccccc1S2(=O)=O] | B$^b$, 148, 100 | 39 | 484.9 (M$^+$ + 1) | 484.11 for C$_{27}$H$_{20}$N$_2$O$_5$S | $^1$H-NMR (DMSO-d$_6$, 400 MHz): δ 7.98 (s, 1H), 9.52 (s, 1H), 9.29 (t, J = 5.8 Hz, 1H), 8.05 (d, J = 8.2 Hz, 1H), 7.98 (dd, J = 7.5, 1.1 Hz, 2H), 7.93-7.81 (m, 4H), 7.51 (s, 1H), 7.44 (d, J = 8.5 Hz, 3H), 7.35 (t, J = 7.7 Hz, 1H), 7.20 (d, J = 7.7 Hz, 1H), 6.83 (d, J = 8.7 Hz, 2H), 4.51 (d, J = 5.1 Hz, 2H); |
| 775 | 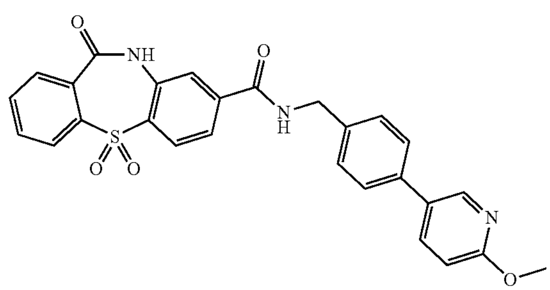 [SMILES: COc1ccc(-c2ccc(CNC(=O)c3ccc4c(c3)NC(=O)c3ccccc3S4(=O)=O)cc2)cn1] | B$^d$, 147, 150 | 19 | 500.0 (M$^+$ + 1) | 499.12 for C$_{27}$H$_{21}$N$_3$O$_5$S | $^1$H NMR (DMSO-d$_6$, 400 MHz): δ 11.50 (s, 1H), 9.30 (t, J = 5.6 Hz, 1H), 8.44 (d, J = 2.3 Hz, 1H), 8.04 (d, J = 8.2 Hz, 1H), 8.00-7.94 (m, 3H), 7.91-7.81 (m, 4H), 7.59 (d, J = 8.2 Hz, 2H), 7.37 (d, J = 8.2 Hz, 2H), 6.88 (d, J = 8.7 Hz, 1H), 4.48 (d, J = 5.8 Hz, 2H), 3.87 (s, 3H); |
| 777 | 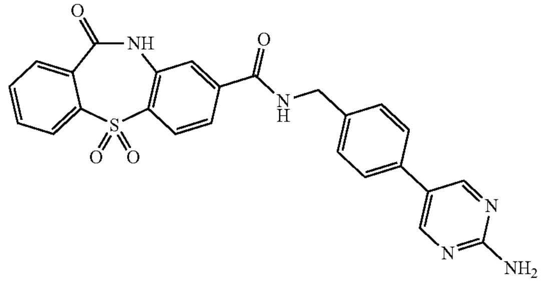 [SMILES: Nc1ncc(-c2ccc(CNC(=O)c3ccc4c(c3)NC(=O)c3ccccc3S4(=O)=O)cc2)cn1] | B$^a$, 147, 151 | 26 | 486.1 (M$^+$ + 1) | 485.12 for C$_{25}$H$_{19}$N$_5$O$_4$S | $^1$H-NMR (DMSO-d$_6$, 500 MHz): δ 11.51 (s, 1H), 9.29 (t, J = 5.8 Hz, 1H), 8.54 (s, 2H), 8.06 (d, J = 8.4 Hz, 1H), 7.98 (t, J = 8.1 Hz, 2H), 7.93-7.83 (m, 4H), 7.56 (d, J = 8.1 Hz, 2H), 7.35 (d, J = 8.1 Hz, 2H), 6.74 (s, 2H), 4.48 (d, J = 5.5 Hz, 2H); |

TABLE 2-continued

Synthesis using cross coupling reaction:

| Compound No. | Structure | Procedure, Intermediate, coupling reagents | Rx. Yield % | Mass Spec. Found | Mass Spec. Calculated | ¹H-NMR |
|---|---|---|---|---|---|---|
| 647 | 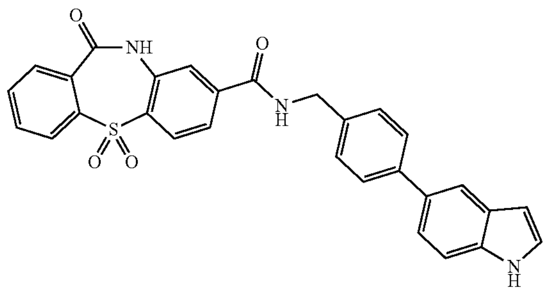 [SMILES: O=C(NCc1ccc(-c2ccc3[nH]ccc3c2)cc1)c1ccc2c(c1)NC(=O)c1ccccc1S2(=O)=O] | B$^c$, 147, 152 | 47 | 508.3 (M$^+$ + 1); | 507.13 for C$_{29}$H$_{21}$N$_3$O$_4$S | ¹H-NMR (DMSO-d$_6$, 400 MHz): δ 11.51 (br s, 1H), 11.11 (br s, 1H), 9.30 (t, J = 5.8 Hz, 1H), 8.06 (d, J = 8.4 Hz, 1H), 8.01-7.96 (m, 2H), 7.93-7.83 (m, 4H), 7.78 (s, 1H), 7.61 (d, J = 8.1 Hz, 2H), 7.45 (d, J = 8.4 Hz, 1H), 7.36 (d, J = 7.5 Hz, 4H), 6.47 (br s, 1H), 4.50 (d, J = 5.8 Hz, 2H); |
| 678 | 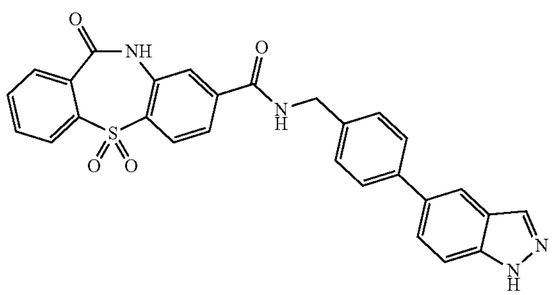 [SMILES: O=C(NCc1ccc(-c2ccc3[nH]ncc3c2)cc1)c1ccc2c(c1)NC(=O)c1ccccc1S2(=O)=O] | C, 147, 153 | 34 | 509.0 (M$^+$ + 1); | 508.12 for C$_{28}$H$_{20}$N$_4$O$_4$S | ¹H-NMR (DMSO-d$_6$, 500 MHz): δ 13.08 (br s, 1H), 11.49 (br s, 1H), 9.26 (t, J = 5.6 Hz, 1H), 8.09 (s, 1H), 8.01-7.89 (m, 4H), 7.88-7.73 (m, 4H), 7.65-7.56 (m, 4H), 7.37 (d, J = 8.1 Hz, 2H), 4.49 (d, J = 5.8 Hz, 2H); |
| 644 | 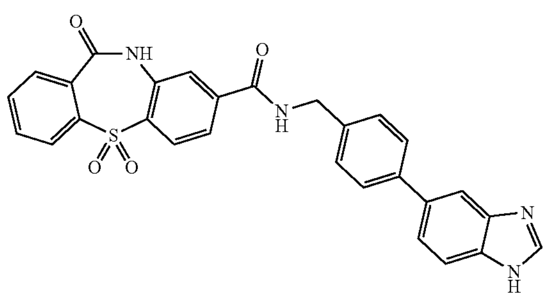 [SMILES: O=C(NCc1ccc(-c2ccc3[nH]cnc3c2)cc1)c1ccc2c(c1)NC(=O)c1ccccc1S2(=O)=O] | C$^a$, 147, 154 | 8 | 509.0 (M$^+$ + 1); | 508.12 C$_{28}$H$_{20}$N$_4$O$_4$S | ¹H-NMR (DMSO-d$_6$, 400 MHz): δ 12.50 (br s, 1H), 11.53 (br s, 1H), 9.33 (t, J = 5.6 Hz, 1H), 8.23 (s, 1H), 8.06 (d, J = 8.2 Hz, 1H), 7.98 (t, J = 8.0 Hz, 2H), 7.93-7.82 (m, 5H), 7.73-7.67 (m, 1H), 7.64 (d, J = 7.9 Hz, 1H), 7.60-7.56 (m, 1H), 7.52-7.43 (m, 1H), 7.38 (d, J = 7.7 Hz, 2H), 4.51 (d, J = 5.5 Hz, 2H); |
| 676-A | 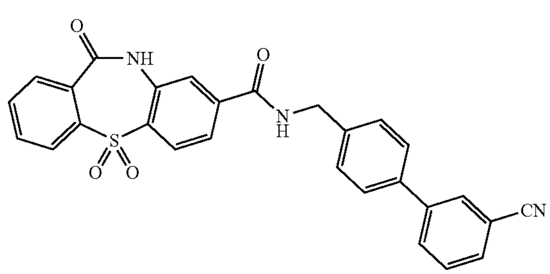 [SMILES: N#Cc1cccc(-c2ccc(CNC(=O)c3ccc4c(c3)NC(=O)c3ccccc3S4(=O)=O)cc2)c1] | B$^b$, 147, 127 | 64 | 494.1 (M$^+$ + 1); | 493.11 for C$_{28}$H$_{19}$N$_3$O$_4$S | ¹H-NMR (DMSO-d$_6$, 400 MHz): δ 11.52 (s, 1H), 9.33 (t, J = 5.8 Hz, 1H), 8.13 (t, J = 1.5 Hz, 1H), 8.07 (d, J = 8.2 Hz, 1H), 8.02-7.96 (m, 3H), 7.93-7.79 (m, 5H), 7.74-7.60 (m, 3H), 7.42 (d, J = 8.4 Hz, 2H), 4.52 (d, J = 5.9 Hz, 2H); |

TABLE 2-continued

Synthesis using cross coupling reaction:

| Compound No. | Structure | Procedure, Intermediate, coupling reagents | Rx. Yield % | Mass Spec. Found | Mass Spec. Calculated | ¹H-NMR |
|---|---|---|---|---|---|---|
| 720 | 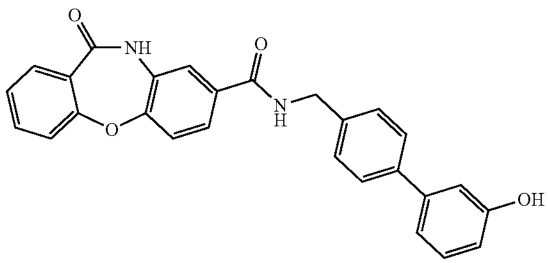 [SMILES: O=C(NCc1ccc(-c2cccc(O)c2)cc1)c1ccc2c(c1)NC(=O)c1ccccc1O2] | B[b], 149, 97 | 71 | 437.0 (M⁺ + 1); | 436.14 for $C_{27}H_{20}N_2O_4$ | ¹H-NMR (DMSO-d₆, 500 MHz): δ 10.63 (s, 1H), 9.48 (s, 1H), 9x.05 (t, J = 5.6 Hz, 1H), 7.79 (dd, J = 7.8, 1.2 Hz, 1H), 7.72-7.61 (m, 3H), 7.54 (d, J = 8.1 Hz, 2H), 7.43 (d, J = 8.1 Hz, 1H), 7.39-7.31 (m, 4H), 7.23 (t, J = 7.8 Hz, 1H), 7.03 (d, J = 7.8 Hz, 1H), 6.99 (s, 1H), 6.74 (dd, J = 8.0, 1.6 Hz, 1H), 4.48 (d, J = 5.8 Hz, 2H); |
| 719 | 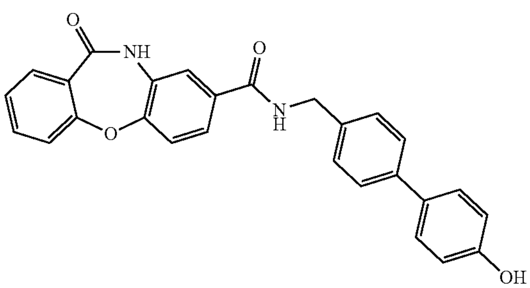 | B[b], 149, 100 | 19 | 437.0 (M⁺ + 1); | 436.14 for $C_{27}H_{20}N_2O_4$ | ¹H-NMR (DMSO-d₆, 500 MHz): δ 10.63 (s, 1H), 9.49 (s, 1H), 9.03 (t, J = 5.9 Hz, 1H), 7.78 (dd, J = 7.8, 1.7 Hz, 1H), 7.71 (s, 1H), 7.68-7.61 (m, 2H), 7.51 (d, J = 8.1 Hz, 2H), 7.47-7.41 (m, 3H), 7.39-7.31 (m, 4H), 6.82 (d, J = 8.7 Hz, 2H), 4.46 (d, J = 5.8 Hz, 2H); |
| 728-A | 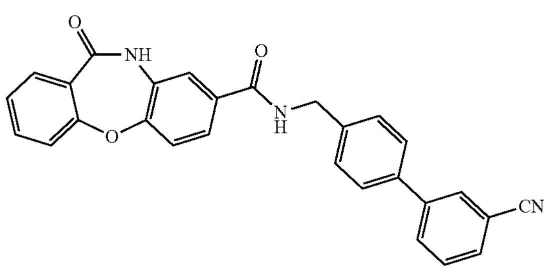 [SMILES: N#Cc1cccc(-c2ccc(CNC(=O)c3ccc4c(c3)NC(=O)c3ccccc3O4)cc2)c1] | B[c], 149, 127 | 67 | 446.0 (M⁺ + 1); | 445.14 for $C_{28}H_{19}N_3O_3$ | ¹H NMR (DMSO-d₆, 400 MHz): δ 10.64 (s, 1H), 9.09 (t, J = 6.0 Hz, 1H), 8.13 (t, J = 1.4 Hz, 1H), 8.00 (dt, J = 8.0, 1.4 Hz, 1H), 7.83-7.77 (m, 2H), 7.73-7.61 (m, 6H), 7.46-7.31 (m, 5H), 4.50 (d, J = 5.9 Hz, 2H); |
| 726-A | 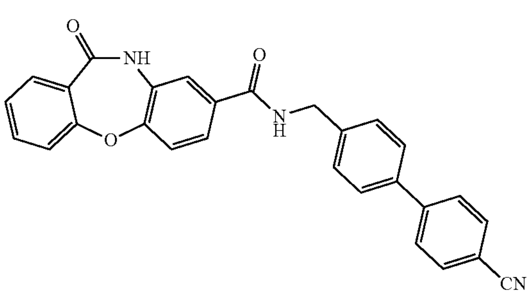 [SMILES: N#Cc1ccc(-c2ccc(CNC(=O)c3ccc4c(c3)NC(=O)c3ccccc3O4)cc2)cc1] | C[a], 149, 107 | 55 | 446.0 (M⁺ + 1); | 445.14 for $C_{28}H_{19}N_3O_3$ | ¹H NMR (DMSO-d₆, 400 MHz, DMSO-d₆) δ 10.63 (s, 1H), 9.09 (br t, J = 5.9 Hz, 1H), 7.94-7.82 (m, 4H), 7.79 (dd, J = 7.7, 1.6 Hz, 1H), 7.74-7.60 (m, 5H), 7.43 (dd, J = 8.2, 2.1 Hz, 3H), 7.39-7.31 (m, 2H), 4.51 (br d, J = 5.8 Hz, 2H); |

TABLE 2-continued

Synthesis using cross coupling reaction:

| Compound No. | Structure | Procedure, Intermediate, coupling reagents | Rx. Yield % | Mass Spec. Found | Mass Spec. Calculated | $^1$H-NMR |
|---|---|---|---|---|---|---|
| 730 | 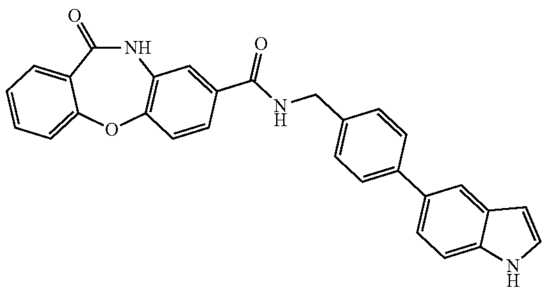 [SMILES: O=C(NCc1ccc(-c2ccc3[nH]ccc3c2)cc1)c1ccc2c(c1)NC(=O)c1ccccc1O2] | B$^b$, 149, 152 | 52 | 460.1 (M$^+$ + 1); | 459.16 for $C_{29}H_{21}N_3O_3$ | $^1$H-NMR (DMSO-d$_6$, 500 MHz): δ 11.11 (br s, 1H), 10.64 (s, 1H), 9.05 (t, J = 5.8 Hz, 1H), 7.81-7.77 (m, 2H), 7.74-7.58 (m, 5H), 7.44 (t, J = 8.4 Hz, 2H), 7.40-7.31 (m, 6H), 6.47 (br s, 1H), 4.49 (d, J = 5.8 Hz, 2H); |
| 729 | 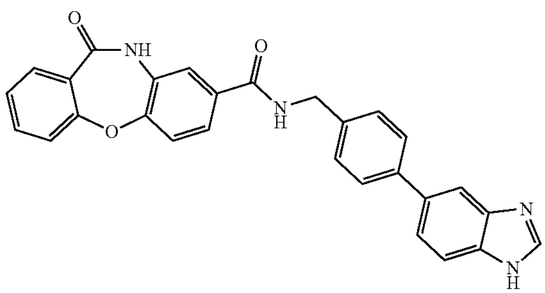 [SMILES: O=C(NCc1ccc(-c2ccc3[nH]cnc3c2)cc1)c1ccc2c(c1)NC(=O)c1ccccc1O2] | B$^e$, 149, 154 | 15 | 461.0 (M$^+$ + 1); | 460.15 for $C_{28}H_{20}N_4O_3$ | $^1$H NMR (DMSO-d$_6$, 400 MHz): δ 14.22 (br s, 1H), 10.64 (s, 1H), 9.09 (t, J = 5.8 Hz, 1H), 9.00 (br s, 1H), 7.92 (s, 1H), 7.84-7.76 (m, 2H), 7.74-7.60 (m, 6H), 7.48-7.30 (m, 5H), 4.51 (d, J = 5.8 Hz, 2H); |

B$^a$: Pd(PPh$_3$)$_4$ (0.1 equiv), reaction temp 90-100° C.;
B$^b$: Pd(PPh$_3$)$_4$ (0.1 equiv), Na$_2$CO$_3$ (3.0 equiv);
B$^c$: Pd(PPh$_3$)$_4$ (0.1 equiv), reaction performed in a sealed tube;
B$^d$: Na$_2$CO$_3$ (4 equiv);
B$^e$: Pd(PPh$_3$)$_4$ (0.1 equiv), boronic acid (1 equiv), Na$_2$CO$_3$ (2 equiv), 12 h sealed tube;
B$^f$: Reaction performed in a sealed tube;
B$^g$: DME: H$_2$O (3: 1), Na$_2$CO$_3$ (3 equiv), boronic acid/Ester (1.2 equiv), reaction performed in sealed tube, reaction temp 120° C., 16 h;
C$^a$: reaction time 12 h Example 45: Synthesis of 482

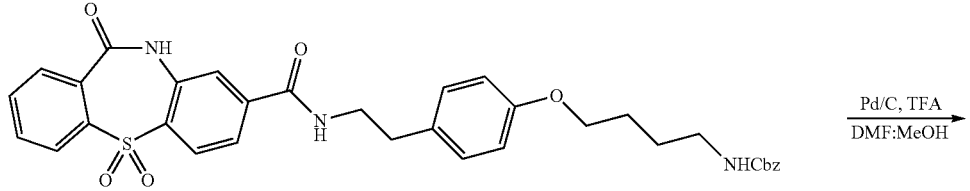

481

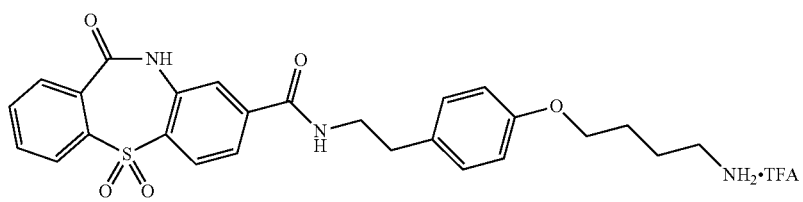

482

Synthesis of 11-oxo-N-(4-(4-((2,2,2-trifluoroacetyl)-λ⁴-azanyl)butoxy) phenethyl)-10,11-dihydrodibenzo[b,f][1,4]thiazepine-8-carboxamide 5,5-dioxide (482)

To a stirred solution of 481 (80 mg, 0.12) (experimental write up shared earlier) in MeOH (10 mL) under inert atmosphere was added Pd/C (50 mg) at RT and stirred under hydrogen atmosphere (balloon pressure) for 5 h. The reaction was monitored by TLC; after completion of the reaction, the reaction mixture was filtered through celite, washed with MeOH (10 mL). The filtrate was concentrated in vacuo, and the crude washed with EtOAc (2×5 mL), n-pentane (5 mL) and dried in vacuo to afford 482 (30 mg, 40%) as an off-white solid. TLC: 5% MeOH/CH$_2$Cl$_2$ (R$_f$: 0.2); $^1$H-NMR (DMSO-d$_6$, 400 MHz): δ 8.78 (t, J=5.0 Hz, 1H), 8.04 (d, J=8.3 Hz, 1H), 8.01-7.96 (m, 2H), 7.94-7.73 (m, 6H), 7.13 (d, J=8.4 Hz, 2H), 6.84 (d, J=8.4 Hz, 2H), 3.93 (t, J=5.7 Hz, 2H), 3.47-3.40 (m, 2H), 2.84 (t, J=7.2 Hz, 2H), 2.75 (t, J=7.1 Hz, 2H), 1.82-1.63 (m, 5H); LC-MS: 94.31%; 494.0 (M$^+$+1); (column; Ascentis Express C18, (50×3.0 mm, 2.7 μm); RT 1.86 min. 0.025% Aq. TFA+5% ACN: ACN+5% 0.025% Aq. TFA, 1.2 mL/min); HPLC (purity): 95.03%; (column; Zorbax SB C-18 (150×4.6 mm, 3.5 μm); RT 6.69 min. 0.05% TFA (Aq): 5% ACN; 1.0 mL; Diluent: ACN:H$_2$O).

Example 46: Synthesis of 776

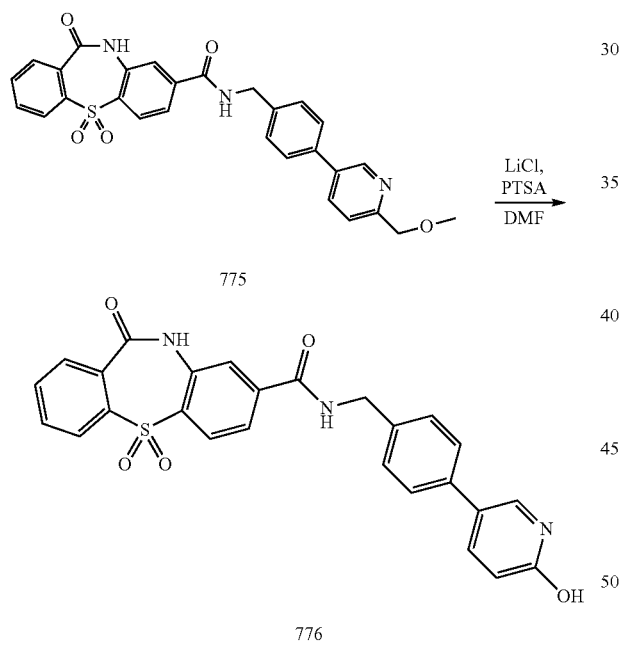

Synthesis of N-(4-(6-hydroxypyridin-3-yl)benzyl)-11-oxo-10,11-dihydrodibenzo[b,f][1,4]thiazepine-8-carboxamide 5,5-dioxide (776)

To a stirring solution of N-(4-(6-methoxypyridin-3-yl)benzyl)-11-oxo-10,11-dihydrodibenzo[b,f][1,4]thiazepine-8-carboxamide 5,5-dioxide (775) (75 mg, 0.15 mmol) in DMF (2 mL) under inert atmosphere were added lithium chloride (32 mg, 0.75 mmol) p-Toluenesulfonic acid (2.5 mg, 0.14 mmol) at RT and stirred for 16 h. The reaction was monitored by TLC; after completion the reaction mixture was diluted with ice-cold water (50 mL) and extracted with EtOAc (2×100 mL The combined organic extracts were dried over sodium sulfate, filtered and concentrated in vacuo to obtain the crude. The crude was purified through silica gel column chromatography using 7% MeOH/CH$_2$Cl$_2$ to afford 776 (30 mg, 41%) as white solid. TLC: 10% MeOH/CH$_2$Cl$_2$ (R$_f$: 0.5); $^1$H-NMR (DMSO-d$_6$, 400 MHz): δ 11.80 (br s, 1H), 11.51 (s, 1H), 9.29 (br t, J=5.5 Hz, 1H), 8.06 (d, J=8.2 Hz, 1H), 8.01-7.96 (m, 2H), 7.93-7.77 (m, 5H), 7.66 (br s, 1H), 7.50 (d, J=8.0 Hz, 2H), 7.32 (d, J=8.0 Hz, 2H), 6.42 (d, J=9.5 Hz, 1H), 4.47 (br d, J=5.6 Hz, 2H); LC-MS: 96.06%; 486.0 (M$^+$+1); (column; Ascentis Express C18, (50×3.0 mm, 2.7 μm); RT 1.95 min. 0.025% Aq. TFA+5% ACN: ACN+5% 0.025% Aq. TFA, 1.2 mL/min); HPLC (purity): 94.53%; (column; Zorbax SB C-18 (150×4.6 mm, 3.5 μm); RT 6.41 min. ACN+5% 0.05% TFA (Aq): 0.05% TFA (Aq)+5% ACN; 1.0 mL/min, Diluent: DMSO:ACN:water).

Example 47: Synthesis of 652-A and 652

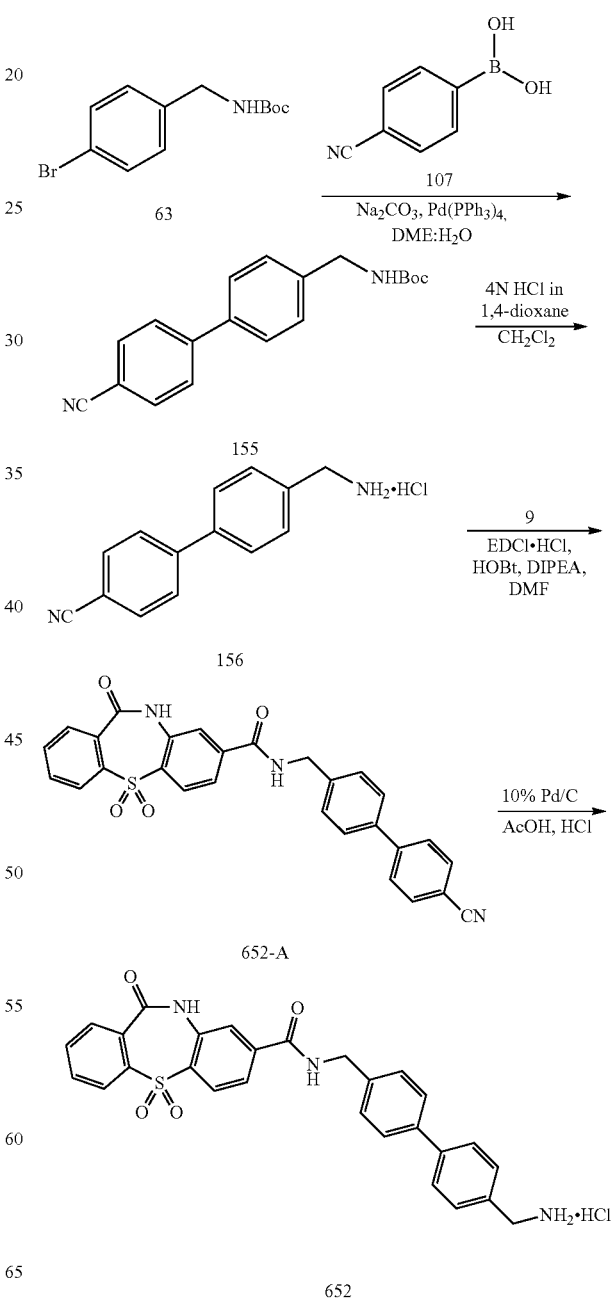

Synthesis of tert-butyl ((4'-cyano-[1,1'-biphenyl]-4-yl)methyl) carbamate (155)

To a stirred solution of tert-butyl (4-bromobenzyl) carbamate 63 (1 g, 3.49 mmol) in 1,2 dimethoxy ethane:H$_2$O (4: 1, 20 mL) were added (4-cyanophenyl) boronic acid 107 (616 mg, 4.19 mmol), sodium carbonate (741 mg, 6.98 mmol) and purged under argon atmosphere for 10 min. To this was added Pd(PPh$_3$)$_4$ (404 mg, 0.34 mmol) at RT; heated to 100° C. and stirred for 16 h. The reaction was monitored by TLC; after completion the reaction mixture was filtered through celite, washed with CH$_2$Cl$_2$ (2×40 mL). The combined organic extracts were dried over sodium sulfate, filtered and concentrated in vacuo to obtain the crude. The crude was purified through silica gel flash column chromatography using 20% EtOAc/hexanes to afford compound 155 (850 mg, 79%) as yellow solid. TLC: 20% EtOAc/hexanes (R$_f$: 0.5); $^1$H-NMR (DMSO-d$_6$, 400 MHz): δ 7.91 (d, J=8.4 Hz, 2H), 7.87 (d, J=8.4 Hz, 2H), 7.71 (d, J=7.8 Hz, 2H), 7.44 (t, J=5.9 Hz, 1H), 7.37 (d, J=8.1 Hz, 2H), 4.18 (d, J=6.1 Hz, 2H), 1.40 (s, 9H).

Synthesis of 4'-(aminomethyl)-[1,1'-biphenyl]-4-carbonitrile hydrochloride (156)

To a stirred solution of compound 155 (650 mg, 2.10 mmol) in CH$_2$Cl$_2$ (10 mL) under inert atmosphere was added 4 N HCl in 1,4-dioxane (5 mL) at 0° C.; warmed to RT and stirred for 3 h. The reaction was monitored by TLC; after completion of the reaction, the volatiles were removed in vacuo to obtain the crude. The crude was washed with diethyl ether (2×15 mL) and dried in vacuo to afford compound 156 (450 mg, 87%) as an off-white solid. TLC: 20% EtOAc/hexanes (R$_f$: 0.2); $^1$H-NMR (DMSO-d$_6$, 400 MHz): δ 8.52 (br s, 3H), 7.98-7.89 (m, 4H), 7.82 (d, J=8.3 Hz, 2H), 7.64 (d, J=8.3 Hz, 2H), 4.08 (br s, 2H).

Synthesis of N-((4'-cyano-[1,1'-biphenyl]-4-yl)methyl)-11-oxo-10,11-dihydrodibenzo[b,f][1,4]thiazepine-8-carboxamide 5,5-dioxide (652-A)

To a stirred solution of compound 9 (200 mg, 0.66 mmol) in DMF (8 mL) under inert atmosphere were added EDCI.HCl (190 mg, 0.99 mmol), HOBt (134 mg, 0.99 mmol) and diisopropylethylamine (0.34 mL, 1.98 mmol) and compound 156 (194 mg, 0.79 mmol) at 0° C.; warmed to RT and stirred for 16 h. The reaction was monitored by TLC; after completion of the reaction, the reaction mixture was diluted with ice-cold water (50 mL) and extracted with EtOAc (2×50 mL). The combined organic extracts were dried over sodium sulfate, filtered and concentrated in vacuo to obtain the crude. The crude was purified through silica gel column chromatography using 3% MeOH/CH$_2$Cl$_2$ to afford 652-A (230 mg, 71%) as white solid. TLC: 5% MeOH/CH$_2$Cl$_2$ (R$_f$: 0.4); $^1$H NMR (DMSO-d$_6$, 400 MHz): δ 11.36 (br s, 1H), 9.34 (t, J=5.9 Hz, 1H), 8.06 (d, J=8.2 Hz, 1H), 7.98 (dd, J=8.7, 1.1 Hz, 2H), 7.93-7.83 (m, 8H), 7.71 (d, J=8.4 Hz, 2H), 7.43 (d, J=8.3 Hz, 2H), 4.52 (d, J=5.9 Hz, 2H); LC-MS: 98.68%; 494.7 (M$^+$+1); (column; Ascentis Express C18, (50×3.0 mm, 2.7 µm); RT 2.54 min. 0.025% Aq. TFA+5% ACN: ACN+5% 0.025% Aq. TFA, 1.2 mL/min); HPLC (purity): 98.25%; (column; Zorbax SB C-18 (150×4.6 mm, 3.5 µm); RT 9.28 min. ACN: 0.05% TFA (Aq); 1.0 mL/min, Diluent: ACN:water).

Synthesis of N-((4'-(aminomethyl)-[1,1'-biphenyl]-4-yl)methyl)-11-oxo-10,11-dihydrodibenzo[b,f][1,4]thiazepine-8-carboxamide 5,5-dioxide hydrochloride (652)

To a stirred solution of compound 652-A (100 mg, 0.20 mmol) in acetic acid (10 mL) under inert atmosphere were added 10% Pd/C (50 mg) at RT and stirred under hydrogen atmosphere (balloon pressure) for 6 h. The reaction was monitored by TLC; after completion of the reaction, the reaction mixture was filtered through celite, washed with 40% MeOH/CH$_2$Cl$_2$ (2×20 mL). The filtrate was dried over sodium sulfate, filtered and concentrated in vacuo to obtain the crude. The pH of the residue of the crude was adjusted to ~2 using 2 N HCl and stirred for 20 min. The aqueous layer was washed with EtOAc (2×20 mL). The aqueous layer was concentrated in vacuo to obtain the crude which triturated with diethyl ether (2×10 mL) to afford compound 652 (70 mg, 65%) as an off-white solid. TLC: 5% MeOH/CH$_2$Cl$_2$ (R$_f$: 0.2); $^1$H NMR (DMSO-d$_6$, 400 MHz): 11.54 (s, 1H), 9.37 (t, J=5.7 Hz, 1H), 8.35 (br s, 3H), 8.06 (d, J=8.0 Hz, 2H), 7.98 (td, J=7.9, 1.0 Hz, 2H), 7.93-7.83 (m, 4H), 7.70 (d, J=8.2 Hz, 2H), 7.64 (d, J=8.3 Hz, 2H), 7.55 (d, J=8.3 Hz, 2H), 7.40 (d, J=8.0 Hz, 2H), 4.50 (d, J=5.6 Hz, 2H), 4.05 (q, J=5.5 Hz, 2H); LC-MS: 97.74%; 498.0 (M$^+$+1); (column; Ascentis Express C18, (50×3.0 mm, 2.7 µm); RT 1.88 min. 0.025% Aq. TFA+5% ACN:ACN+5% 0.025% Aq. TFA, 1.2 mL/min); HPLC (purity): 97.49%; (column; Zorbax SB C-18 (150×4.6 mm, 3.5 µm); RT 6.31 min. ACN: 0.05% TFA (Aq); 1.0 mL/min, Diluent: ACN:water).

Example 48: Synthesis of 765

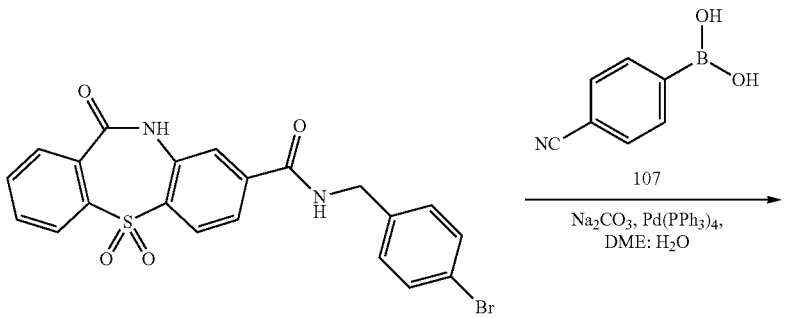

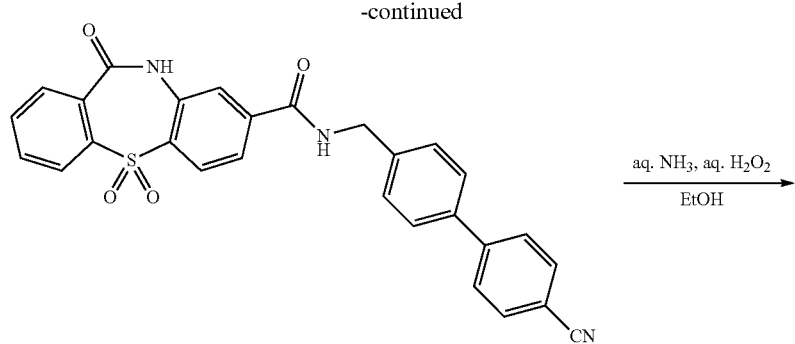

652-A

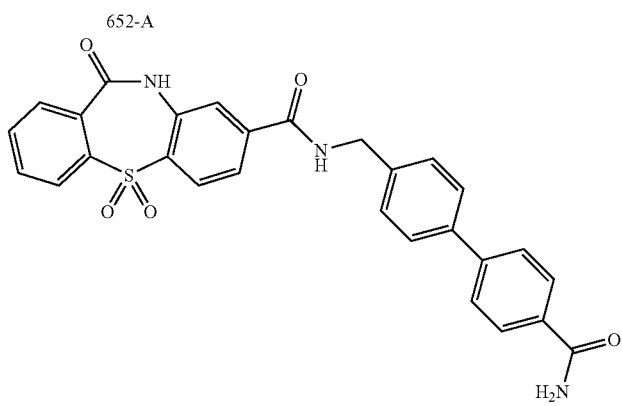

765

Synthesis of N-((4(4'-carbamoyl-[1,1'-biphenyl]-4-yl) methyl)-11-oxo-10,11-dihydrodibenzo[b,f][1,4]thiazepine-8-carboxamide 5,5-dioxide (765)

To a stirring solution of 652-A (50 mg, 0.10 mmol) in EtOH (3 mL) were added aqueous ammonia (1 mL, 1.01 mmol) and 30% aqueous H$_2$O$_2$ (1 mL) at 10° C.; warmed to RT and stirred for 2 h. The reaction was monitored by TLC; after completion of the reaction, the volatile were removed in vacuo. The precipitated solid was filtered and dried in vacuo to afford 765 (40 mg, 77%) as white solid. TLC: 5% MeOH/CH$_2$Cl$_2$ (R$_f$: 0.4). $^1$H-NMR (DMSO-d$_6$, 500 MHz): δ 11.47 (br s, 1H), 9.32 (t, J=5.8 Hz, 1H), 8.06 (d, J=8.4 Hz, 1H), 8.01-7.93 (m, 5H), 7.93-7.83 (m, 4H), 7.72 (d, J=8.4 Hz, 2H), 7.68 (d, J=8.1 Hz, 2H), 7.41 (d, J=8.1 Hz, to 2H), 7.36 (br s, 1H), 4.52 (d, J=5.8 Hz, 2H); LC-MS: 98.19%; 512.0 (M$^+$+1); (column; Ascentis Express C18, (50×3.0 mm, 2.7 nm); RT 2.12 min. 0.025% Aq. TFA+5% ACN:ACN+5% 0.025% Aq. TFA, 1.2 mL/min); HPLC (purity): 98.43%; (column; X-select CSH C-18 (150×4.6 mm, 3.5 μm); RT 7.64 min. ACN+5% 0.05% TFA (Aq): 0.05% TFA (Aq)+5% ACN; 1.0 mL/min, Diluent: DMSO:ACN:water).

Example 49: Synthesis of 676

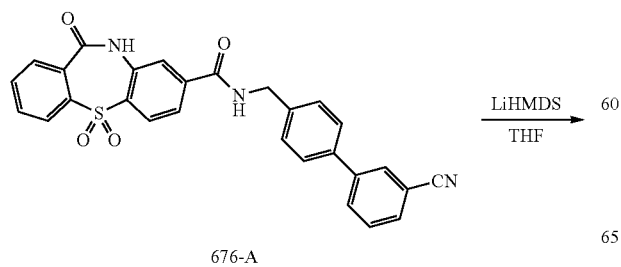

676-A

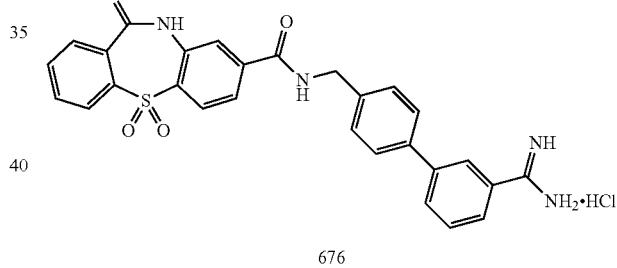

676

Synthesis of N-((3'-carbamimidoyl-[1,1'-biphenyl]-4-yl) methyl)-11-oxo-10,11-dihydrodibenzo[b,f][1,4]thiazepine-8-carboxamide 5,5-dioxide hydrochloride (676) (SAP-MA1521-32)

To a stirring solution of 676-A (150 mg, 0.30 mmol) in dry THF (10 mL) under inert atmosphere was added LiHMDS (1 M solution in THF, 3.1 mL) at 0° C.; warmed to RT and stirred for 16 h. The reaction was monitored by TLC; after completion of the reaction, the reaction mixture was quenched with ice-cold water (10 mL), the aqueous layer was concentrated in vacuo to obtain the crude.

To the above crude compound under inert atmosphere was added 4 N HCl in 1,4-dioxane (2 mL) and stirred for 15 min. The volatiles were removed in vacuo to obtain the crude. The crude was purified by preparative HPLC purification. The obtained solid was triturated with 30% CH$_2$Cl$_2$/n-pentane (2 mL) to afford 676 (80 mg, 51%) as white solid. TLC: 5% MeOH/CH$_2$Cl$_2$ (R$_f$: 0.2); $^1$H NMR (DMSO-d$_6$, 400 MHz): δ 11.54 (s, 1H), 9.42-9.32 (m, 3H), 9.12 (s, 2H), 8.09-8.05 (m, 2H), 8.03-7.96 (m, 3H), 7.94-7.84 (m, 4H), 7.80-7.73 (m, 3H), 7.72-7.67 (m, 1H), 7.45 (d, J=8.4 Hz, 2H), 4.53 (d, J=5.8 Hz, 2H); LC-MS: 98.82%; 511.1 (M⁺+1); (column; Ascentis Express C18, (50×3.0 mm, 2.7 μm); RT 1.86 min. 0.025% Aq. TFA+5% ACN:ACN+5% 0.025% Aq. TFA, 1.2 mL/min); HPLC (purity): 98.31%; (column; Zorbax SB-C-18 (150×4.6 mm, 3.5 μm); RT 6.20 min. ACN+5% 0.05% TFA (Aq): 0.05% TFA (Aq)+5% ACN; 1.0 mL/min, Diluent: DMSO:ACN:water).

Example 50: Synthesis of 808

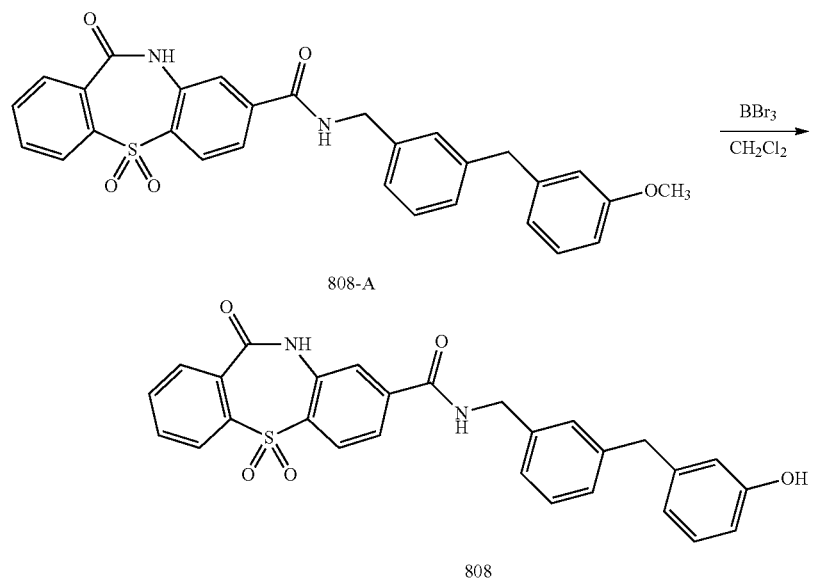

808

Synthesis of N-(3-(3-hydroxybenzyl) benzyl)-11-oxo-10,11-dihydrodibenzo[b,f][1,4]thiazepine-8-carboxamide 5,5-dioxide (808)

To a stirring solution of N-(3-(3-methoxybenzyl) benzyl)-11-oxo-10,11-dihydrodibenzo[b,f][1,4]thiazepine-8-carboxamide 5,5-dioxide (808-A) (180 mg, 0.35 mmol) in CH₂Cl₂ (15 mL) was added BBr₃ (0.16 mL, 1.75 mmol) at 0° C.; warmed to RT and stirred for 16 h. The reaction was monitored by TLC; after completion of the reaction, the reaction mixture was quenched with ice-cold water (10 mL), added 10% NaHCO₃ solution and stirred for 30 min. The precipitated solid was filtered, washed with water (10 mL) and dried in vacuo to obtain the crude which was triturated with MeOH (10 mL), n-pentane (10 mL) and dried in vacuo to afford 808 (70 mg, 40%) as an off-white solid. TLC: 10% MeOH/CH₂Cl₂ (R$_f$: 0.4); ¹H-NMR (DMSO-d₆, 400 MHz): δ 11.50 (s, 1H), 9.26-9.21 (m, 2H), 8.05 (d, J=8.3 Hz, 1H), 8.01-7.95 (m, 2H), 7.93-7.78 (m, 4H), 7.23 (t, J=7.5 Hz, 1H), 7.15-7.06 (m, 3H), 7.03 (t, J=7.8 Hz, 1H), 6.62 (dtJ=7.8, 1.4 Hz, 1H), 6.58-6.52 (m, 2H), 4.43 (d, J=5.9 Hz, 2H), 3.81 (s, 2H); LC-MS: 94.64%; 499.1 (M⁺+1); (column; Ascentis Express C18, (50×3.0 mm, 2.7 μm); RT 2.42 min. 0.025% Aq. TFA+5% ACN:ACN+5% 0.025% Aq. TFA, 1.2 mL/min); HPLC (purity): 94.44%; (column; X-select CSH C-18 (150×4.6 mm, 3.5 μm); RT 9.27 min. 5% 0.05% TFA+5% ACN:ACN+5% 0.05% ACN; 1.0 mL/min, Diluent: DMSO:ACN:water).

Example 51: Synthesis of 809

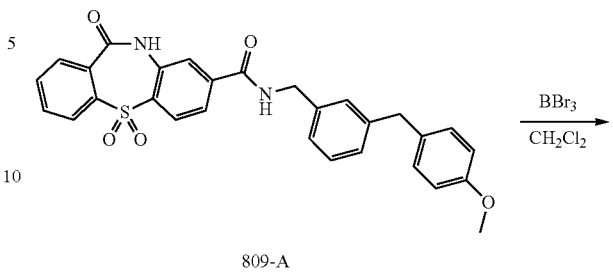

809-A

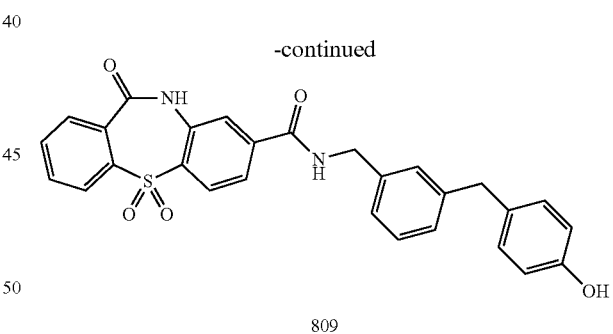

809

Synthesis of N-(3-(4-hydroxybenzyl)benzyl)-11-oxo-10,11-dihydrodibenzo[b,f][1,4]thiazepine-8-carboxamide 5,5-dioxide (809)

To a stirring solution of N-(3-(4-methoxybenzyl) benzyl)-11-oxo-10,11-dihydrodibenzo[b,f][1,4]thiazepine-8-carboxamide 5,5-dioxide (809-A) (145 mg, 0.28 mmol) in CH₂Cl₂ (5 mL) was added BBr₃ (0.13 mL, 1.41 mmol) at 0° C.; warmed to RT and stirred for 16 h. The reaction was monitored by TLC; after completion of the reaction, the reaction mixture was quenched with ice-cold water (10 mL) and extracted with EtOAc (2×150 mL). The combined organic extracts were washed with 10% NaHCO3, dried over sodium sulfate, filtered and concentrated in vacuo to obtain the crude. The crude was triturated with 20% EtOAc/hexanes (10 mL) and dried in vacuo to afford 809 (95 mg, 67%) as white solid. TLC: 5% MeOH/CH$_2$Cl$_2$ (R$_f$: 0.5); $^1$H NMR (DMSO-d$_6$, 400 MHz): δ 11.51 (br s, 1H), 9.23 (t, J=5.7 Hz, 1H), 9.16 (br s, 1H), 8.05 (d, J=8.2 Hz, 1H), 8.01-7.95 (m, 2H), 7.94-7.78 (m, 4H), 7.24-7.18 (m, 1H), 7.15-7.03 (m, 3H), 6.98 (d, J=8.3 Hz, 2H), 6.65 (d, J=8.3 Hz, 2H), 4.42 (d, J=5.6 Hz, 2H), 3.78 (s, 2H); LC-MS: 95.63%; 499.1 (M$^+$+1); (column; Ascentis Express C18, (50×3.0 mm, 2.7 μm); RT 2.39 min. 0.025% Aq. TFA+5% ACN:ACN+5% 0.025% Aq. TFA, 1.2 mL/min); HPLC (purity): 96.09%; (column; X-select CSH C-18 (150×4.6 mm, 3.5 μm); RT 9.19 min. ACN+5% 0.05% TFA: 0.05% TFA+5% ACN (Aq); 1.0 mL/min, Diluent: DMSO:ACN:water).

Example 52: Synthesis of 810

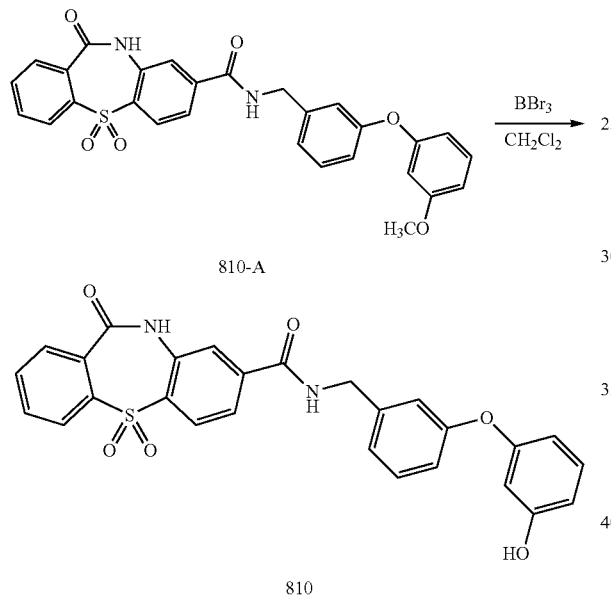

810

Synthesis of N-(3-(3-hydroxyphenoxy) benzyl)-11-oxo-10,11-dihydrodibenzo[b,f][1,4]thiazepine-8-carboxamide 5,5-dioxide (810)

To a stirring solution of N-(3-(3-methoxyphenoxy) benzyl)-11-oxo-10,11-dihydrodibenzo[b,f][1, 4]thiazepine-8-carboxamide 5,5-dioxide (810-A) (80 mg, 0.15 to mmol) in CH$_2$Cl$_2$ (5 mL) was added BBr$_3$ (0.08 mL, 0.77 mmol) at 0° C.; warmed to RT and stirred for 16 h. The reaction was monitored by TLC; after completion of the reaction, the reaction mixture was quenched with ice-cold water (10 mL) and extracted with EtOAc (2×70 mL). The combined organic extracts were dried over sodium sulfate, filtered and concentrated in vacuo to obtain the crude. The crude was purified through silica gel column (100-200 mesh) chromatography using 2% MeOH/CH$_2$Cl$_2$ to afford 810 (30 mg, 39%) as white solid. TLC: 5% MeOH/CH$_2$Cl$_2$ (R$_f$: 0.5); $^1$H-NMR (DMSO-d$_6$, 500 MHz): δ 11.50 (br s, 1H), 9.56 (br s, 1H), 9.28 (t, J=5.9 Hz, 1H), 8.05 (d, J=8.3 Hz, 1H), 7.98 (td, J=7.8, 1.0 Hz, 2H), 7.93-7.78 (m, 4H), 7.32 (t, J=7.8 Hz, 1H), 7.12 (t, J=8.1 Hz, 1H), 7.06 (d, J=7.5 Hz, 1H), 6.95 (s, 1H), 6.87 (dd, J=8.0, 1.8 Hz, 1H), 6.50 (dd, J=8.0, 1.5 Hz, 1H), 6.39 (dd, J=8.1, 1.6 Hz, 1H), 6.34 (t, J=2.2 Hz, 1H), 4.45 (d, J=5.6 Hz, 2H); LC-MS: 95.93%; 501.0 (M$^+$+1); (column; Ascentis Express C18, (50×3.0 mm, 2.7 μm); RT 2.38 min. 0.025% Aq. TFA+5% ACN:ACN+5% 0.025% Aq. TFA, 1.2 mL/min); HPLC (purity): 94.99%; (column; X-select CSH C-18 (150×4.6 mm, 3.5 μm); RT 9.15 min. 5% 0.05% TFA+5% ACN (Aq):ACN+5% 0.05% TFA; 1.0 mL/min, Diluent: DMSO:ACN:water)

Example 53: Synthesis of 811

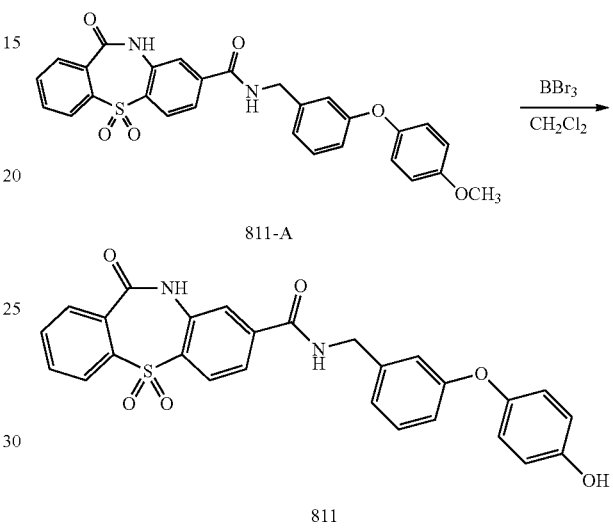

811

Synthesis of N-(3-(4-hydroxyphenoxy)benzyl)-11-oxo-10,11-dihydrodibenzo[b,f][1,4]thiazepine-8-carboxamide 5,5-dioxide (811)

To a stirring solution of N-(3-(4-methoxyphenoxy) benzyl)-11-oxo-10,11-dihydrodibenzo[b,f][1,4]thiazepine-8-carboxamide 5,5-dioxide (811-A) (100 mg, 0.19 mmol) in CH$_2$Cl$_2$ (5 mL) was added BBr$_3$ (0.094 mL, 0.97 mmol) at 0° C.; warmed to RT and stirred for 16 h. The reaction was monitored by TLC; after completion of the reaction, the reaction mixture was quenched with ice-cold water (10 mL) and extracted with EtOAc (2×80 mL). The combined organic extracts were dried over sodium sulfate, filtered and concentrated in vacuo to obtain the crude. The crude was purified through silica gel column (100-200 mesh) chromatography using 2% MeOH/CH$_2$Cl$_2$ and further purified by precipitation with N-methyl pyrrolidinone: H$_2$O (10: 1, 22 mL); the obtained solid was filtered and dried in vacuo to afford 811 (70 mg, 72%) as white solid. TLC: 5% MeOH/CH$_2$Cl$_2$ (R$_f$: 0.5); $^1$H-NMR (DMSO-d$_6$, 400 MHz): δ 11.50 (br s, 1H), 9.40-9.28 (m, 1H), 9.24 (t, J=6.0 Hz, 1H), 8.04 (d, J=8.3 Hz, 1H), 8.01-7.95 (m, 2H), 7.93-7.81 (m, 3H), 7.78 (dd, J=8.3, 1.1 Hz, 1H), 7.25 (t, J=7.9 Hz, 1H), 6.96 (d, J=7.5 Hz, 1H), 6.88-6.83 (m, 3H), 6.79-6.71 (m, 3H), 4.41 (d, J=5.8 Hz, 2H); LC-MS: 98.91%; 501.0 (M$^+$+1); (column; Ascentis Express C18, (50×3.0 mm, 2.7 μm); RT 2.31 min. 0.025% Aq. TFA+5% ACN: ACN+5% 0.025% Aq. TFA, 1.2 mL/min); HPLC (purity): 94.32%; (column; X-select CSH C-18 (150×4.6 mm, 3.5 μm); RT 8.84 min. ACN+5% 0.05% TFA 0.05% TFA+5% ACN; 1.0 mL/min, Diluent: DMSO: ACN:water)

113

Example 54: Synthesis of 812

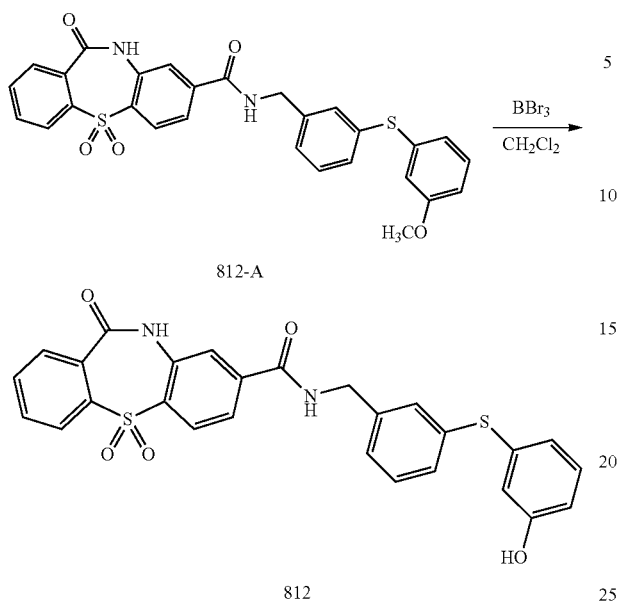

Synthesis of N-(3-((3-hydroxyphenyl)thio)benzyl)-11-oxo-10,11-dihydrodibenzo[b,f][1,4]thiazepine-8-carboxamide 5,5-dioxide (812)

To a stirring solution of N-(3-((3-methoxyphenyl)thio)benzyl)-11-oxo-10,11-dihydrodibenzo[b,f][1,4]thiazepine-8-carboxamide 5,5-dioxide (812-A) (100 mg, 0.18 mmol) in CH$_2$Cl$_2$ (10 mL) was added BBr$_3$ (0.03 mL, 0.37 mmol) at 0-5° C.; warmed to RT and stirred for 16 h. The reaction was monitored by TLC; after completion of the reaction, the reaction mixture was quenched with ice-cold water (5 mL) and pH was adjusted to ~7 with saturated NaHCO3 solution. The precipitated solid was filtered dried in vacuo to obtain the crude. The obtained solid was purified by precipitation with N-methyl pyrrolidine: saturated NaHCO$_3$ (1: 10, 22 mL) and stirred for 1 h. The precipitated solid was filtered, washed with water (10 mL), filtered and dried in vacuo to afford compound 812 (50 mg, 52%) as an off-white solid. TLC: 10% MeOH/CH$_2$Cl$_2$ (R$_f$: 0.4); $^1$H NMR (DMSO-d$_6$, 400 MHz): δ 11.50 (br s, 1H), 9.59 (br s, 1H), 9.27 (br s, 1H), 8.08-7.76 (m, 7H), 7.37-7.06 (m, 5H), 6.76-6.58 (m, 3H), 4.44 (d, J=5.0 Hz, 2H); LC-MS: 96.45%; 517.0 (M$^+$+1); (column; Ascentis Express C18, (50×3.0 mm, 2.7 μm); RT 2.48 min. 0.025% Aq. TFA+5% ACN:ACN+5% 0.025% Aq. TFA, 1.2 mL/min); HPLC (purity): 96.82%; (column; X-Select CSH C-18 (150×4.6 mm, 3.5 μm); RT 9.60 min. ACN: 0.05% TFA (Aq); 1.0 mL/min, Diluent: ACN:water).

Example 55: Synthesis of 726

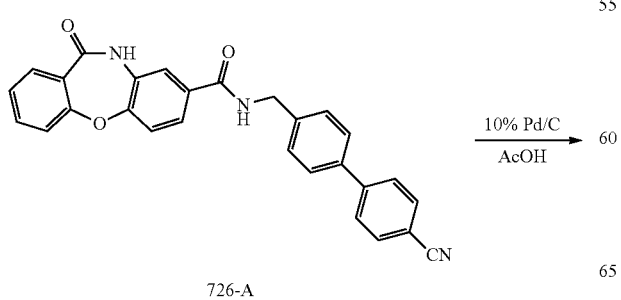

114

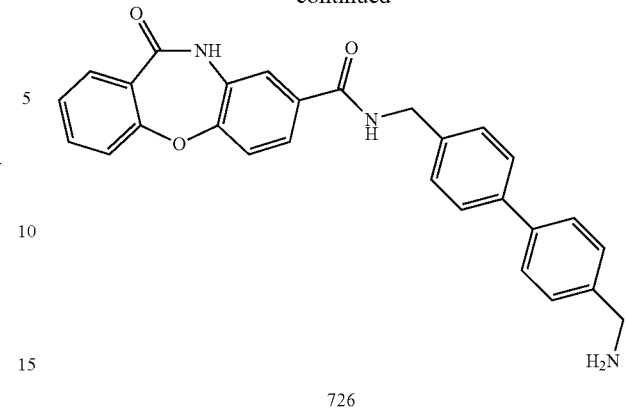

Synthesis of N-((4(4'-(aminomethyl)-[1,1'-biphenyl]-4-yl)methyl)-11-oxo-10,11-dihydrodibenzo[b,f][1,4]oxazepine-8-carboxamide (726)

To a stirring solution of 726-A (150 mg, 0.33 mmol) in acetic acid (10 mL) under inert atmosphere was added 10% Pd/C (50% wet, 50 mg) at RT and stirred under hydrogen atmosphere (balloon pressure) at RT for 16 h. The reaction was monitored by TLC; after completion of the reaction, the reaction mixture was filtered through celite and washed with 50% MeOH/CH$_2$Cl$_2$ (3×20 mL). The filtrate was concentrated in vacuo to obtain the crude. The crude was triturated with MeOH (5 mL), EtOAc (2×5 mL), further purified by preparative HPLC purification to afford 726 (25 mg, 17%) as an off-white solid. TLC: 5% MeOH/CH$_2$Cl$_2$ (R$_f$: 0.2); $^1$H-NMR (DMSO-d$_6$, 400 MHz): δ 10.62 (br s, 1H), 9.05 (br s, 1H), 7.87-7.77 (m, 1H), 7.84-7.50 (m, 7H), 7.48-7.27 (m, 7H), 4.48 (br d, J=5.1 Hz, 2H), 3.74 (br s, 2H); LC-MS: 99.71%; 450.3 (M$^+$+1); (column; Ascentis Express C18, (50×3.0 mm, 2.7 μm); RT 1.88 min. 0.025% Aq.TFA+5% ACN:ACN+5% 0.025% Aq TFA, 1.2 mL/min). HPLC (purity): 97.42%; (column; X-select CSH C-18 (150×4.6 mm, 3.5 μm); RT 6.42 min. ACN+5% 0.05% TFA (Aq): 0.05% TFA (Aq)+5% ACN; 1.0 mL/min, Diluent: ACN:water).

Example 56: Synthesis of 741

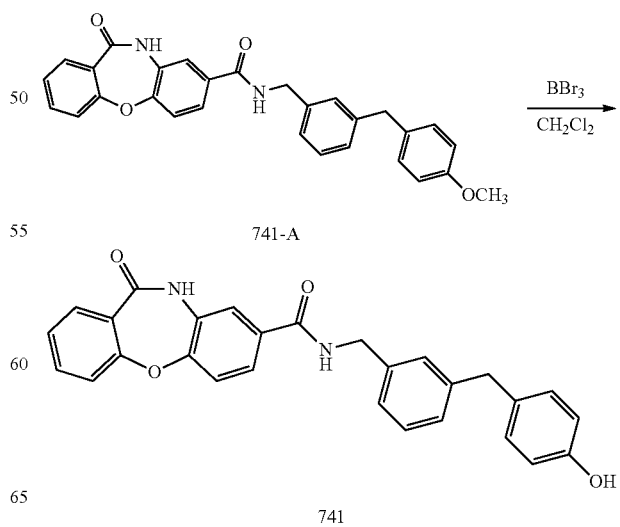

Synthesis of N-(3-(4-hydroxybenzyl) benzyl)-11-oxo-10,11-dihydrodibenzo[b,f][1,4]oxazepine-8-carboxamide (741)

To a stirring solution of 741-A (150 mg, 0.32 mmol) in $CH_2Cl_2$ (5 mL) was added $BBr_3$ (405 mg, 1.61 mmol) at 0° C.; warmed to RT and stirred for 16 h. The reaction was monitored by TLC; after completion of the reaction, the reaction mixture was cooled to 0° C., quenched with ice-cold water (50 mL) and extracted with EtOAc (2×150 mL). The combined organic extracts were dried over sodium sulfate, filtered and concentrated in vacuo to obtain the crude. The crude was triturated with 20% EtOAc/hexanes to afford 741 (115 mg, 80%) as white solid. TLC: 5% MeOH/$CH_2Cl_2$ ($R_f$: 0.5); $^1$H NMR (DMSO-$d_6$, 400 MHz): δ 10.63 (s, 1H), 9.16 (s, 1H), 8.99 (t, J=5.9 Hz, 1H), 7.78 (dd, J=7.7, 1.6 Hz, 1H), 7.68 (s, 1H), 7.66-7.60 (m, 2H), 7.44-7.31 (m, 3H), 7.21 (t, J=7.5 Hz, 1H), 7.15-7.02 (m, 3H), 6.98 (d, J=8.4 Hz, 2H), 6.65 (d, J=8.4 Hz, 2H), 4.40 (d, J=5.8 Hz, 2H), 3.78 (s, 2H); LC-MS: 95.40%; 451.0 ($M^+$+1); (column; Ascentis Express C18, (50×3.0 mm, 2.7 μm); RT 2.40 min. 0.025% Aq. TFA+5% ACN:ACN+5% 0.025% Aq. TFA, 1.2 mL/min); HPLC (purity): 95.12%; (column; Zorbax SB-C-18 (150×4.6 mm, 3.5 μm); RT 8.82 min. ACN+5% 0.05% TFA (Aq): 0.05% TFA (Aq)+5% ACN; 1.0 mL/min, Diluent: DMSO:ACN:water).

filtered and concentrated in vacuo to obtain the crude. The crude was triturated with EtOAc (2×5 mL). The obtained solid was purified by precipitation with N-methyl pyrrolidine: $H_2O$ (1: 10, 22 mL) to afford 744 (55 mg, 57%) as white solid. TLC: 5% MeOH/$CH_2Cl_2$ ($R_f$: 0.4); $^1$H NMR (DMSO-$d_6$, 500 MHz): δ 10.62 (s, 1H), 9.56 (s, 1H), 9.03 (t, J=5.6 Hz, 1H), 7.78 (d, J=7.2 Hz, 1H), 7.69-7.61 (m, 3H), 7.42 (d, J=8.1 Hz, 1H), 7.39-7.30 (m, 3H), 7.13 (t, J=8.1 Hz, 1H), 7.06 (d, J=7.5 Hz, 1H), 6.95 (br s, 1H), 6.86 (d, J=7.8 Hz, 1H), 6.51 (d, J=6.9 Hz, 1H), 6.39 (d, J=8.1 Hz, 1H), 6.34 (br s, 1H), 4.43 (d, J=5.8 Hz, 2H); LC-MS: 96.19%; 453.0 ($M^+$+1); (column; Ascentis Express C18, (50×3.0 mm, 2.7 μm); RT 2.40 min. 0.025% Aq. TFA+5% ACN: ACN+5% 0.025% Aq. TFA, 1.2 mL/min); HPLC (purity): 95.17%; (column; X-Select CSH—C-18 (150×4.6 mm, 3.5 μm); RT 9.01 min. ACN+5% 0.05% TFA (Aq): 0.05% TFA (Aq)+5% ACN; 1.0 mL/min, Diluent: DMSO:ACN:water).

Example 58: Synthesis of 745

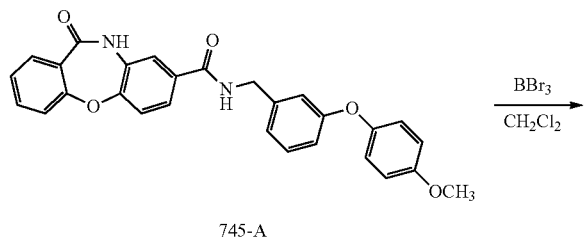

745-A

Example 57: Synthesis of 744

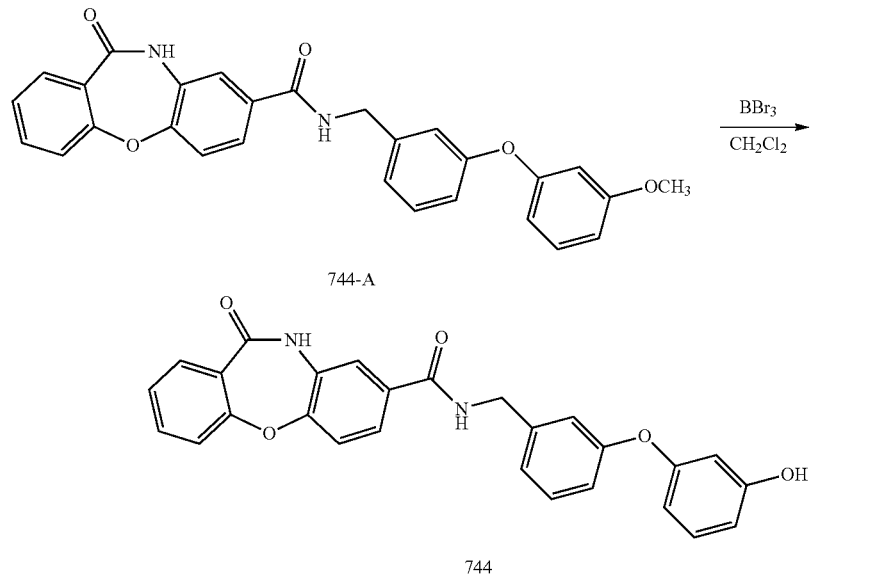

744-A

744

Synthesis of N-(3-(3-hydroxyphenoxy)benzyl)-11-oxo-10,11-dihydrodibenzo[b,f][1,4]oxazepine-8-carboxamide (744)

To a stirring solution of N-(3-(3-methoxyphenoxy) benzyl)-11-oxo-10,11-dihydrodibenzo[b,f][1,4]oxazepine-8-carboxamide (744-A) (100 mg, 0.21 mmol) in $CH_2Cl_2$ (5 mL) was added $BBr_3$ (0.1 mL, 1.07 mmol) at 0° C.; warmed to RT and stirred for 16 h. The reaction was monitored by TLC; after completion of the reaction, the reaction mixture was cooled to 0° C., quenched with ice-cold water (20 mL) and extracted with 10% MeOH/$CH_2Cl_2$ (2×30 mL). The combined organic extracts were dried over sodium sulfate, -continued

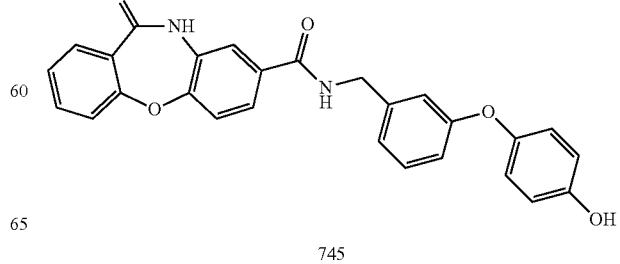

745

Synthesis of N-(3-(4-hydroxyphenoxy)benzyl)-11-oxo-10,11-dihydrodibenzo[b,f][1,4]oxazepine-8-carboxamide (745)

To a stirring solution of N-(3-(4-methoxyphenoxy) benzyl)-11-oxo-10,11-dihydrodibenzo[b,f][1,4]oxazepine-8-carboxamide (745-A) (100 mg, 0.21 mmol) in CH$_2$Cl$_2$ (5 mL) was added BBr$_3$ (0.1 mL, 1.07 mmol) at 0° C.; warmed to RT and stirred for 16 h. The reaction was monitored by TLC; after completion of the reaction, the reaction mixture was cooled to 0° C., quenched with ice-cold water (20 mL) and extracted with 10% MeOH/CH$_2$Cl$_2$ (2×30 mL). The combined organic extracts were dried over sodium sulfate, filtered and concentrated in vacuo to obtain the crude. The crude was triturated with CH$_3$CN (5 mL), MeOH (5 mL), EtOAc (2×5 mL), further purified through silica gel (100-200 mesh) flash column chromatography using 3% MeOH/CH$_2$Cl$_2$. The obtained solid was purified by precipitation with N-methyl pyrrolidine:H$_2$O (1: 10, 22 mL) to afford 745 (30 mg, 31%) as white solid. TLC: 5% MeOH/CH$_2$Cl$_2$ (R$_f$: 0.4); $^1$H NMR (DMSO-d$_6$, 500 MHz): δ 10.62 (s, 1H), 9.31 (s, 1H), 9.00 (t, J=5.9 Hz, 1H), 7.78 (dd, J=7.7, 1.3 Hz, 1H), 7.71-7.59 (m, 3H), 7.42 (d, J=8.4 Hz, 1H), 7.38-7.32 (m, 2H), 7.25 (t, J=7.8 Hz, 1H), 6.96 (d, J=7.5 Hz, 1H), 6.88-6.84 (m, 3H), 6.76 (d, J=8.7 Hz, 2H), 6.72 (dd, J=8.1, 1.7 Hz, 1H), 4.40 (d, J=6.1 Hz, 2H); LC-MS: 98.69%; 453.1 (M$^+$+1); (column; Ascentis Express C18, (50×3.0 mm, 2.7 µm); RT 2.36 min. 0.025% Aq. TFA+5% ACN:ACN+5% 0.025% Aq. TFA, 1.2 mL/min); HPLC (purity): 98.22%; (column; X-Select CSH-C-18 (150×4.6 mm, 3.5 µm); RT 8.79 min. ACN+5% 0.05% TFA (Aq): 0.05% TFA (Aq)+5% ACN; 1.0 mL/min, Diluent: DMSO:ACN:water).

Example 59: Synthesis of 742

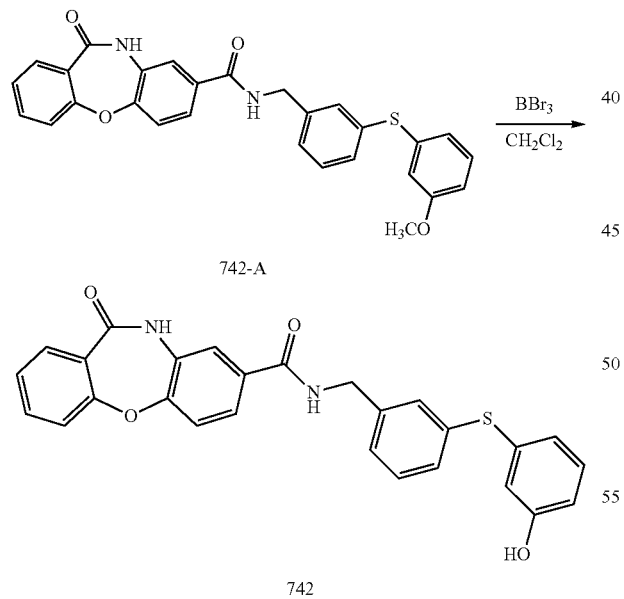

Synthesis of N-(3-((3-hydroxyphenyl)thio)benzyl)-11-oxo-10,11-dihydrodibenzo[b,f][1,4]oxazepine-8-carboxamide (742)

To a stirring solution of N-(3-((3-methoxyphenyl) thio)benzyl)-11-oxo-10,11-dihydrodibenzo[b,f][1,4]oxazepine-8-carboxamide 742-A (80 mg, 0.16 mmol) in CH$_2$Cl$_2$ (10 mL) was added BBr3 (0.07 mL, 0.82 mmol) at 0° C. dropwise; warmed to RT and stirred for 16 h. The reaction was monitored by TLC; after completion of the reaction, the pH of the reaction mixture was adjusted ~4 with saturated NaHCO$_3$ solution. The obtained solid was in filtered, washed with water (5 mL) and dried in vacuo to afford compound 742 (52 mg, 67%) as an off-white solid. TLC: 10% MeOH/CH$_2$Cl$_2$ (R$_f$: 0.2); $^1$H-NMR (DMSO-d$_6$, 400 MHz): δ 10.63 (s, 1H), 9.60 (s, 1H), 9.04 (br t, J=5.3 Hz, 1H), 7.79 (d, J=7.4 Hz, 1H), 7.70-7.59 (m, 3H), 7.46-7.06 (m, 8H), 6.75-6.54 (m, 3H), 4.43 (br d, J=5.4 Hz, 2H); LC-MS: 97.83%; 469.0 (M$^+$+1); (column; Ascentis Express C18, (50×3.0 mm, 2.7 µm); RT 2.49 min. 0.025% Aq. TFA+5% ACN:ACN+5% 0.025% Aq. TFA, 1.2 mL/min); HPLC (purity): 95.35%; (column; Zorbax SB C-18 (150×4.6 mm, 3.5 µm); RT 9.15 min. ACN+5% 0.05% TFA (Aq): 0.05% TFA (Aq)+5% ACN; 1.0 mL/min, Diluent: ACN:water).

Example 60: Synthesis of 743

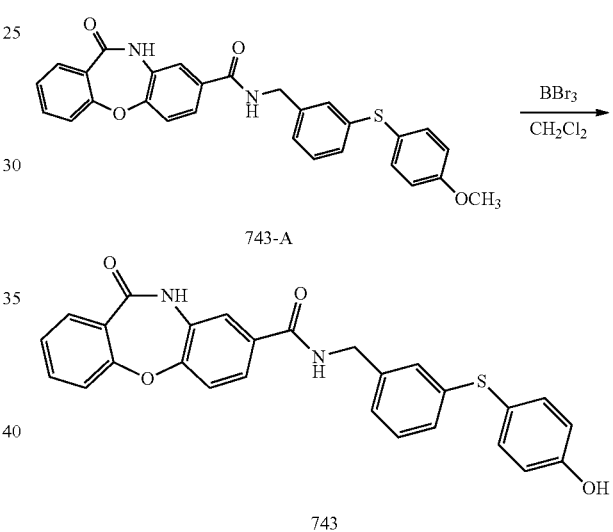

Synthesis of N-(3-((4-hydroxyphenyl)thio)benzyl)-11-oxo-10,11-dihydrodibenzo[b,f][1,4]oxazepine-8-carboxamide (743)

To a stirring solution of 743-A (70 mg, 0.14 mmol) in CH$_2$Cl$_2$ (15 mL) was added BBr3 (0.06 mL, 0.72 mmol) at 0° C. dropwise; warmed to RT and stirred for 16 h. The reaction was monitored by TLC; after completion of the reaction, the reaction mixture was quenched with ice-cold water (10 mL) and stirred for at 10 min at 0° C. The obtained solid was filtered, washed with 10% NaHCO$_3$ solution (10 mL) and dried in vacuo to afford compound 743 (50 mg, 71%) as an off-white solid. TLC: 10% MeOH/CH$_2$Cl$_2$ (R$_f$: 0.2); $^1$H-NMR (DMSO-d$_6$, 400 MHz): δ 10.62 (s, 1H), 9.83 (br s, 1H), 8.99 (t, J=5.8 Hz, 1H), 7.79 (dd, J=7.7, 1.6 Hz, 1H), 7.69-7.56 (m, 3H), 7.42 (d, J=8.3 Hz, 1H), 7.39-7.27 (m, 4H), 7.24-7.19 (m, 1H), 7.09-7.06 (m, 2H), 6.91 (d, J=8.0 Hz, 1H), 6.81 (d, J=8.7 Hz, 2H), 4.36 (d, J=5.9 Hz, 2H); LC-MS: 97.78%; 469.0 (M$^+$+1); (column; Ascentis Express C18, (50×3.0 mm, 2.7 µm); RT 2.47 min. 0.025% Aq. TFA+5% ACN:ACN+5% 0.025% Aq. TFA, 1.2 mL/min); HPLC (purity): 97.06%; (column; X-Select CSH C-18 (150×4.6 mm, 3.5 μm); RT 9.68 min. ACN+5% 0.05% TFA (Aq): 0.05% TFA (Aq)+5% ACN; 1.0 mL/min, Diluent: DMSO:ACN:water).

Example 61: Synthesis of 813

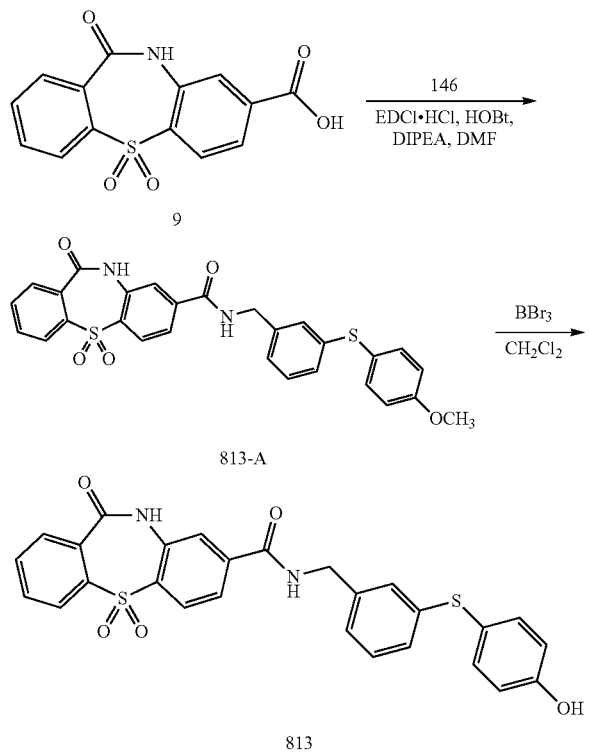

N-(3-((4-methoxyphenyl)thio)benzyl)-11-oxo-10,11-dihydrodibenzo[b,f][1,4]thiazepine-8-carboxamide 5,5-dioxide (813-A)

To a stirred solution of compound 9 (150 mg, 0.49 mmol) in DMF (8 mL) under inert atmosphere were added EDCI·HCl (190 mg, 0.99 mmol), HOBt (134 mg, 0.99 mmol) and diisopropylethylamine (0.34 mL, 1.98 mmol) and compound 146 (194 mg, 0.79 mmol) at 0° C.; warmed to RT and stirred for 16 h. The reaction was monitored by TLC; after completion of the reaction, the reaction mixture was diluted with ice-cold water (50 mL) and extracted with EtOAc (2×50 mL). The combined organic extracts were dried over sodium sulfate, filtered and concentrated in vacuo to obtain the crude. The crude was purified through silica gel column chromatography using 3% MeOH/$CH_2Cl_2$ to afford crude 813-A (100 mg) as an off white solid. TLC: 5% MeOH/$CH_2Cl_2$ ($R_f$: 0.4); LC-MS: 74.72%; 531.0 ($M^+$+1); (column; Ascentis Express C18, (50×3.0 mm, 2.7 μm); RT 2.66 min. 0.025% Aq. TFA+5% ACN:ACN+5% 0.025% Aq. TFA, 1.2 mL/min);

Synthesis of N-(3-((4-methoxyphenyl) thio) benzyl)-11-oxo-10,11-dihydrodibenzo[b,f][1,4]thiazepine-8-carboxamide 5,5-dioxide (813)

To a stirring solution of N-(3-((4-methoxyphenyl)thio) benzyl)-11-oxo-10,11-dihydrodibenzo[b,f][1,4]thiazepine-8-carboxamide 5,5-dioxide (813-A) (100 mg, 0.18 mmol) in $CH_2Cl_2$ (10 mL) was added $BBr_3$ (0.09 mL, 0.94 mmol) at 0-5° C.; warmed to RT and stirred for 16 h. The reaction was monitored by TLC; after completion of the reaction, the reaction mixture was quenched with ice-cold water (10 mL) and extracted with EtOAc (2×20 mL). The combined organic extracts were dried over sodium sulfate, filtered and concentrated in vacuo to obtain the crude. The crude was purified through silica gel column chromatography using 5% MeOH/$CH_2Cl_2$ to afford compound 813 (38 mg, 39%) as an off-white solid. TLC: 5% MeOH/$CH_2Cl_2$ ($R_f$: 0.2); $^1$H-NMR (DMSO-$d_6$, 400 MHz): δ 11.50 (s, 1H), 9.83 (s, 1H), 9.23 (t, J=5.9 Hz, 1H), 8.06 (d, J=8.3 Hz, 1H), 8.01-7.96 (m, 2H), 7.93-7.81 (m, 3H), 7.76 (dd, J=8.3, 1.5 Hz, 1H), 7.29 (d, J=8.7 Hz, 2H), 7.22 (t, J=7.3 Hz, 1H), 7.09-7.05 (m, 2H), 6.93-6.90 (m, 1H), 6.79 (d, J=8.8 Hz, 2H), 4.38 (d, J=5.9 Hz, 2H); LC-MS: 99.37%; 517.0 ($M^+$+1); (column; Ascentis Express C18, (50×3.0 mm, 2.7 μm); RT 2.45 min. 0.025% Aq. TFA+5% ACN:ACN+5% 0.025% Aq. TFA, 1.2 mL/min); HPLC (purity): 98.65%; (column; X-Select CSH C-18 (150×4.6 mm, 3.5 μm); RT 9.50 min. 5% 0.05% TFA+5% ACN:ACN+5% 0.05% TFA (Aq); 1.0 mL/min, Diluent: ACN:water).

Example 62: Synthesis of 475

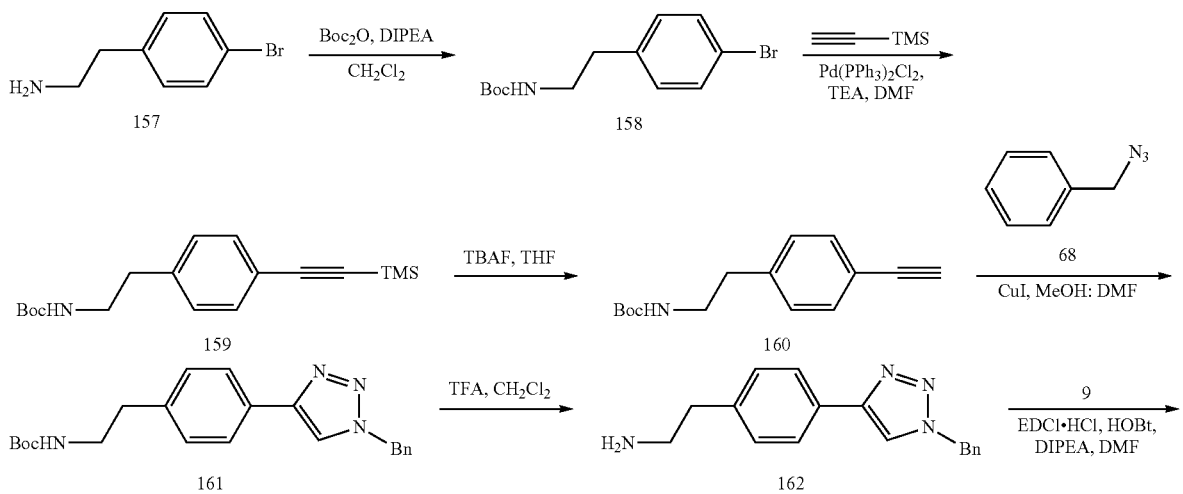

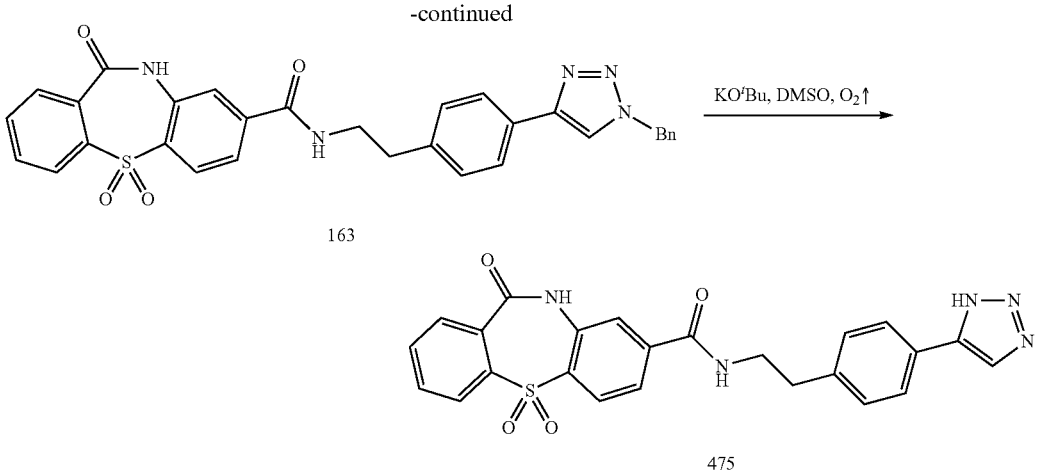

Synthesis of tert-butyl (4-bromophenethyl) carbamate (158)

To a stirred solution of 2-(4-bromophenyl)ethan-1-amine 157 (500 mg, 2.50 mmol) in CH$_2$Cl$_2$ (5 mL) under argon atmosphere were added Boc-anhydride (594 mg, 2.75 mmol), diisopropyl ethyl amine (1 mL, 7.50 mmol) at RT and stirred for 4 h. The reaction was monitored by TLC; after completion of the reaction, the reaction mixture was diluted with water (25 mL) and extracted with CH$_2$Cl$_2$ (2×35 mL). The combined organic extracts were washed with water (25 mL), dried over sodium sulfate, filtered and concentrated in vacuo to obtain the crude. The crude was purified through silica gel column chromatography using 5-8% EtOAc/hexanes to afford compound 158 (500 mg, 65%) as white solid. TLC: 10% EtOAc/hexanes (R$_f$: 0.5); $^1$H-NMR (DMSO-d$_6$, 400 MHz): δ 7.46 (d, J=8.0 Hz, 2H), 7.12 (d, J=8.0 Hz, 2H), 6.86-6.82 (m, 1H), 3.12-3.08 (m, 2H), 2.68-2.64 (m, 2H), 1.32 (s, 9H).

Synthesis of tert-butyl (4-((trimethylsilyl)ethynyl)phenethyl) carbamate (159)

To a stirred solution of compound 158 (500 mg, 1.66 mmol) in DMF (10 mL) under argon atmosphere were added ethynyltrimethylsilane (1.8 mL, 16.66 mmol), triethyl amine (2.32 mL, 16.66 mmol) and purged under argon for 15 min. To this were added Pd(PPh$_3$)$_2$Cl$_2$ (118 mg, 0.16 mmol), copper iodide (33 mg, 0.16 mmol) and purged under argon for 15 min; heated to 70° C. and stirred for 48 h. The reaction was monitored by TLC; after completion of the reaction, the volatiles were removed in vacuo to obtain the crude which was purified through silica gel column chromatography using 10% EtOAc/hexanes to afford compound 159 (500 mg, 95%) as brown syrup. TLC: 10% EtOAc/hexanes (R$_f$: 0.6); $^1$H-NMR (DMSO-d$_6$, 400 MHz): δ 7.38 (d, J=8.0 Hz, 2H), 7.18 (d, J=8.0 Hz, 2H), 6.85 (t, J=7.2 Hz, 1H), 3.16-3.11 (m, 2H), 2.70-2.66 (m, 2H), 1.34 (s, 9H), 0.23 (s, 9H).

Synthesis of tert-butyl (4-ethynylphenethyl) carbamate (160)

To a stirred solution of compound 159 (500 mg, 1.70 mmol) in THF (5 mL) under argon atmosphere was added TBAF (2.08 mL, 2.08 mmol) in THF (3 mL) at RT and stirred for 4 h. The reaction was monitored by TLC; after completion of the reaction, the volatiles were removed in vacuo to obtain the crude which was purified through silica gel column chromatography using 5-10% EtOAc/hexanes to afford compound 160 (450 mg, 95%) as brown syrup. TLC: 10% EtOAc/hexanes (R$_f$: 0.4); $^1$H-NMR (DMSO-d$_6$, 500 MHz): δ 7.39 (d, J=7.5 Hz, 2H), 7.20 (d, J=7.5 Hz, 2H), 6.87-6.85 (m, 1H), 4.10 (s, 1H), 3.15-3.12 (m, 2H), 2.71-2.69 (m, 2H), 1.30 (s, 9H).

Synthesis of tert-butyl (4-(1-benzyl-1H-1,2,3-triazol-5-yl)phenethyl) carbamate (161)

To a stirred solution of compound 160 (200 mg, 0.82 mmol) in MeOH:DMF (1: 1, 20 mL) under argon atmosphere were added (azidomethyl) benzene 68 (410 mg, 3.06 mmol), copper iodide (202 mg, 1.02 mmol) at RT; heated to reflux and stirred for 18 h. The reaction was monitored by TLC; after completion of the reaction, the volatiles were removed in vacuo to obtain the crude which was purified through silica gel column chromatography using 30% EtOAc/hexanes to afford compound 161 (200 mg, 68%) as white solid. TLC: 30% EtOAc/hexanes (R$_f$: 0.3); $^1$H-NMR (DMSO-d$_6$, 500 MHz): δ 8.59 (s, 1H), 7.75 (d, J=8.5 Hz, 2H), 7.41-7.34 (m, 5H), 7.25 (d, J=8.0 Hz, 2H), 6.90-6.88 (m, 1H), 5.64 (s, 2H), 3.17-3.13 (m, 2H), 2.70 (t, J=7.5 Hz, 2H), 1.36 (s, 9H).

Synthesis of 2-(4-(1-benzyl-1H-1,2,3-triazol-5-yl)phenyl)ethan-1-amine (162)

To a stirred solution of compound 161 (190 mg, 0.50 mmol) in CH$_2$Cl$_2$ (4 mL) under argon atmosphere was added trifluoro acetic acid (1 mL) at RT and stirred for 3 h. The reaction was monitored by TLC; after completion of the reaction, the volatiles were removed in vacuo to obtain the crude to obtain compound 162 (180 mg, crude) as dark brown syrup which was carried to the next step without any purification. TLC: 100% EtOAc (R$_f$: 0.2); $^1$H-NMR (DMSO-d$_6$, 400 MHz): δ 8.61 (s, 1H), 7.81 (d, J=8.0 Hz, 2H), 7.78-7.76 (m, 3H), 7.39-7.32 (m, 6H), 5.64 (s, 2H), 3.09-3.04 (m, 2H), 2.87 (t, J=7.6 Hz, 2H).

Synthesis of N-(4-(1-benzyl-1H-1,2,3-triazol-5-yl)phenethyl)-11-oxo-10,11-dihydrodibenzo[b,f][1,4]thiazepine-8-carboxamide 5,5-dioxide (163)

To a stirred solution compound 162 (200 mg, 0.66 mmol) in DMF (10 mL) under argon atmosphere were added EDCI.HCl (189 mg, 0.98 mmol), HOBt (189 mg, 0.98 mmol), compound 9 (297 mg, 0.79 mmol), diisopropyl ethyl amine (0.35 mL, 1.98 mmol) at 0° C.; warmed to RT and stirred for 16 h. The reaction was monitored by TLC; after completion of the reaction, the reaction mixture was diluted with EtOAc (2×50 mL) washed with water (50 mL), brine, dried over sodium sulfate, filtered and concentrated in vacuo to obtain the crude. The crude compound was purified through column chromatography using 2% MeOH/CH$_2$Cl$_2$ to afford compound 163 (180 mg, 49%) as an off-white solid. TLC: 5% MeOH/CH$_2$Cl$_2$ (R$_f$: 0.5); $^1$H NMR (DMSO-d$_6$, 400 MHz): δ 11.46 (br s, 1H), 8.80 (t, J=5.5 Hz, 1H), 8.56 (s, 1H), 8.03 (d, J=8.3 Hz, 1H), 8.00-7.95 (m, 2H), 7.92-7.83 (m, 2H), 7.79 (s, 1H), 7.75 (d, J=8.2 Hz, 3H), 7.42-7.31 (m, 5H), 7.29 (d, J=8.3 Hz, 2H), 5.63 (s, 2H), 3.50 (q, J=6.8 Hz, 2H), 2.85 (t, J=7.2 Hz, 2H).

Synthesis of N-(4-(1H-1,2,3-triazol-5-yl)phenethyl)-11-oxo-10,11-dihydrodibenzo[b,f][1,4]thiazepine-8-carboxamide 5,5-dioxide (475)

To a stirred solution of compound 163 (180 mg, 0.31 mmol) in DMSO (10 mL) under argon atmosphere was added potassium tertiary butoxide (1 M in THF, 2.5 mL, 2.55 mmol) at RT. The reaction mixture was stirred under oxygen atmosphere (balloon pressure) for 24 h. The reaction was monitored by TLC; after completion of the reaction, the reaction mixture was diluted with water (5 mL) and extracted with EtOAc (3×50 mL). The combined organic extracts were dried over sodium sulfate, filtered and concentrated in vacuo to obtain the crude. The crude compound was purified through column chromatography using 2% MeOH/CH$_2$Cl$_2$, lyophilized and washed EtOAc (5 mL), filtered, washed with n-pentane (5 mL) and dried in vacuo to afford 475 (20 mg, 13%) as white solid. TLC: 5% MeOH/CH$_2$Cl$_2$ (R$_f$: 0.3); $^1$H NMR (DMSO-d$_6$, 400 MHz): δ 14.91 (br s, 1H), 11.52 (br s, 1H), 8.81 (t, J=5.5 Hz, 1H), 8.21 (br s, 1H), 8.04 (d, J=8.3 Hz, 1H), 8.01-7.95 (m, 2H), 7.92-7.85 (m, 2H), 7.82-7.73 (m, 4H), 7.31 (d, J=7.9 Hz, 2H), 3.51 (q, J=6.6 Hz, 2H), 2.86 (t, J=7.1 Hz, 2H); LC-MS: 96.04%; 473.9 (M$^+$+1); (column; Ascentis Express C-18, (50×3.0 mm, 2.7 μm); RT 2.01 min. 0.025% Aq. TFA+5% ACN:ACN+5% 0.025% Aq. TFA, 1.2 mL/min.) HPLC (purity): 95.54%; (column; Zorbax SB C-18 (150×4.6 mm, 3.5 μm); RT 7.59 min. ACN: 0.05% TFA (Aq); 1.0 mL/min).

Example 63: Assay Measuring Activity of Compounds on Viral Production in and on Viability of AD38 Cells AD38 cells grown in a 175 cm flask with "Growth Medium" (DMEM/F12 (1:1) (cat# SH30023.01, Hyclone, 1×Pen/step (cat#: 30-002-CL, Mediatech, Inc), 10% FBS (cat#: 101, Tissue Culture Biologics), 250 μg/mL G418 (cat#: 30-234-CR, Mediatech, Inc), 1 μg/mL Tetracycline (cat#: T3325, Teknova)) were detached with 0.25% trypsin. Tetracycline-free "treatment medium" (15 mL DMEM/F12 (1:1) (cat# SH30023.01, Hyclone, lx Pen/step (cat#: 30-002-CL, Mediatech, Inc), with 2% FBS, Tet-system approved (cat#: 631106, Clontech) were then added to mix and spun at 1300 rpm for 5 min. Pelleted cells were then re-suspended/washed with 50 mL of 1×PBS 2 times and 10 mL Treatment Medium one time. AD38 cells were then re-suspended with 10 mL of Treatment Medium and counted. Wells of a collagen coated 96-well NUNC microtiter plate were seeded at 50,000/well in 180 μL of Treatment Medium, and 20 μL of in treatment media with either 10% DMSO (Control) or a 10× solution of compound in 10% DMSO was added. Plates were incubated for 6 days at 37° C.

Viral load production was assayed by quantitative PCR of the core sequence. Briefly, 5 μL of clarified supernatant was added to a PCR reaction mixture that contained forward primers HBV-f 5'-CTGTGCCTTGGGTGGCTTT-3', Reverse primers HBV-r 5'-AAGGAAAGAAGTCA-GAAGGCAAAA-3' and Fluorescent TaqMan Probes HBV-probe 5'-FAM/AGCTCCAAA/ZEN/TTCTT-TATAAGGGTCGATGTCCATG/3IABkFQ-3' in Quanta Biosciences PerfeCTa® qPCR Toughmix®, and was subsequently on an Applied Biosystems VIIA7 in a final volume of 20 μL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate).

At the end of compound treatment period cell viability was assessed using a Promega CellTiter-Glo protocol. All supernatant was removed the previously treated 96-well microtiter plate, and 50 μL Tetracycline-free treatment medium (DMEM/F12 (1:1), 1×Pen/step (cat#: 30-002-CL, Mediatech, Inc), with 2% FBS, Tet-system approved (cat#: 631106, Clontech), and 1% DMSO was added back to each well. Another 50 μL of CellTiter-Glo reagent solution (Promega, G7573) was then added at room temperature and the contents mixed for 2 minutes on an orbital shaker to induce cell lysis. This was followed by incubation at room temperature for 10 minutes to stabilize the luminescent signal. The luminescence was recorded for 0.2 seconds per well on a Tecan multimode platereader (Infinite M1000 pro). The luminescent signal from each well was normalized against that of untreated (DMSO) control wells. All results in Table 3 were reported with percent viability (with controls being 100%).

TABLE 3

Compounds and Biological activity

| Compound No. | AD38 Viral Load (%) (VL with cmpd/VL in DMSO control) at 10 μM | AD38 Viability Normalized Result (cmpd/DMSO %) at 10 μM |
| --- | --- | --- |
| 469 | 4.1 | 100 |
| 481 | 0.5 | 91 |
| 475 | 0.7 | 96 |
| 471 | 72.6 | 103 |
| 472 | 32.6 | 105 |
| 498 | 13.8 | 76 |
| 501 | 5.5 | 91 |
| 482 | 16.3 | 101 |
| 508 | 59.1 | 103 |
| 537 | 51.5 | 100 |
| 510 | 21.4 | 92 |
| 533 | 0.6 | 3 |
| 538 | 8.1 | 62 |
| 530 | 5.0 | 92 |
| 564 | 0.9 | 29 |
| 567 | 3.3 | 104 |
| 563 | 0.9 | 59 |
| 568 | 3.0 | 101 |
| 565 | 1.5 | 105 |
| 566 | 0.6 | 95 |
| 569-A | 1.5 | 97 |
| 570 | 8.7 | 112 |
| 569 | 2.8 | 100 |
| 638 | 8.6 | 7 |
| 639 | 4.5 | 34 |
| 640 | 4.4 | 1 |

TABLE 3-continued

Compounds and Biological activity

| Compound No. | AD38 Viral Load (%) (VL with cmpd/VL in DMSO control) at 10 μM | AD38 Viability Normalized Result (cmpd/DMSO %) at 10 μM |
|---|---|---|
| 652 | 36.4 | 86 |
| 652-A | 4.6 | 36 |
| 662 | 20.8 | 34 |
| 719 | 4.6 | 110 |
| 765 | 59.4 | 103 |
| 643 | 30.0 | 104 |
| 647 | 0.4 | 102 |
| 657 | 19.4 | 104 |
| 721 | 9.7 | 29 |
| 722 | 8.8 | 29 |
| 730 | 24.2 | 101 |
| 644 | 31.2 | 89 |
| 646 | 6.0 | 92 |
| 720 | 48.5 | 102 |
| 678 | 1.4 | 76 |
| 676-A | 5.9 | 98 |
| 729 | 16.3 | 97 |
| 726 | 6.1 | 1 |
| 740 | 23.8 | 103 |
| 741-A | 42.4 | 89 |
| 717 | 170.1 | 0 |
| 728-A | 66.8 | 120 |
| 741 | 40.1 | 111 |
| 742-A | 2.6 | 107 |
| 743 | 6.8 | 102 |
| 743-A | 22.7 | 91 |
| 773 | 0.6 | 87 |
| 777 | 11.7 | 99 |
| 742 | 12.7 | 89 |
| 744-A | 8.9 | 103 |
| 745-A | 16.1 | 92 |
| 775 | 2.6 | 93 |
| 776 | 63.1 | 100 |
| 744 | 62.9 | 108 |
| 745 | 38.7 | 108 |
| 774 | 48.5 | 113 |
| 812-A | 1.4 | 66 |
| 808-A | 1.5 | 84 |
| 809-A | 0.6 | 85 |
| 810-A | 1.1 | 90 |
| 812 | 5.1 | 99 |
| 808 | 3.0 | 90 |
| 809 | 1.1 | 77 |
| 810 | 3.2 | 93 |
| 811 | 1.2 | 95 |
| 811-A | 1.9 | 86 |
| 813 | 1.2 | 44 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound represented by:

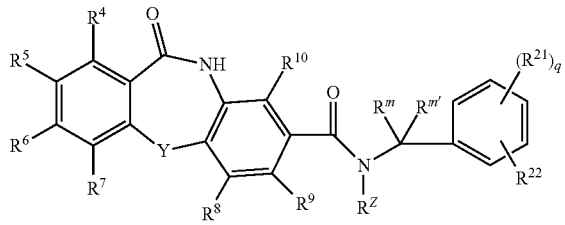

wherein

Y is $S(O)_y$, wherein y is 2;

$R^z$ is H;

$R^{m'}$ and $R^m$ are each H;

$R^{21}$ is selected for each occurrence from the group consisting of H, and $C_{1-6}$alkyl;

q is 0, 1, or 2;

$R^{22}$ is selected from the group consisting of hydroxyl, nitro, cyano, carboxy, $C_{1-6}$alkyl, $C_{2-6}$alkenyl, $C_{2-6}$alkynyl, NR'R", —C(O)—$C_{1-6}$alkyl, —C(O)—$C_{1-6}$alkoxy, —C(O)—NR'R", —C(=NH)—NR'R", $X^2$-phenyl (optionally substituted by one, two or three substituents represented by $R^{63}$), phenyl (optionally substituted by one, two or three substituents represented by $R^{63}$), 5-6 membered monocyclic heteroaryl (optionally substituted by one, two or three substituents represented by $R^{63}$), 9-10 membered bicyclic heteroaryl (optionally substituted by one, two or three substituents represented by $R^{73}$), $C_{3-6}$cycloalkyl, —S(O)$_w$-$C_{1-6}$alkyl (where w is 0, 1 or 2), —S(O)$_w$—NR'R" (where w is 0, 1 or 2), and —NR'—S(O)$_w$, (where w is 0, 1 or 2);

R' is selected, independently for each occurrence, from H, methyl, ethyl, and propyl;

R" is selected, independently for each occurrence, from H, methyl, ethyl, propyl, butyl, —C(O)-methyl and —C(O)-ethyl, or R' and R" taken together with the nitrogen to which they are attached may form a 4-7 membered heterocycle;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

$R^{63}$ is selected independently at each occurrence from the group consisting of H, halogen, hydroxyl, nitro, cyano, carboxy, $C_{1-6}$alkyl, —C(O)—O—$C_{1-6}$alkyl, heterocycle (optionally substituted by halogen or NR'R'), —C(O)—NR'R", —C(=NH)—NR'R", heteroaryl, phenyl, benzyl, $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0, 1 or 2), —S(O)$_w$—NR'R" (where w is 0, 1 or 2), —NR'—S(O)$_w$—$C_{1-6}$alkyl (where w is 0, 1 or 2), $X^2$—$R^{69}$;

$R^{69}$ is selected from the group consisting of H, halogen, hydroxyl, nitro, cyano, $C_{1-6}$alkyl, —C(O)—O—$C_{1-6}$ alkyl, heterocycle (optionally substituted by halogen or NR'R'),), —C(O)—NR'R", —C(=NH)—NR'R", heteroaryl, phenyl, $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$ alkoxy, $C_{3-6}$cycloalkyl, —S(O)$_w$—$C_{1-6}$ alkyl (where w is 0, 1 or 2), —S(O)$_w$—NR'R" (where w is 0, 1 or 2), and —NR'—S(O)$_w$— $C_{1-6}$alkyl (where w is 0, 1 or 2), $X^2$ is selected from $S(O)_w$ (wherein w is 0, 1, or 2), O, $CH_2$, or NR';

wherein for each occurrence, $C_{1-6}$alkyl may be optionally substituted with one, two, three or more substituents selected from the group consisting of halogen, hydroxyl, nitro, cyano, carboxy, $C_{2-6}$alkenyl, $C_{2-6}$alkynyl, NR'R", —NR'—S(O)$_w$—$C_{1-6}$alkyl (where w is 0, 1 or 2), and S(O)$_w$—NR'R"(where w is 0, 1 or 2); $C_{1-6}$alkoxy may be optionally substituted with one, two, three or more substituents selected from the group consisting of halogen, hydroxyl, nitro, cyano, carboxy, $C_{1-6}$alkyl, NR'R", —NR'—S(O)$_w$— $C_{1-6}$alkyl (where w is 0,1 or 2), and $S(0)_w$—NR'R" (where w is 0, 1 or 2);

and pharmaceutically acceptable salts thereof.

2. The compound of claim 1, wherein $R^{22}$ is selected from the group consisting of NR'R", —C(O)—$C_{1-6}$alkyl, —C(O)—$C_{1-6}$alkoxy, —C(O)—NR'R", —C(=NH)—NR'R", $X^2$-phenyl (optionally substituted by one, two or three substituents represented by $R^{63}$), phenyl (optionally substituted by one, two or three substituents represented by $R^{63}$), $C_{3-6}$cycloalkyl, —S(O)$_w$—$C_{1-6}$alkyl (where w is 0, 1 or 2), —S(O)$_w$—NR'R" (where w is 0, 1 or 2), and —NR'—S(O)$_w$, (where w is 0, 1 or 2).

3. The compound of claim 1, wherein $R^{22}$ is selected from the group consisting of $X^2$-phenyl (optionally substituted by one, two or three substituents represented by $R^{63}$), phenyl (optionally substituted by one, two or three substituents represented by $R^{63}$), 5-6 membered monocyclic heteroaryl (optionally substituted by one, two or three substituents represented by $R^{63}$), and 9-10 membered bicyclic heteroaryl (optionally substituted by one, two or three substituents represented by $R^{73}$).

4. The compound of claim 1, wherein $R^{22}$ is —$X^2$-phenyl (optionally substituted by one, two or three substituents represented by $R^{63}$).

5. The compound of claim 1, wherein $R^{22}$ is phenyl (optionally substituted by one, two or three substituents represented by $R^{63}$).

6. The compound of claim 1, wherein $R^{22}$ is a 5-6 membered monocyclic heteroaryl (optionally substituted by one, two or three substituents represented by $R^{63}$) or a 9-10 membered bicyclic heteroaryl (optionally substituted by one, two or three substituents represented by $R^{73}$).

7. The compound of claim 1, wherein q is 0.

8. The compound of claim 1, represented by:

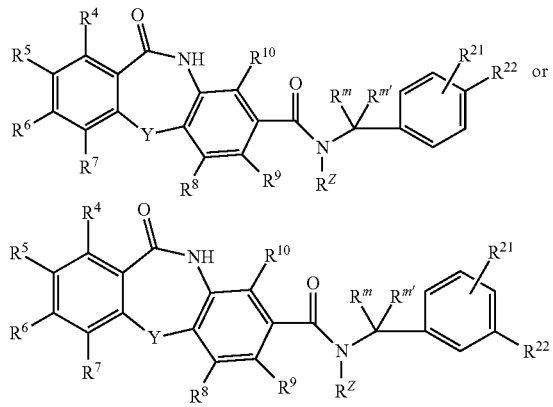

wherein $R^{21}$ is selected from the group consisting of H and $C_{1-6}$alkyl.

9. The compound of claim 1, wherein the compound is represented by:

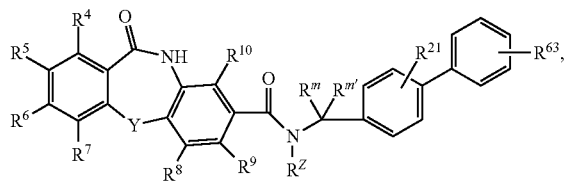

wherein $R^{21}$ is selected from the group consisting of H and $CH_3$.

10. The compound of claim 1, wherein the compound is represented by:

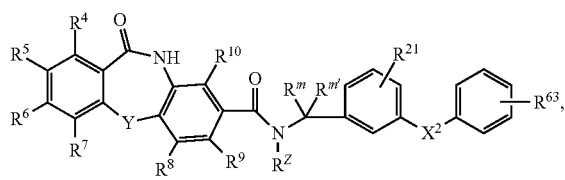

wherein $X^2$ is selected from the group consisting of O, $CH_2$, and S, and $R^{21}$ is selected from the group consisting of H and $CH_3$.

11. The compound of claim 1, wherein $R^{22}$ is represented by a substituent selected from the group consisting of:

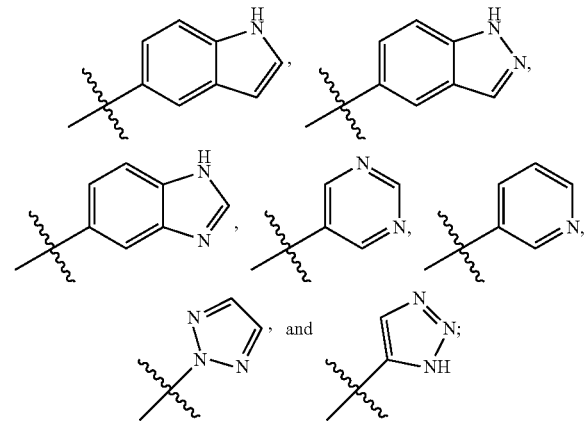

wherein each $R^{22}$ is optionally substituted by one, two or three substituents represented by $R^{63}$.

12. The compound of claim 1, wherein
$R^{63}$ is selected independently at each occurrence from the group consisting of H, halogen, hydroxyl, nitro, cyano, $C_{1-6}$alkyl, $C_{1-6}$haloalkyl, —$C_{1-6}$alkyl-OH, —C(O)—O—$C_{1-6}$alkyl, —C(O)—NR'R", —C(=NH)—NR'R", $C_{2-6}$alkenyl, $C_{2-6}$alkynyl, $C_{1-6}$alkoxy, carboxy, NR'R", —C(O)—$C_{1-6}$alkyl, —C(O)—$C_{1-6}$alkoxy, $C_{3-6}$cycloalkyl, —S(O)$_w$—$C_{1-6}$alkyl (where w is 0,1 or 2), —S(O)$_w$—NR'R" (where w is 0, 1 or 2), —NR'—S(O)$_w$—$C_{1-6}$alkyl (where w is 0, 1 or 2) and —NR'—S(O)$_w$, (where w is 0, 1 or 2) and $X^2$—$C_{1-6}$alkylene-$R^{69}$.

13. The compound of claim 1, wherein
$R^{63}$ is selected independently at each occurrence from the group consisting of H, halogen, hydroxyl, cyano, $C_{1-6}$alkyl, $C_{1-6}$haloalkyl, $C_{1-6}$alkyl-OH, $C_{1-6}$alkyl-NR'R", —O—$C_{1-6}$alkyl-NR'R", —$C_{1-6}$alkyl-OH, —C(O)—NR'R", $C_{1-6}$alkoxy, carboxy, NR'R", and benzyl.

14. A pharmaceutically acceptable composition comprising a compound of claim 1, and a pharmaceutically acceptable excipient.

15. A method of treating a hepatitis B infection in a patient in need thereof, comprising administering an effective amount of a compound of claim 1.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: PCR Primer

<400> SEQUENCE: 1
ctgtgccttg ggtggcttt                                                19

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
aaggaaagaa gtcagaaggc aaaa                                          24
```

```
<210> SEQ ID NO 3
<211> LENGTH: 34
<212> TYPE: DNA
<213> ORGANISM: Artificial Sequence
<220> FEATURE:
<223> OTHER INFORMATION: PCR Probe

<400> SEQUENCE: 3
agctccaaat tctttataag ggtcgatgtc catg                34
```